(12) United States Patent
Cullis et al.

(10) Patent No.: US 10,041,091 B2
(45) Date of Patent: *Aug. 7, 2018

(54) NUCLEIC ACID-CONTAINING LIPID PARTICLES AND RELATED METHODS

(71) Applicant: The University of British Columbia, Vancouver (CA)

(72) Inventors: Pieter R. Cullis, Vancouver (CA); Nathan M. Belliveau, Weymouth (CA); Carl Lars Genghis Hansen, Vancouver (CA); Jens Huft, Vancouver (CA); Robert James Taylor, Vancouver (CA); Andre Wild, Vancouver (CA); Stuart Malcolm, West Vancouver (CA); Ismail Hafez, Vancouver (CA); Alex Leung, Vancouver (CA); David Walker, Surrey (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,218

(22) Filed: Aug. 25, 2017

(65) Prior Publication Data

US 2018/0044699 A1 Feb. 15, 2018

Related U.S. Application Data

(63) Continuation of application No. 13/464,690, filed on May 4, 2012, now Pat. No. 9,758,795, which is a continuation of application No. PCT/CA2010/001766, filed on Nov. 4, 2010.

(60) Provisional application No. 61/280,510, filed on Nov. 4, 2009.

(51) Int. Cl.
| | | |
|---|---|---|
| *A61K 38/00* | (2006.01) |
| *A61K 9/127* | (2006.01) |
| *C12N 15/88* | (2006.01) |
| *A61K 31/7088* | (2006.01) |
| *A61K 47/22* | (2006.01) |
| *C12N 15/11* | (2006.01) |
| *A61K 9/14* | (2006.01) |
| *C07K 17/00* | (2006.01) |
| *A61K 48/00* | (2006.01) |

(52) U.S. Cl.
CPC ............ *C12N 15/88* (2013.01); *A61K 9/1272* (2013.01); *A61K 31/7088* (2013.01); *A61K 47/22* (2013.01); *C12N 15/111* (2013.01); *C12N 2320/32* (2013.01)

(58) Field of Classification Search
None
See application file for complete search history.

(56) References Cited

U.S. PATENT DOCUMENTS

| | | |
|---|---|---|
| 5,921,678 A | 7/1999 | Desai |
| 5,981,501 A | 11/1999 | Wheeler |
| 6,479,299 B1 | 11/2002 | Parce |
| 6,534,484 B1 | 3/2003 | Wheeler et al. |
| 6,815,432 B2 | 11/2004 | Wheeler |
| 6,835,395 B1 | 12/2004 | Semple et al. |
| 6,843,942 B2 | 1/2005 | Katinger |
| 7,005,140 B2 | 2/2006 | Zhang |
| 7,160,025 B2 | 1/2007 | Ji |
| 7,214,348 B2 | 5/2007 | Desmond |
| 7,252,928 B1 | 8/2007 | Hafeman |
| 7,341,738 B2 | 3/2008 | Semple et al. |
| 7,422,902 B1 | 9/2008 | Wheeler et al. |
| 7,507,380 B2 | 3/2009 | Chang |
| 7,622,509 B2 | 11/2009 | Tonkovich |
| 7,708,949 B2 | 5/2010 | Stone |
| 7,745,221 B2 | 6/2010 | Butler |
| 7,794,136 B2 | 9/2010 | Yang |
| 7,901,708 B2 | 3/2011 | MacLachlan |
| 8,058,069 B2 | 11/2011 | Yaworski |
| 8,106,176 B2 | 1/2012 | Aurisicchio |
| 8,122,909 B2 | 2/2012 | Tonkovich |
| 8,137,699 B2 | 3/2012 | Johnson |
| 8,273,573 B2 | 9/2012 | Ismagilov |
| 8,329,070 B2 | 12/2012 | MacLachlan |
| 8,361,415 B2 | 1/2013 | Di Carlo |
| 8,367,004 B2 | 2/2013 | Panagiotou |
| 8,414,182 B2 | 4/2013 | Paul |
| 8,492,359 B2 | 7/2013 | Yaworski |
| 8,496,961 B2 | 7/2013 | Hong |
| 8,522,413 B2 | 9/2013 | Van't Oever |
| 8,883,200 B2 | 11/2014 | Hong |

(Continued)

FOREIGN PATENT DOCUMENTS

| | | |
|---|---|---|
| JP | 2005-515815 A | 6/2005 |
| JP | 2005-525815 A | 9/2005 |

(Continued)

OTHER PUBLICATIONS

Abrams, M.T., et al., "Evaluation of Efficacy, Biodistribution, and Inflammation for a Potent siRNA Nanoparticle: Effect of Dexamethasone Co-Treatment," Molecular Therapy 18(1):171-180, Jan. 2010.

Belliveau, N.M., et al., "Microfluidic Synthesis of Highly Potent Limit-Size Lipid Nanoparticles for In Vivo Delivery of siRNA," Molecular Therapy—Nucleic Acids 1(8):1-9, Aug. 2012.

Chen, D., et al., "Rapid Discovery of Potent siRNA-Containing Lipid Nanoparticles Enabled by Controlled Microfluidic Formulation," Journal of the American Chemical Society (JACS) 134(16):6948-6951, Apr. 2012.

Communication Pursuant to Article 94(3) EPC, dated Jul. 18, 2014, in European Application No. 10851175.9, filed Nov. 4, 2010, 7 pages.

(Continued)

*Primary Examiner* — Robert T. Crow
*Assistant Examiner* — John P Nguyen
(74) *Attorney, Agent, or Firm* — Christensen O'Connor Johnson Kindness PLLC

(57) ABSTRACT

Lipid particles containing a nucleic acid, devices and methods for making the lipid particles, and methods for using the lipid particles.

20 Claims, 33 Drawing Sheets

(56) References Cited

U.S. PATENT DOCUMENTS

| | | | |
|---|---|---|---|
| 9,005,654 | B2 | 4/2015 | MacLachlan |
| 9,006,417 | B2 | 4/2015 | Yaworski et al. |
| 9,404,127 | B2 | 9/2016 | Yaworski et al. |
| 9,518,272 | B2 | 12/2016 | Yaworski et al. |
| 2004/0037874 | A1 | 2/2004 | Hong et al. |
| 2004/0262223 | A1 | 12/2004 | Strook |
| 2006/0051405 | A1 | 3/2006 | MacLachlan et al. |
| 2006/0134189 | A1 | 6/2006 | MacLaughlin et al. |
| 2006/0219307 | A1 | 10/2006 | Wang |
| 2006/0260777 | A1 | 11/2006 | Rashba-Step et al. |
| 2007/0042031 | A1 | 2/2007 | MacLachlan et al. |
| 2009/0291131 | A1 | 11/2009 | MacLaughlin et al. |
| 2010/0022680 | A1 | 1/2010 | Kamik |
| 2010/0130588 | A1 | 5/2010 | Yaworski et al. |
| 2011/0091525 | A1 | 4/2011 | Heyes et al. |
| 2011/0182994 | A1 | 7/2011 | Komfield |
| 2011/0262527 | A1 | 10/2011 | Heyes et al. |
| 2011/0305734 | A1 | 12/2011 | Edelson |
| 2011/0311582 | A1 | 12/2011 | Manoharan et al. |
| 2011/0311583 | A1 | 12/2011 | Manoharan et al. |
| 2013/0303587 | A1 | 11/2013 | Yaworski |

FOREIGN PATENT DOCUMENTS

| | | | |
|---|---|---|---|
| JP | 2007-252979 A | 4/2007 | |
| JP | 2007-524604 A | 8/2007 | |
| JP | 2007-533647 A | 11/2007 | |
| JP | 2008-526493 A | 7/2008 | |
| JP | 2008-001771 A | 10/2008 | |
| JP | 2009-509553 A | 3/2009 | |
| JP | 2013-510096 A | 3/2013 | |
| WO | 03/097805 A2 | 11/2003 | |
| WO | 2005/026372 A1 | 3/2005 | |
| WO | 2005/039535 A1 | 5/2005 | |
| WO | 2005/120152 A2 | 12/2005 | |
| WO | 2005/120461 A2 | 12/2005 | |
| WO | 2006/053430 A1 | 5/2006 | |
| WO | 2006/074336 A1 | 7/2006 | |
| WO | 2008/053988 A1 | 5/2008 | |
| WO | 2009/086558 A1 | 7/2009 | |
| WO | 2009/127060 A1 | 10/2009 | |
| WO | WO-2009120247 A2 * | 10/2009 | ............ C12N 15/88 |
| WO | 2011/140627 A1 | 11/2011 | |
| WO | 2012/000104 A1 | 1/2012 | |
| WO | 2012/016184 A2 | 2/2012 | |

OTHER PUBLICATIONS

Crawford, R., et al., "Analysis of Lipid Nanoparticles by Cryo-EM for CharacterizingsiRNA Delivery Vehicles," International Journal of Pharmaceutics 403(1-2):237-244, Jan. 2011.

Decision of Rejection dated Apr. 7, 2015 (with foreign associates comments), issued in Japanese Application No. 2012-537274, filed Nov. 4, 2010, 6 pages.

First Office Action dated Jul. 15, 2014, issued in corresponding Japanese Patent Application No. 2012-537274, filed Nov. 4, 2010, 5 pages.

First Office Action dated Jul. 5, 2016, issued in corresponding Japanese Application No. 2015-157385, filed Aug. 7, 2015, 5 pages.

Geusens, B., et al., "Ultradeformable Cationic Liposomes for Delivery of Small Interfering RNA (siRNA) Into Human Primary Melanocytes," Journal of Controlled Release 133(3):214-220, Feb. 2009.

Gindy, M.E. et al. "Mechanism of Macromolecular Structure Evolution in Self-Assembled Lipid Nanoparticles for siRNA Delivery," Langmuir 30(16):4613-4622, Apr. 2014.

Heyes, J., et al., "Lipid Encapsulation Enables the Effective Systemic Delivery of Polyplex Plasmid DNA," Molecular Therapy 15(4):713-720, Apr. 2007.

International Search Report and Written Opinion dated Feb. 8,2011, issued in corresponding International Application No. PCT/CA2010/001766, filed Nov. 4, 2010, 17 pages.

Jahn, A, et al., "Preparation of Nanoparticles by Continuous-Flow Microfluidics," Journal of Nanoparticle Research 10(6):925-934, Aug. 2008.

Jeffs, L.B., et al., "A Scalable, Extrusion-Free Method for Efficient Liposomal Encapsulation of Plasmid DNA," Pharmaceutical Research 22(3)362-372, Mar. 2005.

Johnson, B.K., and R.K. Prud'homme, "Mechanism for Rapid Self-Assembly of Block Copolymer Nanoparticles," Physical Review Letters 91(11):118302-1-118302-4, Sep. 2003.

Kapoor, M., et al., "Physicochemical Characterization Techniques for Lipid Based Delivery Systems for siRNA," International Journal of Pharmaceutics 427(1):35-57, May 2012.

Karnik, R., et al., "Microfluidic Platform for Controlled Synthesis of Polymeric Nanoparticles," Nano Letters 8(9):2906-2912, Sep. 2008.

Koh, C G. et al., "Delivery of Antisense Oligodeoxyribonucleotide Lipopolyplex Nanoparticles Assembled by Microfluidic Hydrodynamic Focusing," Journal of Controlled Release 141(1):62-69, Jan. 2010.

MacLachlan, I., "Liposomal Formulations for Nucleic Acid Delivery," in S.T. Crooke (ed.), "Antisense Drug Technology: Principles, Strategies, and Applications," 2nd. ed., Chap. 9, CRC Press, Boca Raton, Fla., Jul. 2007.

Montana, G., et al., "Employment of Cationic Solid-Lipid Nanoparticles as RNA Carriers," Bioconjugate Chemistry 18(2)302-308, Mar.-Apr. 2007.

Notification Concerning Transmittal of International Preliminary Report on Patentability, International Preliminary Report on Patentability and Written Opinion dated May 18, 2012, issued in corresponding International Application No. PCT/CA2010/001766, filed Nov. 4, 2010, 11 pages.

Notification of the Second Office Action dated Jan. 24, 2014, in corresponding Chinese Application No. 201080059999.7, filed Nov. 4, 2010, 4 pages.

Notification of the Third Office Action, dated Oct. 15, 2014, issued in corresponding Chinese Application No. 201080059999.7, filed Nov. 4, 2010, 7 pages.

Notification of the Fourth Office Action dated Jul. 6, 2015, issued in corresponding Chinese Application No. 201080059999.7, filed Nov. 4, 2010, 10 pages.

Notification of the Fifth Office Action, dated Mar. 28, 2016, issued in corresponding Chinese Application No. 201080059999.7, filed Nov. 4, 2010, 9 pages.

Notification of the Sixth Office Action, dated Sep. 30, 2016, issued in corresponding Chinese Application No. 201090059999.7, filed Nov. 4, 2010, 7 pages.

Office Action dated Jan. 30, 2017, issued in Canadian Application No. 2,816,925, filed Nov. 4, 2010, 6 pages.

Office Action dated Oct. 10, 2014, issued in corresponding Russian Application No. 2012122776, filed Nov. 4, 2010, 12 pages.

Seo, M., et al., "Microfluidic Assembly of Monodisperse, Nanoparticle-Incorporated PerfluorocarbonMicrobubbles for Medical Imaging and Therapy," Langmuir 26(17):13855-13860, Sep. 2010.

Supplementary European Search Report dated Dec. 6, 2013, issued in corresponding European Application No. 10 85 1175.9, filed Nov. 4, 2010, 9 pages.

Szoka, F., Jr., "Comparative Properties and Methods of Preparation of LipidVesicles (Liposomes)," Annual Review of Biophysics and Bioengineering 9:467-508,1980.

Xu, Y., et al., "Physicochemical Characterization and Purification of Cationic Lipoplexes," Biophysical Journal 77(1):341-353, Jul. 1999.

Yu, B., et al., "Microfluidic Methods for Production of Liposomes," Methods in Enzymology 465:129-141, 2009.

Zhang J., et al., "Assessing the Heterogeneity Level in Lipid Nanoparticles for siRNA Delivery: Size=Based Separation, Composition al Heterogeneity, and Impact of Bioperformance," Molecular Pharmaceutics 10(1):397-405, Jan. 2013.

Zhang, J., et al., "Polydispersity Characterization of Lipid Nanoparticles for siRNA Delivery Using Multiple Detection Size-Exclusion Chromatography," Analytical Chemistry 84(14):6088-6096, Jul. 2012.

(56) References Cited

OTHER PUBLICATIONS

Hope, M.J, et al., "Generation of Multilamellar and Unilamellar Phospholipid Vesicles," Chemistry and Physics of Lipids 40(2-4):89-107, Jun.-Jul. 1986.

Maurer, N., et al., "Spontaneous Entrapment of Polynucleotides Upon Electrostatic Interaction With Ethanol-Destabilized Cationic Liposomes," Biophysical Journal 80(5):2310-2326, May 2001.

First Examination Report dated Dec. 4, 2017, issued in corresponding Indian Application No. 1289/MUMNP/2012, filed Nov. 4, 2010, 9 pages.

Grounds for Opposition Against EP 2 496 700 B1, Dec. 1, 2017.

Notice of Opposition to European Patent No. EP 2496700, Opponent Merck, Sharp & Dohme Corp., Dec. 1, 2017.

Acknowledgement of Receipt—Opposition proceedings in relation to EP 10851175.9, Submission No. 5839011, Dec. 1, 2017.

Opposition against European Patent No. EP 2496700, granted from European Patent Application No. 10851175.9, in The name of University of British Columbia, Nov. 30, 2017.

Notice of Opposition to European Patent No. EP 2496700, Opponent Withers & Rogers LLP, Nov. 30, 2017.

Acknowledgement of Receipt—Opposition proceedings in relation to EP 10851175.9, Submission No. 5835670, Nov. 30, 2017.

Dictionary Excerpts for the term "Surround," various sources, as early as Jan. 27, 2018, 7 pages.

Jeffs, L.B., et al., "A Scalable, Extrusion-Free Method for Efficient Liposomal Encapsulation of Plasmid DNA," Pharmaceutical Research 22(3):362-372, Mar. 2005.

Maurer, N., et al.,"Spontaneous Entrapment of Polynucleotides Upon Electrostatic Interaction With Ethanol-Destabilized Cationic Liposomes," Biophysical Journal 80(5):2310-2326, May 2001.

Micklefield, J., "Backbone Modification of Nucleic Acids: Synthesis, Structure and Therapeutic Applications," Current Medicinal Chemistry 8(10):1157-1179, Aug. 2001.

Rana, T.M., "Illuminating the Silence: Understanding the Structure and Function of Small RNAs," Nature Reviews: Molecular Cell Biology 8(1):23-36, Jan. 2007.

Semple, S.C., et al., "Rational Design of Cationic Lipids for siRNA Delivery," Nature Biotechnology 8(2):172-176, Feb. 2010.

Stroock, A., et al., "Chaotic Mixer for Microchannels," Science 295(5555):647-651, Jan. 2002.

Üner, M., et al., "Importance of Solid Lipid Nanoparticles (SLN) in Various Administration Routes and Future Perspective," International Journal of Nanomedicine 2(3):289-300,2007.

Üner, M., et al., "Preparation, Characterization and Physico-Chemical Properties of Solid Lipid Nanoparticles (SLN) and Nanostructured Lipid Carriers (NLC): Their Benefits as Colloidal Drug Carrier Systems," Pharmazie 61(5):375-386, May 2006.

Zhang, S.-H., et al., "Preparation of Solid Lipid Nanoparticles in Co-Flowing Microchannels," Chemical Engineering Journal 144(2):324-328, Oct. 2008.

Zimmerman, T.S., et al., "RNAi-Mediated Gene Silencing in Non-Human Primates," Nature 441(7089):111-114, May 2006.

* cited by examiner

NUCLEIC ACID-CONTAINING LIPID PARTICLES AND RELATED METHODS

CROSS-REFERENCES TO RELATED APPLICATIONS

This application is a continuation of U.S. application Ser. No. 13/464,690, filed May 4, 2012 (now U.S. Pat. No. 9,758,795), which is a continuation of International Application No. PCT/CA2010/001766, filed Nov. 4, 2010, which claims the benefit of U.S. Provisional Application No. 61/280,510, filed Nov. 4, 2009, each of which is expressly incorporated herein by reference in its entirety.

BACKGROUND OF THE INVENTION

Lipid nanoparticles (LNP) are the most clinically advanced drug delivery systems, with seven LNP-based drugs having received regulatory approval. These approved drugs contain small molecules such as anticancer drugs and exhibit improved efficacy and/or reduced toxicity compared to the "free" drug. LNP carrier technology has also been applied to delivery of "genetic" drugs such as plasmids for expression of therapeutic proteins or small interfering RNA (siRNA) oligonucleotides (OGN) for silencing genes contributing to disease progression. Devising methods for efficient in vivo delivery of siRNA OGN and other genetic drugs is the major problem impeding the revolutionary potential of these agents as therapeutics.

Recent advances in LNP technology and the design of the cationic lipids required for encapsulation and delivery of genetic drugs highlight the potential of LNP systems to solve the in vivo delivery problem. LNP-siRNA systems have been shown to induce silencing of therapeutically relevant target genes in animal models, including non-human primates following intravenous (i.v.) injection and are currently under evaluation in several clinical trials.

A variety of methods have been developed to formulate LNP systems containing genetic drugs. These methods include mixing preformed LNP with OGN in the presence of ethanol or mixing lipid dissolved in ethanol with an aqueous media containing OGN and result in LNP with diameters of 100 nm or less and OGN encapsulation efficiencies of 65-95%. Both of these methods rely on the presence of cationic lipid to achieve encapsulation of OGN and poly (ethylene glycol) (PEG) lipids to inhibit aggregation and the formation of large structures. The properties of the LNP systems produced, including size and OGN encapsulation efficiency, are sensitive to a variety of formulation parameters such as ionic strength, lipid and ethanol concentration, pH, OGN concentration and mixing rates. In general, parameters such as the relative lipid and OGN concentrations at the time of mixing, as well as the mixing rates are difficult to control using current formulation procedures, resulting in variability in the characteristics of LNP produced, both within and between preparations.

Microfluidic devices provide an ability to controllably and rapidly mix fluids at the nanoliter scale with precise control over temperature, residence times, and solute concentrations. Controlled and rapid microfluidic mixing has been previously applied in the synthesis of inorganic nanoparticles and microparticles, and can outperform macroscale systems in large scale production of nanoparticles. Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated. This technique has also proven useful in the production of polymeric nanoparticles where smaller, more monodisperse particles were obtained, with higher encapsulation of small molecules as compared to bulk production methods.

Despite advances in the development of methods for LNP systems containing genetic drugs, a need exist for devices and methods for preparing lipid nanoparticles containing therapeutic materials, as well as improved lipid nanoparticles containing therapeutic materials. The present invention seeks to fulfill this need and provides further related advantages.

SUMMARY OF THE INVENTION

In one aspect, the invention provides lipid particles comprising nucleic acids.

In one embodiment, the lipid particle comprises (a) one or more cationic lipids, (b) one or more second lipids, and (c) one or more nucleic acids, wherein the lipid particle comprises a substantially solid core, as defined herein.

In one embodiment, the cationic lipid is DLin-KC2-DMA. In certain embodiments, the particle comprises from about 30 to about 95 mole percent cationic lipid.

In one embodiment, the second lipid is PEG-c-DMA. In one embodiment, the second lipid is 1,2-distearoyl-sn-glycero-3-phosphocholine (DSPC). In certain embodiments, the particle comprises from about 1 to about 10 mole percent second lipid.

The nucleic acid can be a DNA, a RNA, a locked nucleic acid, a nucleic acid analog, or a plasmid capable of expressing a DNA or an RNA.

In another embodiment, the lipid particle comprises (a) one or more cationic lipids, (b) one or more neutral lipids, (c) one or more PEG-lipids, (d) one or more sterols; and (e) one or more nucleic acids, wherein the lipid particle comprises a substantially solid core, as defined herein. In one embodiment, the cationic lipid is DLin-KC2-DMA. In one embodiment, the PEG-lipid is PEG-c-DMA. In one embodiment, the neutral lipid is 1,2-distearoyl-sn-glycero-3-phosphocholine (DSPC). In one embodiment, the sterol is cholesterol. In one embodiment, nucleic acid is an siRNA.

In a further embodiment, the lipid particle consists of one or more cationic lipids, and one or more nucleic acids. In one embodiment, the lipid particle comprises a substantially solid core, as defined herein. In one embodiment, the cationic lipid is DLin-KC2-DMA. In one embodiment, the nucleic acid is an siRNA.

In other aspects, the invention provides methods for using the lipid particles.

In one embodiment, the invention provides a method for administering a nucleic acid to a subject, comprising administering a lipid particle of the invention to a subject in need thereof.

In one embodiment, the invention provides a method for introducing a nucleic acid into a cell, comprising contacting a cell with the lipid particle of the invention.

In one embodiment, the invention provides a method for modulating the expression of a target polynucleotide or polypeptide, comprising contacting a cell with the lipid particle of the invention, wherein the nucleic acid capable of modulating the expression of a target polynucleotide or polypeptide.

In one embodiment, the invention provides a method of treating a disease or disorder characterized by overexpression of a polypeptide in a subject, comprising administering to the subject the lipid particle of the invention, wherein the nucleic acid capable of silencing or decreasing the expression of the polypeptide.

In other aspect, the invention provides a method for making lipid particles.

In one embodiment, the invention provides a method for making lipid particles containing a nucleic acid, comprising:

(a) introducing a first stream comprising a nucleic acid in a first solvent into a microfluidic device; wherein the device has a first region adapted for flowing one or more streams introduced into the device and a second region for mixing the contents of the one or more streams with a microfluidic mixer;

(b) introducing a second stream comprising lipid particle-forming materials in a second solvent into the device to provide first and second streams flowing under laminar flow conditions, wherein the device has a first region adapted for flowing one or more streams introduced into the microchannel and a second region for mixing the contents of the one or more streams, wherein the lipid particle-forming materials comprise a cationic lipid, and wherein the first and second solvents are not the same;

(c) flowing the one or more first streams and the one or more second streams from the first region of the device into the second region of the device; and (d) mixing of the contents of the one or more first streams and the one or more second streams flowing under laminar flow conditions in the second region of the device to provide a third stream comprising lipid nanoparticles with encapsulated nucleic acid.

In another embodiment, the invention provides a method for making lipid particles containing a nucleic acid, comprising:

(a) introducing a first stream comprising a nucleic acid in a first solvent into a channel; wherein the device has a first region adapted for flowing one or more streams introduced into the channel and a second region for mixing the contents of the one or more streams;

(b) introducing a second stream comprising lipid particle-forming materials in a second solvent; wherein the channel has a first region adapted for flowing one or more streams introduced into the channel and a second region for mixing the contents of the one or more streams;

(c) flowing the one or more first streams and the one or more second streams from the first region of the channel into the second region of the channel, while maintaining a physical separation of the two streams, wherein the one or more first streams and the one or more second streams do not mix until arriving at the second region of the channel; and (d) mixing of the contents of the one or more first streams and the one or more second streams flowing under laminar flow conditions in the second region of the microchannel to provide a third stream comprising lipid nanoparticles with encapsulated nucleic acids.

In certain embodiments of the above methods, mixing the contents of the one or more first streams and the one or more second streams comprises varying the concentration or relative mixing rates of the one or more first streams and the one or more second streams.

In certain embodiments of the above methods, the methods further comprise diluting the third stream with an aqueous buffer. In certain embodiments, diluting the third stream comprises flowing the third stream and an aqueous buffer into a second mixing structure.

In certain embodiments of the above methods, the methods further comprise dialyzing the aqueous buffer comprising lipid particles with encapsulated nucleic acids to reduce the amount of the second solvent.

In certain embodiments of the above methods, the first solvent is an aqueous buffer. In certain embodiments of the above methods, the second solvent is an aqueous alcohol.

In certain embodiments of the above methods, mixing the contents of the first and second streams comprises chaotic advection. In certain embodiments of the above methods, mixing the contents of the first and second streams comprises mixing with a micromixer.

In certain embodiments of the above methods, the nucleic acid encapsulation efficiency is from about 90 to about 100%.

In certain embodiments of the above methods, mixing of the one or more first streams and the one or more second streams is prevented in the first region by a barrier. In certain embodiments, the barrier is a channel wall, sheath fluid, or concentric tubing.

In another aspect of the invention, devices for making lipid particles are provided. In one embodiment, the invention provides a device for producing a lipid particle encapsulating a nucleic acid, comprising:

(a) a first inlet for receiving a first solution comprising a nucleic acid in a first solvent;

(b) a first inlet microchannel in fluid communication with the first inlet to provide a first stream comprising the nucleic acid in the first solvent;

(c) a second inlet for receiving a second solution comprising lipid particle-forming materials in a second solvent;

(d) a second inlet microchannel in fluid communication with the second inlet to provide a second stream comprising the lipid particle-forming materials in the second solvent; and (e) a third microchannel for receiving the first and second streams, wherein the third microchannel has a first region adapted for flowing the first and second streams introduced into the microchannel under laminar flow conditions and a second region adapted for mixing the contents of the first and second streams to provide a third stream comprising lipid particles with encapsulated nucleic acid.

In one embodiment, the device further comprises means for diluting the third stream to provide a diluted stream comprising stabilized lipid particles with encapsulated nucleic acid. In certain embodiments, the means for diluting the third stream comprises a micromixer.

In one embodiment, the microchannel has a hydrodynamic diameter from about 20 to about 300 µm.

In one embodiment, the second region of the microchannel comprises bas-relief structures. In one embodiment, the second region of the microchannel has a principal flow direction and one or more surfaces having at least one groove or protrusion defined therein, the groove or protrusion having an orientation that forms an angle with the principal direction. In one embodiment, the second region comprises a micromixer.

In certain embodiments, the device further comprises means for varying the flow rates of the first and second streams.

In certain embodiments, the device further comprises a barrier effective to physically separate the one or more first streams from the one or more second streams in the first region.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 16A compares the extent of mixing (%) as determined by mean fluorescent intensity along channel width as a function of with mixing time (msec) calculated from average fluid velocity and travel length (0.2, 0.8, 1.4, and 2 mL/min). FIGS. 16B and 16C compare mean particle diameter for LNP composed of Dlin-KC2-DMA/DSPC/Cholesterol/PEG-c-DMA at mole ratios of 40:11.5:47.5:1, siRNA-total lipid ratio 0.06 wt/wt, with 10 mM lipid-ethanol phase mixed with 25 mM acetate buffer, pH 4, containing siRNA. FIG. 16B compares mean particle diameter (nm) for LNP as a function of flow rate (mL/min). FIG. 16C compares mean particle diameter (nm) for LNP as a function of ethanol/aqueous flow rate ratio. Error bars represent standard deviation of the mean particle diameter as measured by dynamic light scattering.

FIG. 18A compares mean particle diameter (nm) as a function of PEG-c-DMA content (mol % in LNP) for LNP prepared by the PFV and MF methods. The PEG-lipid was varied from 1 mol % to 10 mol % in the LNP composition. Modification of PEG-lipid content was compensated by adjustment of cholesterol content. LNP were composed of Dlin-KC2-DMA/DSPC/Cholesterol/PEG-c-DMA at mole ratios of 40:11.5:47.5:1 (−x):1 (+x), (where x=1 to 9), siRNA-total lipid ratio 0.06 wt/wt. FIG. 18B compares mean particle diameter (nm) as a function of DLin-KC2-DMA content (mol %) for LNP prepared by the PFV and MF methods. The cationic lipid was varied from 40 mol % to 70 mol %. PEG-c-DMA was kept constant at 1 mol % and a 0.25 molar ratio was maintained with DSPC-cholesterol. Total flow rate inside microfluidic mixer was maintained at 2 ml/min. 10 mM lipid-ethanol phase mixed with 25 mM acetate buffer, pH 4, containing siRNA. Error bars represent standard deviation of the mean particle diameter as measured by dynamic light scattering.

FIG. 20A is an image of empty LNP composed of Dlin-KC2-DMA/DSPC/Cholesterol/PEG-c-DMA at mole ratios of 40:11.5:47.5:1. FIG. 20B is an image of siRNA loaded LNP composed of Dlin-KC2-DMA/DSPC/Cholesterol/PEG-c-DMA at mole ratios of 40:11.5:47.5:1, siRNA-total lipid ratio 0.06 wt/wt. Formulation was performed using the microfluidic mixer at 20 mM lipid in the ethanol phase. Loaded LNP-siRNA and empty particles containing 1 mol % PEG-c-DOMG exhibited identical morphology and are very homogeneous in structure. Scale bar represents 100 nm.

DETAILED DESCRIPTION OF THE INVENTION

Figure 1:
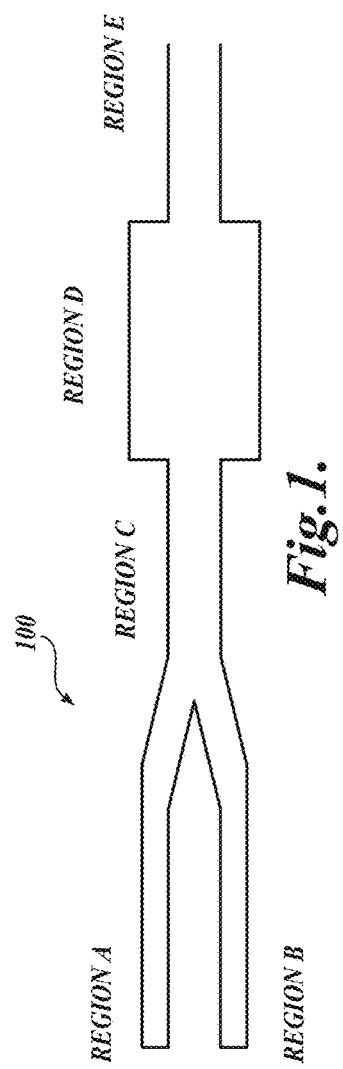
FIG. 1 is a schematic illustration of a representative fluidic device of the invention.

The present invention provides lipid particles containing a therapeutic agent, methods and devices for making the lipid particles containing a therapeutic agent, and methods for delivering a therapeutic agent using the lipid particles.

Lipid Particles

In one aspect, the invention provides lipid particles containing a therapeutic agent. The lipid particles include one or more cationic lipids, one or more second lipids, and one or more nucleic acids.

Cationic Lipid.

The lipid particles include an cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids (e.g., oligonucleotides). As used herein, the term "cationic lipid" includes zwitterionic lipids that assume a positive charge on pH decrease.

The term "cationic lipid" refers to any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl)cholesterol (DC-Chol) and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Suitable amino lipids useful in the invention include those described in WO 2009/096558, incorporated herein by reference in its entirety. Representative amino lipids include 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA•Cl), 1,2-dilinoleoyl-3-trimethylaminopropane chloride salt (DLin-TAP•Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

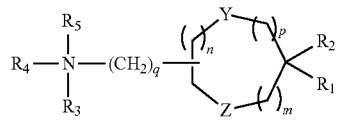

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In one embodiment, $R_1$ and $R_2$ are each linoleyl, and the amino lipid is a dilinoleyl amino lipid. In one embodiment, the amino lipid is a dilinoleyl amino lipid.

A representative useful dilinoleyl amino lipid has the formula:

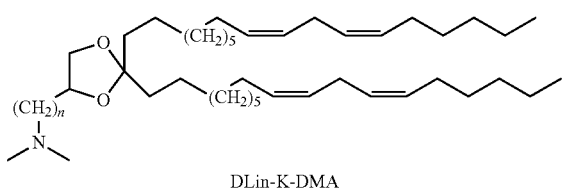

DLin-K-DMA wherein n is 0, 1, 2, 3, or 4.

In one embodiment, the cationic lipid is a DLin-K-DMA. In one embodiment, the cationic lipid is DLin-KC2-DMA (DLin-K-DMA above, wherein n is 2).

Other suitable cationic lipids include cationic lipids, which carry a net positive charge at about physiological pH, in addition to those specifically described above, N,N-dioleyl-N,N-dimethylammonium chloride (DODAC); N-(2,3-dioleyloxy)propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); 1,2-dioleyloxy-3-trimethylaminopropane chloride salt (DOTAP•Cl); 3β-(N—(N',N'-dimethylaminoethane)carbamoyl)cholesterol (DC-Chol), N-(1-(2,3-dioleoyloxy)propyl)-N-2-(sperminecarboxamido) ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

The cationic lipid is present in the lipid particle in an amount from about 30 to about 95 mole percent. In one embodiment, the cationic lipid is present in the lipid particle in an amount from about 30 to about 70 mole percent. In one embodiment, the cationic lipid is present in the lipid particle in an amount from about 40 to about 60 mole percent.

In one embodiment, the lipid particle includes ("consists of") only of one or more cationic lipids and one or more nucleic acids. The preparation and characterization of a lipid particle of the invention consisting of a cationic lipid and a nucleic acid is described in Example 5.

Second Lipids.

In certain embodiments, the lipid particles include one or more second lipids. Suitable second lipids stabilize the formation of particles during their formation.

The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

Suitable stabilizing lipids include neutral lipids and anionic lipids.

Neutral Lipid.

The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides.

Exemplary lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), and 1,2-dielaidoyl-sn-glycero-3-phophoethanolamine (transDOPE).

In one embodiment, the neutral lipid is 1,2-distearoyl-sn-glycero-3-phosphocholine (DSPC).

Anionic Lipid.

The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

Other suitable lipids include glycolipids (e.g., monosialoganglioside $GM_1$). Other suitable second lipids include sterols, such as cholesterol.

Polyethylene Glycol-Lipids.

In certain embodiments, the second lipid is a polyethylene glycol-lipid. Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG).

In certain embodiments, The second lipid is present in the lipid particle in an amount from about 1 to about 10 mole percent. In one embodiment, the second lipid is present in the lipid particle in an amount from about 1 to about 5 mole percent. In one embodiment, the second lipid is present in the lipid particle in about 1 mole percent.

Nucleic Acids.

The lipid particles of the present invention are useful for the systemic or local delivery of nucleic acids. As described herein, the nucleic acid is incorporated into the lipid particle during its formation.

As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucleotides of the present invention are 20-50 nucleotides in length. In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases. Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose. The nucleic acid that is present in a lipid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, and triplex-forming oligonucleotides.

In one embodiment, the polynucleic acid is an antisense oligonucleotide. In certain embodiments, the nucleic acid is an antisense nucleic acid, a ribozyme, tRNA, snRNA, siRNA, shRNA, ncRNA, miRNA, pre-condensed DNA, or an aptamer.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate.

The term "nucleotide," as used herein, generically encompasses the following terms, which are defined below: nucleotide base, nucleoside, nucleotide analog, and universal nucleotide.

The term "nucleotide base," as used herein, refers to a substituted or unsubstituted parent aromatic ring or rings. In some embodiments, the aromatic ring or rings contain at least one nitrogen atom. In some embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-2-isopentenyladenine (6iA), N6-2-isopentenyl-2-methylthioadenine (2ms6iA), N6-methyladenine, guanine (G), isoguanine, N2-dimethylguanine (dmG), 7-methylguanine (7mG), 2-thiopyrimidine, 6-thioguanine (6sG) hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, O4-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); In some embodiments, nucleotide bases are universal nucleotide bases. Additional exemplary nucleotide bases can be found in Fasman, 1989, *Practical Handbook of Biochemistry and Molecular Biology*, pp. 385-394, CRC Press, Boca Raton, Fla., and the references cited therein. Further examples of universal bases can be found, for example, in Loakes, *N.A.R.* 2001, 29:2437-2447 and Seela *N.A.R.* 2000, 28:3224-3232.

The term "nucleoside," as used herein, refers to a compound having a nucleotide base covalently linked to the C-1' carbon of a pentose sugar. In some embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-

C14)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose. Also see, e.g., 2'-O-methyl, 4'-α-anomeric nucleotides, 1'-α-anomeric nucleotides (Asseline (1991) Nucl. Acids Res. 19:4067-74), 2'-4'- and 3'-4'-linked and other "locked" or "LNA," bicyclic sugar modifications (WO 98/22489; WO 98/39352; WO 99/14226). "LNA" or "locked nucleic acid" is a DNA analogue that is conformationally locked such that the ribose ring is constrained by a methylene linkage between the 2'-oxygen and the 3'- or 4'-carbon. The conformation restriction imposed by the linkage often increases binding affinity for complementary sequences and increases the thermal stability of such duplexes.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g., A or G, the ribose sugar is attached to the N9-position of the nucleobase. When the nucleobase is pyrimidine, e.g., C, T or U, the pentose sugar is attached to the N1-position of the nucleobase (Kornberg and Baker, (1992) DNA Replication, 2nd Ed., Freeman, San Francisco, Calif.).

One or more of the pentose carbons of a nucleoside may be substituted with a phosphate ester. In some embodiments, the phosphate ester is attached to the 3'- or 5'-carbon of the pentose. In some embodiments, the nucleosides are those in which the nucleotide base is a purine, a 7-deazapurine, a pyrimidine, a universal nucleotide base, a specific nucleotide base, or an analog thereof.

The term "nucleotide analog," as used herein, refers to embodiments in which the pentose sugar and/or the nucleotide base and/or one or more of the phosphate esters of a nucleoside may be replaced with its respective analog. In some embodiments, exemplary pentose sugar analogs are those described above. In some embodiments, the nucleotide analogs have a nucleotide base analog as described above. In some embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, and may include associated counterions. Other nucleic acid analogs and bases include for example intercalating nucleic acids (INAs, as described in Christensen and Pedersen, 2002), and AEGIS bases (Eragen, U.S. Pat. No. 5,432,272). Additional descriptions of various nucleic acid analogs can also be found for example in (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Lett. 805 (1984), Letsinger et al., J. Am. Chem. Soc. 110:4470 (1988); and Pauwels et al., Chemica Scripta 26:141 (1986)), phosphorothioate (Mag et al., Nucleic Acids Res. 19:1437 (1991); and U.S. Pat. No. 5,644,048. Other nucleic analogs comprise phosphorodithioates (Briu et al., J. Am. Chem. Soc. 111:2321 (1989)), O-methylphophoroamidite linkages (see Eckstein, Oligonucleotides and Analogues: A Practical Approach, Oxford University Press), those with positive backbones (Denpcy et al., Proc. Natl. Acad. Sci. USA 92:6097 (1995); non-ionic backbones (U.S. Pat. Nos. 5,386,023; 5,386,023; 5,637,684; 5,602,240; 5,216,141; and U.S. Pat. No. 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (194): Chapters 2 and 3, ASC Symposium Series 580, "Carbohydrate Modifications in Antisense Research," Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins et al., Chem. Soc. Rev. (1995) pp. 169-176). Several nucleic acid analogs are also described in Rawls, C & E News Jun. 2, 1997, page 35.

The term "universal nucleotide base" or "universal base," as used herein, refers to an aromatic ring moiety, which may or may not contain nitrogen atoms. In some embodiments, a universal base may be covalently attached to the C-1' carbon of a pentose sugar to make a universal nucleotide. In some embodiments, a universal nucleotide base does not hydrogen bond specifically with another nucleotide base. In some embodiments, a universal nucleotide base hydrogen bonds with nucleotide base, up to and including all nucleotide bases in a particular target polynucleotide. In some embodiments, a nucleotide base may interact with adjacent nucleotide bases on the same nucleic acid strand by hydrophobic stacking. Universal nucleotides include, but are not limited to, deoxy-7-azaindole triphosphate (d7AITP), deoxyisocarbostyril triphosphate (dICSTP), deoxypropynylisocarbostyril triphosphate (dPICSTP), deoxymethyl-7-azaindole triphosphate (dM7AITP), deoxyImPy triphosphate (dImPyTP), deoxyPP triphosphate (dPPTP), or deoxypropynyl-7-azaindole triphosphate (dP7AITP). Further examples of such universal bases can be found, inter alia, in Published U.S. application Ser. No. 10/290,672, and U.S. Pat. No. 6,433,134.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric mixtures thereof. Polynucleotides may be comprised of internucleotide, nucleobase and/or sugar analogs. Polynucleotides typically range in size from a few monomeric units, e.g., 3-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, and "T" denotes thymidine, unless otherwise noted.

As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

As used herein, "nucleobase sequence" means any segment, or aggregate of two or more segments (e.g. the aggregate nucleobase sequence of two or more oligomer blocks), of a polymer that comprises nucleobase-containing subunits. Non-limiting examples of suitable polymers or polymers segments include oligodeoxynucleotides (e.g. DNA), oligoribonucleotides (e.g. RNA), peptide nucleic acids (PNA), PNA chimeras, PNA combination oligomers, nucleic acid analogs and/or nucleic acid mimics.

As used herein, "polynucleobase strand" means a complete single polymer strand comprising nucleobase subunits. For example, a single nucleic acid strand of a double stranded nucleic acid is a polynucleobase strand.

As used herein, "nucleic acid" is a nucleobase sequence-containing polymer, or polymer segment, having a backbone formed from nucleotides, or analogs thereof.

Preferred nucleic acids are DNA and RNA.

As used herein, nucleic acids may also refer to "peptide nucleic acid" or "PNA" means any oligomer or polymer segment (e.g., block oligomer) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082; 5,527,675; 5,623,049; 5,714,331; 5,718,262; 5,736,336; 5,773,571; 5,766,855; 5,786,461; 5,837,459; 5,891,625; 5,972,610; 5,986,053; and 6,107,470; all of which are herein incorporated by reference. The term "peptide nucleic acid" or "PNA" shall also apply to any oligomer or polymer segment comprising two or more subunits of those nucleic acid mimics described in the following publications: Lagriffoul et al., *Bioorganic & Medicinal Chemistry Letters*, 4:1081-1082 (1994); Petersen et al., *Bioorganic & Medicinal Chemistry Letters*, 6:793-796 (1996); Diderichsen et al., *Tett. Lett.* 37:475-478 (1996); Fujii et al., *Bioorg. Med. Chem. Lett.* 7:637-627 (1997); Jordan et al., *Bioorg. Med. Chem. Lett.* 7:687-690 (1997); Krotz et al., *Tett. Lett.* 36:6941-6944 (1995); Lagriffoul et al., *Bioorg. Med. Chem. Lett.* 4:1081-1082 (1994); Diederichsen, U., *Bioorganic & Medicinal Chemistry Letters*, 7:1743-1746 (1997); Lowe et al., *J. Chem. Soc. Perkin Trans.* 1, (1997) 1:539-546; Lowe et al., *J. Chem. Soc. Perkin Trans.* 11:547-554 (1997); Lowe et al., *J. Chem. Soc. Perkin Trans.* 11:555-560 (1997); Howarth et al., *J. Org. Chem.* 62:5441-5450 (1997); Altmann, K-H et al., *Bioorganic & Medicinal Chemistry Letters*, 7:1119-1122 (1997); Diederichsen, U., *Bioorganic & Med. Chem. Lett.*, 8:165-168 (1998); Diederichsen et al., *Angew. Chem. Int. Ed.*, 37:302-305 (1998); Cantin et al., *Tett. Lett.*, 38:4211-4214 (1997); Ciapetti et al., *Tetrahedron*, 53:1167-1176 (1997); Lagriffoule et al., *Chem. Eur. J.*, 3:912-919 (1997); Kumar et al., *Organic Letters* 3(9):1269-1272 (2001); and the Peptide-Based Nucleic Acid Mimics (PENAMS) of Shah et al. as disclosed in WO96/04000.

Lipid Particle Characteristics

Morphology.

The lipid particle of the invention differs from other similarly constituted materials by its morphology and characterized as having a substantially solid core. A lipid particle having a substantially solid core is a particle that does not have extended aqueous regions on the interior and that has an interior that is primarily lipid. In one embodiment, an extended region is a continuous aqueous region with a volume greater than half the particle volume. In a second embodiment, an extended aqueous region is more than 25% of the particle volume. The extent of internal aqueous regions may be determined by electron microscopy and appear as regions of low electron density. Further, because the interior of the solid core nanoparticle is primarily lipid, the aqueous content of the particle (the "trapped volume") per lipid constituting the particle is less than that expected for a unilamellar bilayer lipid vesicle with the same radius. In one embodiment, the trapped volume is less than 50% of that expected for a unilamellar bilayer vesicle with the same radius. In a second embodiment, the trapped volume is less than 25% of that expected for a unilamellar bilayer vesicle of the same size. In a third embodiment, the trapped volume is less than 20% of the total volume of the particle. In one embodiment, the trapped volume per lipid is less than 2 microliter per micromole lipid. In another embodiment the trapped volume is less than 1 microliter per micromole lipid. In addition, while the trapped volume per lipid increases substantially for a bilayer lipid vesicle as the radius of the vesicle is increased, the trapped volume per lipid does not increase substantially as the radius of solid core nanoparticles is increased. In one embodiment, the trapped volume per lipid increases by less than 50% as the mean size is increased from a diameter of 20 nm to a diameter of 100 nm. In a second embodiment, the trapped volume per lipid increases by less than 25% as the mean size is increased from a diameter of 20 nm to a diameter of 100 nm. The trapped volume can be measured employing a variety of techniques described in the literature. Because solid core systems contain lipid inside the particle, the total number of particles of a given radius generated per mole of lipid is less than expected for bilayer vesicle systems. The number of particles generated per mol of lipid can be measured by fluorescence techniques amongst others.

The lipid particles of the invention can also be characterized by electron microscopy. The particles of the invention having a substantially solid core have an electron dense core as seen by electron microscopy. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

Particle Size.

The lipid particle of the invention has a diameter (mean particle diameter) from about 15 to about 300 nm. In some embodiments, the lipid particle has a diameter of about 300 nm or less, 250 nm or less, 200 nm or less, 150 nm or less, 100 nm or less, or 50 nm or less. In one embodiment, the lipid particle has a diameter from about 15 to about 100 nm.

These particles generally exhibit increased circulatory lifetime in vivo compared to large particles. In one embodiment, the lipid particle has a diameter from about 15 to about 50 nm. These particles are capable of advantageously escaping the vascular system. In one embodiment, the lipid particle has a diameter from about 15 to about 20 nm. These particles near the limit size for particles that contain a nucleic acid; such particles may include a single polynucleotide (e.g., siRNA).

The lipid particles of the invention are substantially homogeneous in their size distribution. In certain embodiments, the lipid particles of the invention have a mean particle diameter standard deviation of from about 65 to about 25%. In one embodiment, the lipid particles of the invention have a mean particle diameter standard deviation of about 60, 50, 40, 35, or 30%.

Encapsulation Efficiency.

The lipid particles of the invention can be further distinguished by the encapsulation efficiency. As described below, the lipid particles of the invention are prepared by a process by which nearly 100% of the nucleic acid used in the formation process is encapsulated in the particles. In one embodiment, the lipid particles are prepared by a process by which from about 90 to about 95% of the nucleic acid used in the formation process is encapsulated in the particles.

Microfluidic Methods for Making Lipid Particles

In one aspect, the invention provides a method for making lipid particles containing a therapeutic agent. In one embodiment, the method includes (a) introducing a first stream comprising a therapeutic agent (e.g., polynucleic acid) in a first solvent into a microchannel; wherein the microchannel has a first region adapted for flowing one or more streams introduced into the microchannel and a second region for mixing the contents of the one or more streams;

(b) introducing a second stream comprising lipid particle-forming materials in a second solvent in the microchannel to provide first and second streams flowing under laminar flow conditions, wherein the lipid particle-forming materials comprise an ionizable lipid, and wherein the first and second solvents are not the same;

(c) flowing the one or more first streams and the one or more second streams from the first region of the microchannel into the second region of the microchannel; and (d) mixing of the contents of the one or more first streams and the one or more second streams flowing under laminar flow conditions in the second region of the microchannel to provide a third stream comprising lipid particles with encapsulated therapeutic agents.

The contents of the first and second streams can be mixed by chaotic advection. In one embodiment, mixing the contents of the one or more first streams and the one or more second streams comprises varying the concentration or relative mixing rates of the one or more first streams and the one or more second streams. In the above embodiment, unlike known methods, the method does not include a dilution after mixing.

To further stabilize the third stream containing the lipid particles with encapsulated therapeutic agents, the method can, but need not further include, comprising diluting the third stream with an aqueous buffer. In one embodiment, diluting the third stream includes flowing the third stream and an aqueous buffer into a second mixing structure. In another embodiment, the aqueous buffer comprising lipid particles with encapsulated therapeutic agents is dialyzed to reduce the amount of the second solvent.

The first stream includes a therapeutic agent in a first solvent. Suitable first solvents include solvents in which the therapeutic agents are soluble and that are miscible with the second solvent. Suitable first solvents include aqueous buffers. Representative first solvents include citrate and acetate buffers.

The second stream includes lipid particle-forming materials in a second solvent. Suitable second solvents include solvents in which the ionizable lipids are soluble and that are miscible with the first solvent. Suitable second solvents include 1,4-dioxane, tetrahydrofuran, acetone, acetonitrile, dimethyl sulfoxide, dimethylformamide, acids, and alcohols. Representative second solvents include aqueous ethanol 90%.

The methods of the invention are distinguished from other microfluidic mixing methods in several ways. Whereas certain known methods require an equal or substantially equal proportion of aqueous and organic solvents (i.e., 1:1), the method of the invention generally utilizes a solvent ratio of aqueous to organic that exceeds 1:1. In certain embodiments, the solvent ratio of aqueous to organic is about 2:1. In certain embodiments, the solvent ratio of aqueous to organic is about 3:1. In certain embodiments, the solvent ratio of aqueous to organic is about 4:1. In certain other embodiments, the solvent ratio of aqueous to organic is about 5:1, about 10:1, about 50:1, about 100:1, or greater.

The lipid particles of the invention are advantageously formed in a microfluidic process that utilizes relatively rapid mixing and high flow rates. The rapid mixing provide lipid particles having the advantageous properties noted above including size, homogeneity, encapsulation efficiency. Mixing rates used in the practice of the method of the invention range from about 100 μsec to about 10 msec. Representative mixing rates include from about 1 to about 5 msec. Whereas hydrodynamic flow focusing methods operate at relatively low flow rates (e.g., 5 to 100 μL/minute) with relatively low lipid volumes, the method of the invention operates at relatively high flow rates and relatively high lipid volumes. In certain embodiments, for methods that incorporate a single mixing region (i.e., mixer), the flow rate is about 1 mL/min. For methods of the invention that utilize mixer arrays (e.g., 10 mixers), flow rates of 40 mL/minute are employed (for 100 mixers, flow rate 400 mL/min). Thus, the methods of the invention can be readily scaled to provide quantities of lipid particles necessary for demanding production requirements. Coupled with the advantageous particle size and homogeneity and encapsulation efficiencies realized, the method of the invention overcomes disadvantages of known microfluidic methods for producing the lipid particles. One advantage of the methods of the invention for making the lipid particles is that the methods are scalable, which means that the methods do not change on scaling and that there is excellent correspondence on scaling.

Microfluidic Devices for Making Lipid Particles

In another aspect, the invention provide devices for producing a lipid particle encapsulating a nucleic acid. In one embodiment the device includes:

(a) a first inlet for receiving a first solution comprising a nucleic acid in a first solvent;

(b) a first inlet microchannel in fluid communication with the first inlet to provide a first stream comprising the nucleic acid in the first solvent;

(c) a second inlet for receiving a second solution comprising lipid particle-forming materials in a second solvent;

(d) a second inlet microchannel in fluid communication with the second inlet to provide a second stream comprising the lipid particle-forming materials in the second solvent;

(e) a third microchannel for receiving the first and second streams, wherein the third microchannel has a first region adapted for flowing the first and second streams introduced into the microchannel under laminar flow conditions and a second region adapted for mixing the contents of the first and second streams to provide a third stream comprising lipid particles with encapsulated nucleic acid.

In one embodiment, the device further includes means for diluting the third stream to provide a diluted stream comprising stabilized lipid particles with encapsulated therapeutic agent.

The device of the invention is a microfluidic device including one or more microchannels (i.e., a channel having its greatest dimension less than 1 millimeter). In one embodiment, the microchannel has a hydrodynamic diameter from about 20 to about 300 µm. As noted above, the microchannel has two regions: a first region for receiving and flowing at least two streams (e.g., one or more first streams and one or more second streams) under laminar flow conditions. The contents of the first and second streams are mixed in the microchannel's second region. In one embodiment, the second region of the microchannel has a principal flow direction and one or more surfaces having at least one groove or protrusion defined therein, the groove or protrusion having an orientation that forms an angle with the principal direction (e.g., a staggered herringbone mixer), as described in U.S. Application Publication No. 2004/0262223, expressly incorporated herein by reference in its entirety. In one embodiment, the second region of the microchannel comprises bas-relief structures. To achieve maximal mixing rates, it is advantageous to avoid undue fluidic resistance prior to the mixing region. Thus, one embodiment of the invention is a device in which non-microfluidic channels, having dimensions greater than 1000 microns, are used to deliver the fluids to a single mixing channel.

In other aspects of the invention, the first and second streams are mixed with other micromixers. Suitable micromixers include droplet mixers, T-mixers, zigzag mixers, multilaminate mixers, or other active mixers.

Mixing of the first and second streams can also be accomplished with means for varying the concentration and relative flow rates of the first and second streams.

In another embodiment, the device for producing a lipid particle encapsulating a nucleic acid includes microchannel for receiving the first and second streams, wherein the microchannel has a first region adapted for flowing the first and second streams introduced into the microchannel under laminar flow conditions and a second region adapted for mixing the contents of the first and second streams to provide a third stream comprising lipid particles with encapsulated therapeutic agent. In this embodiment, the first and second stream are introduced into the microchannel by means other than first and second microchannels as noted above.

To achieve maximal mixing rates it is advantageous to avoid undue fluidic resistance prior to the mixing region. Thus one embodiment of the invention is a device in which non-microfluidic channels, having dimensions greater than 1000 microns, are used to deliver fluids to a single mixing channel. This device for producing a lipid particle encapsulating a nucleic acid includes:

(a) a single inlet microchannel for receiving both a first solution comprising a nucleic acid in a first solvent and a second solution comprising lipid particle-forming materials in a second solvent;

(b) a second region adapted for mixing the contents of the first and second streams to provide a third stream comprising lipid particles with encapsulated nucleic acid.

In such an embodiment, the first and second streams are introduced into the microchannel by a single inlet or by one or two channels not having micro-dimensions, for example, a channel or channels having dimensions greater than 1000 µm (e.g., 1500 or 2000 µm or larger). These channels may be introduced to the inlet microchannel using adjacent or concentric macrosized channels.

FIG. 1 is a schematic illustration of a representative fluidic device of the invention. Referring to FIG. 1, device 100 includes Region A for receiving a first stream comprising a therapeutic agent in a first solvent and Region B for receiving a stream comprising lipid particle-forming materials in a second solvent. First and second streams are introduced into Region C flowing under laminal flow conditions, to Region D where rapid mixing occurs, and then to Region E where the final product, lipid particles containing therapeutic agent, exit the device.

Figure 2:
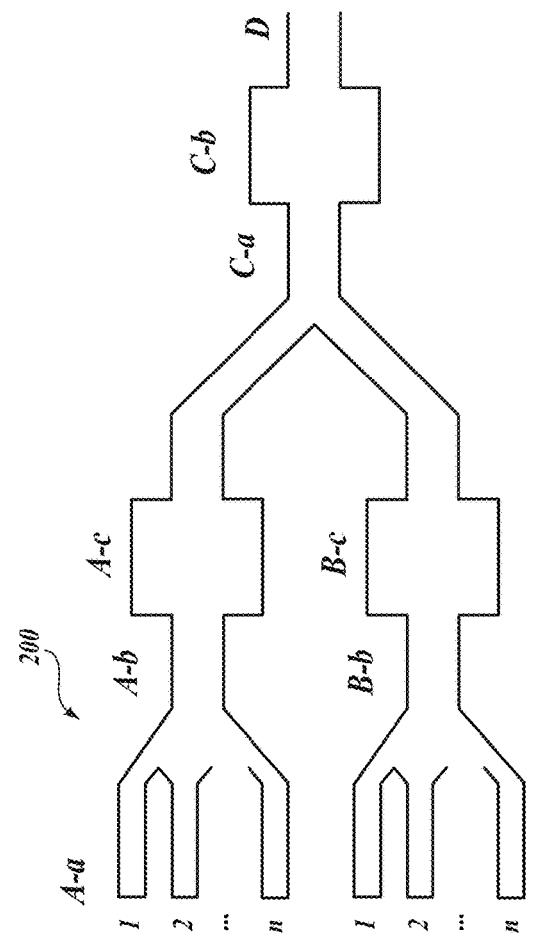
FIG. 2 is a schematic illustration of a representative fluidic device of the invention that is an elaboration of the device illustrated in FIG. 1.
Figure 3:
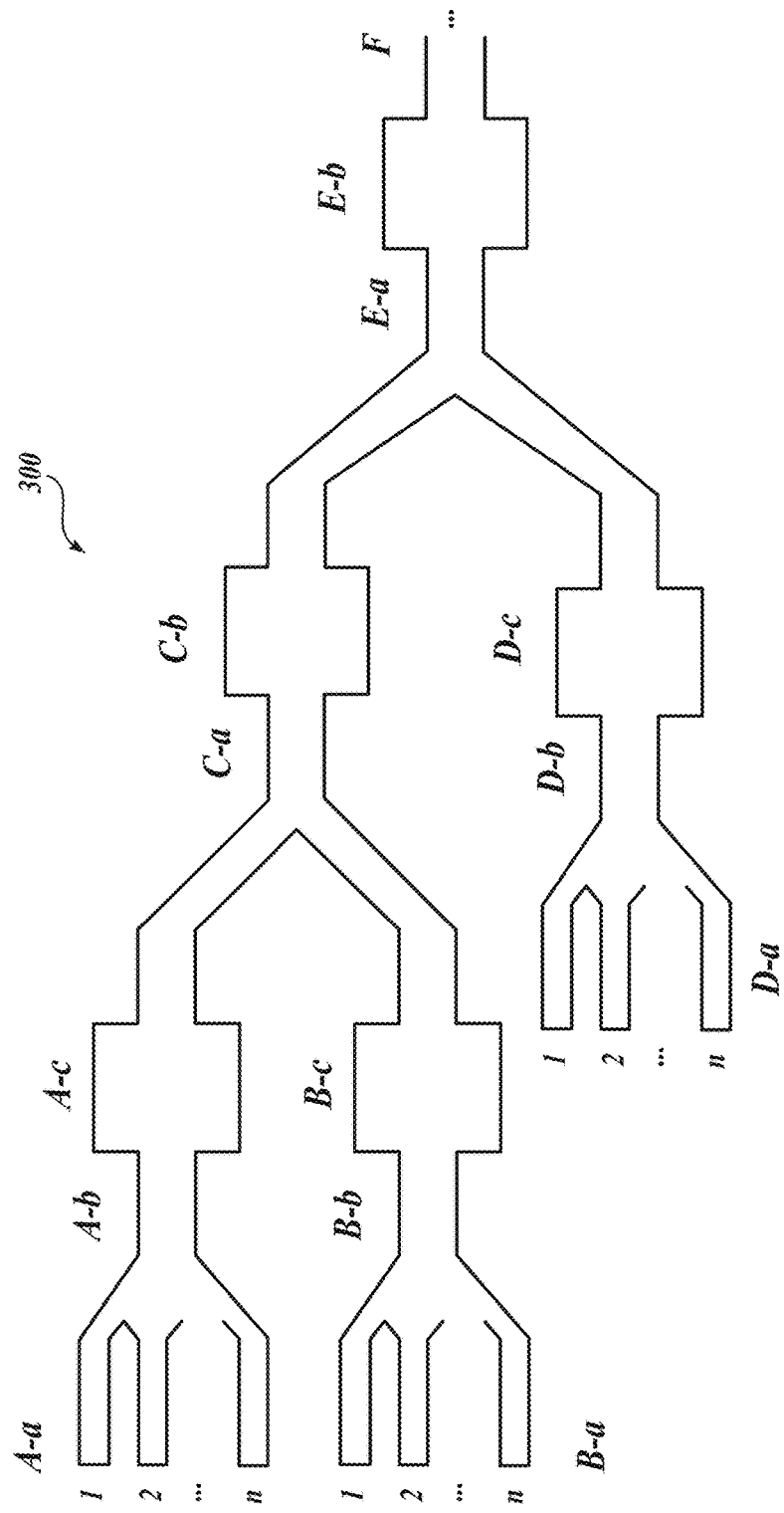
FIG. 3 is a schematic illustration of a representative fluidic device of the invention that is an elaboration of the device illustrated in FIG. 2.

FIG. 2 is a schematic illustration of a representative fluidic device of the invention that is an elaboration of the device and method illustrates in FIG. 1. Referring to FIG. 2, device 200 includes Region A for receiving a first stream comprising a therapeutic agent in a first solvent into a microchannel, wherein the microchannel has a first region adapted for flowing one or more streams (A-a) are introduced (A-b) and mixed (A-c); Region B for receiving a second stream comprising lipid particle-forming materials in a second solvent, wherein the microchannel has a first region adapted for flowing one or more streams (B-a) are introduced (B-b) and mixed (B-c); Region C introduces the flows of Region A and Region B under laminal flow conditions (C-a) and rapidly mixed (C-b); and Region D, where the formulation is ready for further processing such as dilution, pH adjustment, or other events required for nanoparticle synthesis, or where the final product, lipid particles containing therapeutic agent, exit the device FIG. 3 is a schematic illustration of a representative fluidic device of the invention that is an elaboration of the device and method illustrated in FIG. 2. Referring to FIG. 3, device 300 includes Region A for receiving a first stream comprising a therapeutic agent in a first solvent into a microchannel, wherein the microchannel has a first region adapted for flowing one or more streams (A-a) are introduced (A-b) and mixed (A-c); Region B for receiving a second stream comprising lipid particle-forming materials in a second solvent, wherein the microchannel has a first region adapted for flowing one or more streams (B-a) are introduced (B-b) and mixed (B-c); Region C introduces the flows of Region A and Region B under laminal flow conditions (C-a) and rapidly mixed (C-b); Region D for receiving a third stream comprising of any number of materials including further particle-forming materials, dilution, pH adjustments, or other events required for nanoparticle synthesis; Region E introduces the flows of Region C and Region D under laminal flow conditions (E-a) and rapidly mixed (E-b); Region F, where the formulation is ready for further processing like dilution, pH adjustments, or other events required for nanoparticle synthesis, or where the final product, lipid particles containing therapeutic agent, exit the device.

Figure 4:
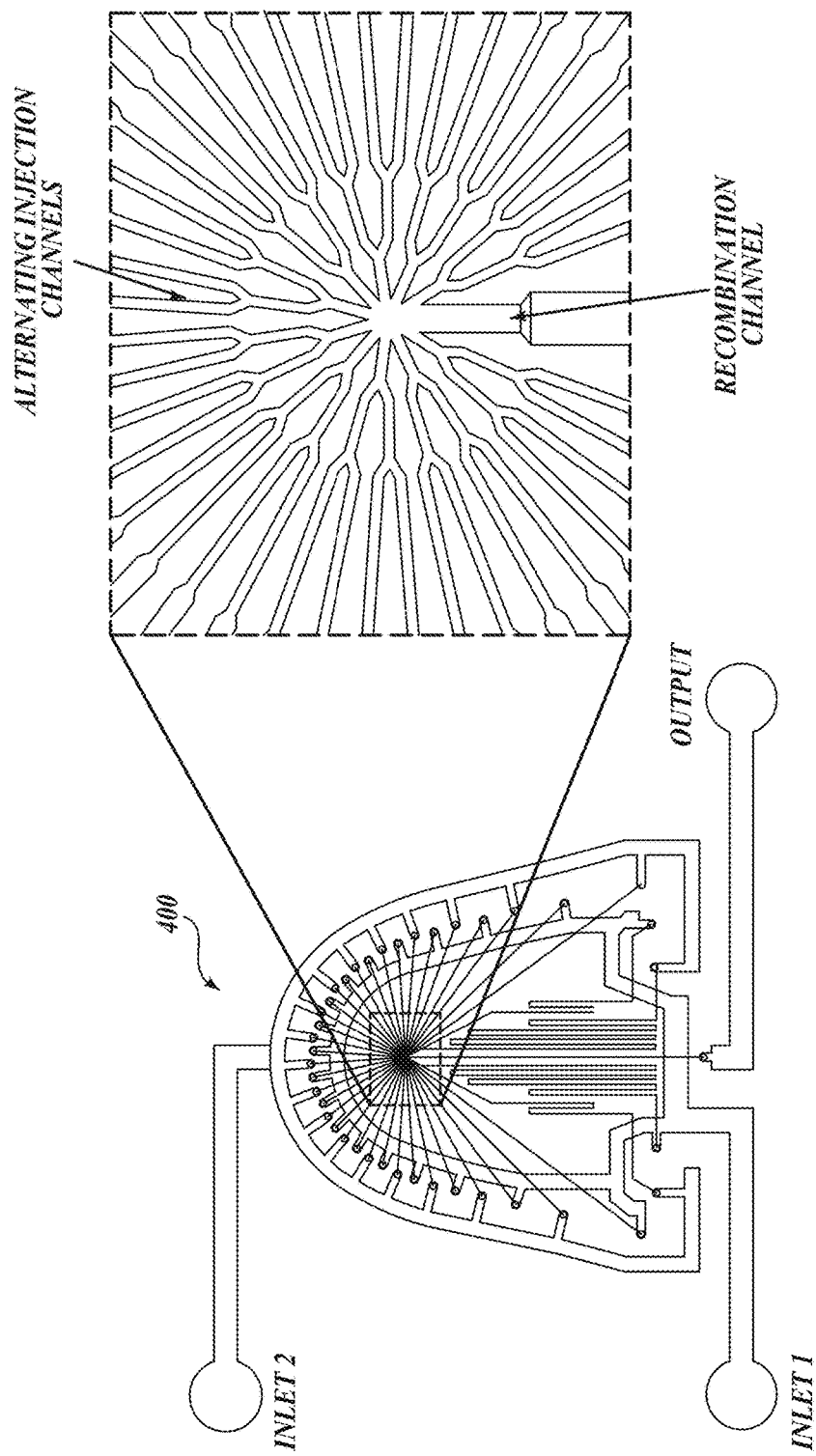
FIG. 4 is a schematic illustration of a representative fluidic device and method of the invention.
Figure 5:
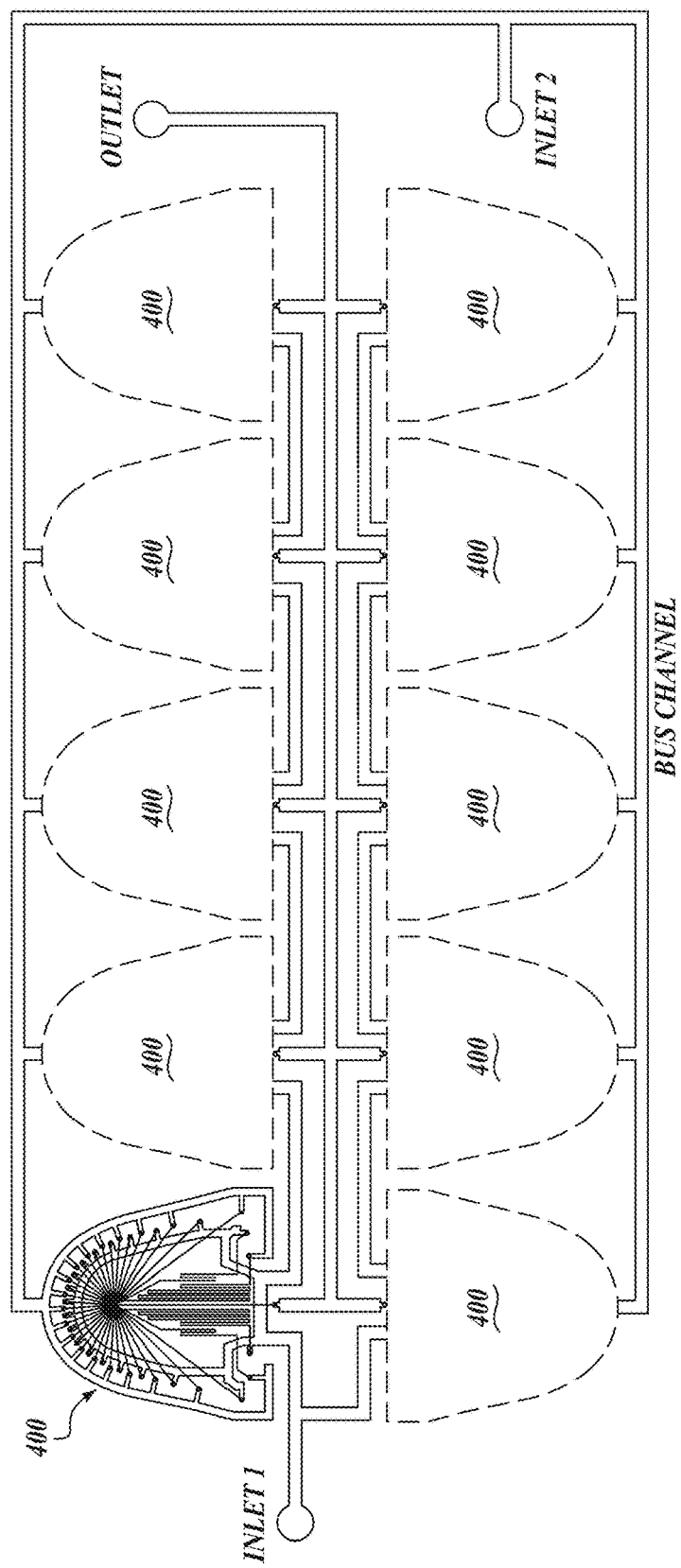
FIG. 5 is a schematic illustration of a representative array of the invention comprising ten of the fluidic devices illustrated in FIG. 4.

FIG. 4 is a schematic illustration of another representative fluidic device (400) of the invention. FIG. 5 is a schematic illustration of a representative array of the representative fluidic device illustrated in FIG. 4.

Figure 6:
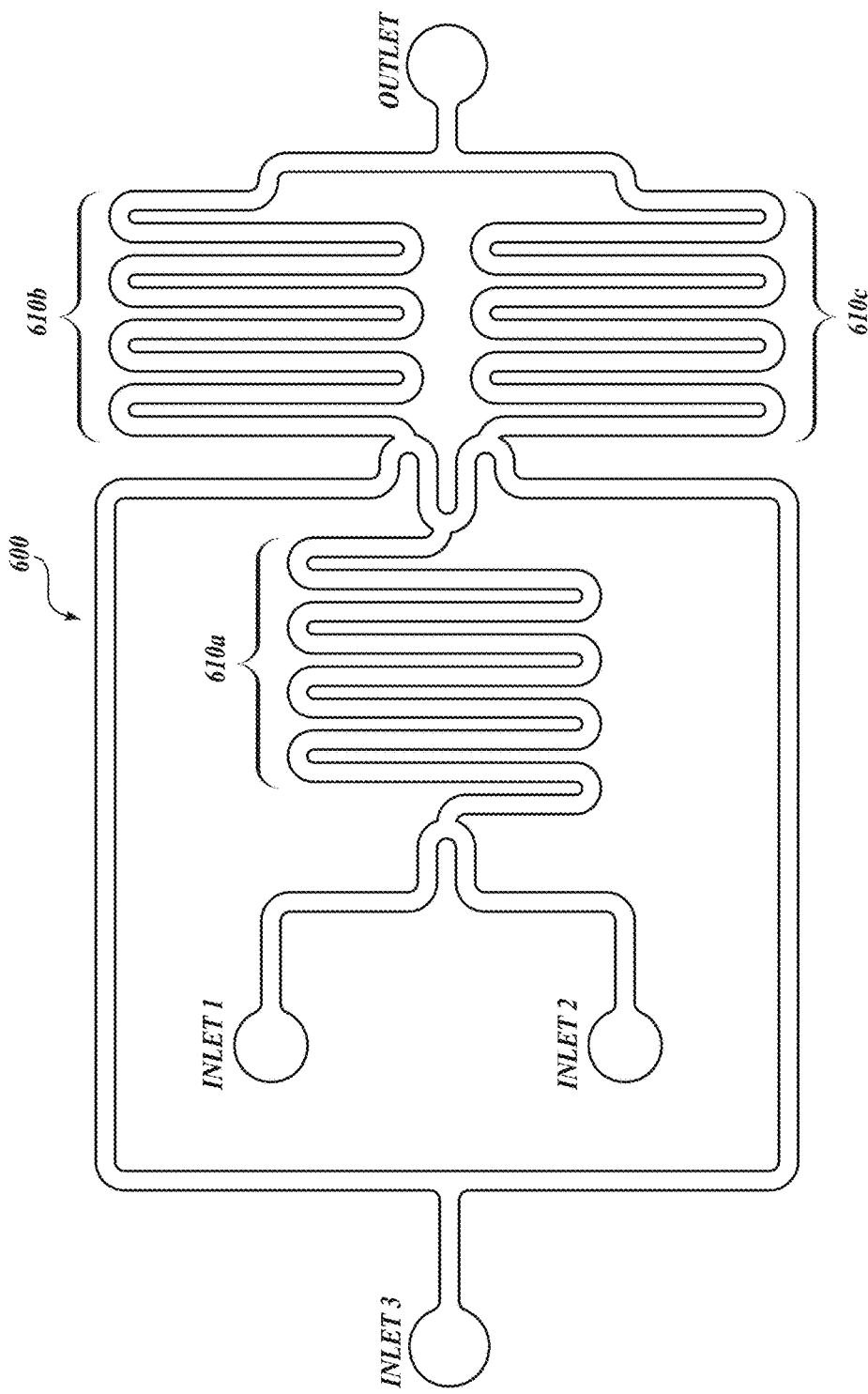
FIG. 6 is a schematic illustration of a representative fluidic device of the invention.
Figure 7:
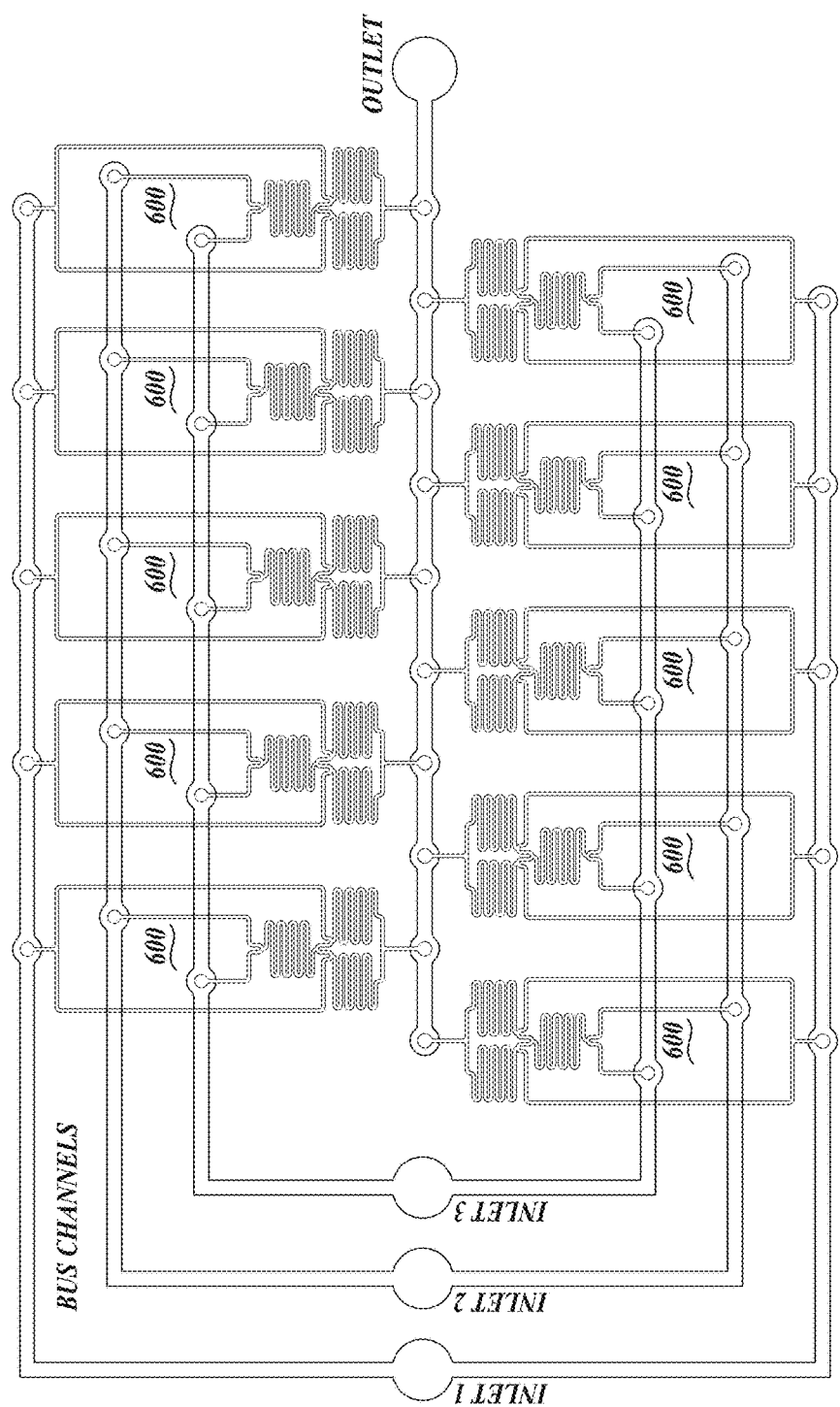
FIG. 7 is a schematic illustration of a representative array of the invention comprising ten of the representative fluidic devices illustrated in FIG. 6.

FIG. 6 is a schematic illustration of another representative fluidic device (600) of the invention. Referring to FIG. 6, device 600 includes mixing channels 610a, 610b, and 610c. FIG. 7 is a schematic illustration of a representative array of the representative fluidic device illustrated in FIG. 6.

The formation of nanoparticles on microfluidic devices is limited by the reagent volumes that participate in the mixing event and the limited backpressure that devices can withstand before leakage occurs. Single elements of the herringbone or multilaminate mixer achieve a 100-1000 fold increase in flow rate compared to droplet or flow focusing approaches. In order to achieve production scale throughput, multiple mixer elements can be arrayed. In one embodiment each reagent is distributed to the individual mixer elements using a low impedance bus channel. If the impedance of the bus channel is negligible compared to the impedance of the mixer element, the individual flow rates at the inlet of each mixer are identical. As multiple mixer elements are operated in parallel, the impedance of the system decreases resulting in a higher volumetric throughput.

This has the advantage that the mixing characteristics that are observed using a single mixer element can be maintained in a mixer array. In one embodiment, mixing in each mixer array element is achieved by introducing multiple streams into a microchannel. In this case the streams will mix by diffusion. The width of the streamlines may be varied by controlling the relative flow rates through the injection channels (e.g., by adjusting the dimensions of these channels (FIG. 5). In another embodiment, mixing is achieved by chaotic advection (staggered herringbone mixer, SHM). As shown in FIG. 7, each mixer element of the array may consist of a series of mixers. By adding elements to each array subset additional functionalities can be integrated in-line on the microfluidic device. Such functionalities may include on-chip dilution, dialysis, pH adjustments or other events that require interlaced streamlines, streams sharing the same channel or streams that are separated from each other by a porous material. In one embodiment, 10 mM POPC is dissolved in 100% ethanol and mixed with phosphate buffered saline (PBS), pH 7.4 in the first mixer element of each array subset. The LNPs that are formed after mixing are stabilized by diluting the mixture by a factor of 2 with PBS.

Table 1 compares the size distribution of particles formed on a single mixer and a mixer array consisting of ten individual mixers. The total flow rate through a single mixer may be 4 ml/min with a mixing ratio of 50:50 at each intersection. The volumetric throughput can be increased ten-fold by operating ten mixers in parallel resulting in a total volumetric flow rate of 40 ml/min. While the throughput of the array is amenable to production scale synthesis, LNP dimensions are maintained.

TABLE 1

Size distribution of particles formed on a single mixer and a mixer array consisting of ten individual mixers.

|  | Diameter (nm) | Std. Deviation (nm) | Chi squared |
| --- | --- | --- | --- |
| Single Mixer | | | |
| Intensity | 73.0 | 37.8 | 1.58 |
| Volume | 62.8 | 32.5 | |
| Number | 25.7 | 13.3 | |
| Mixer Array | | | |
| Intensity | 72.1 | 35.1 | 1.08 |
| Volume | 62.7 | 32.4 | |
| Number | 27.0 | 13.7 | |

Figure 8:
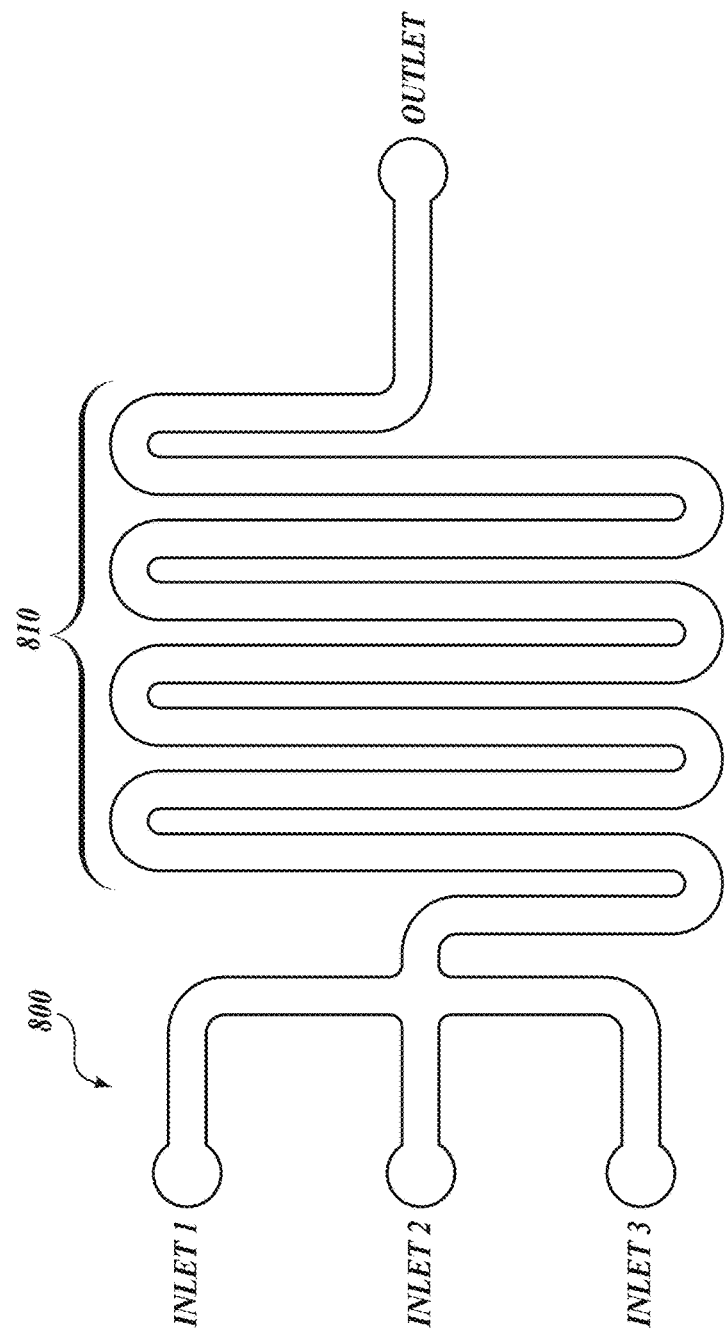
FIG. 8 is a schematic illustration of a representative fluidic device of the invention having three inlets and a single outlet (device 800 includes mixing channel 810).
Figure 9:
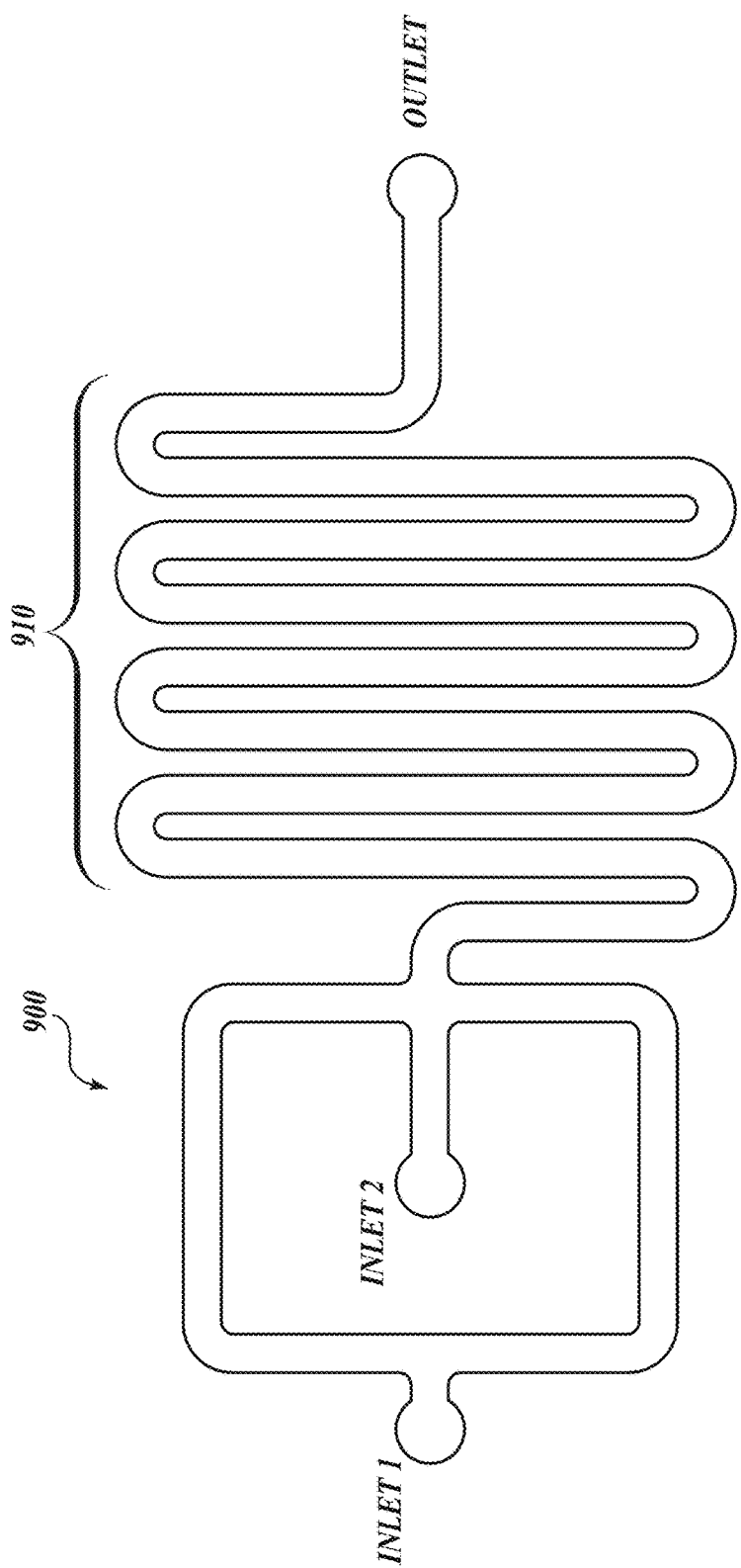
FIG. 9 is a schematic illustration of a representative fluidic device of the invention having two inlets and a single outlet (device 900 includes mixing channel 910).
Figure 10:
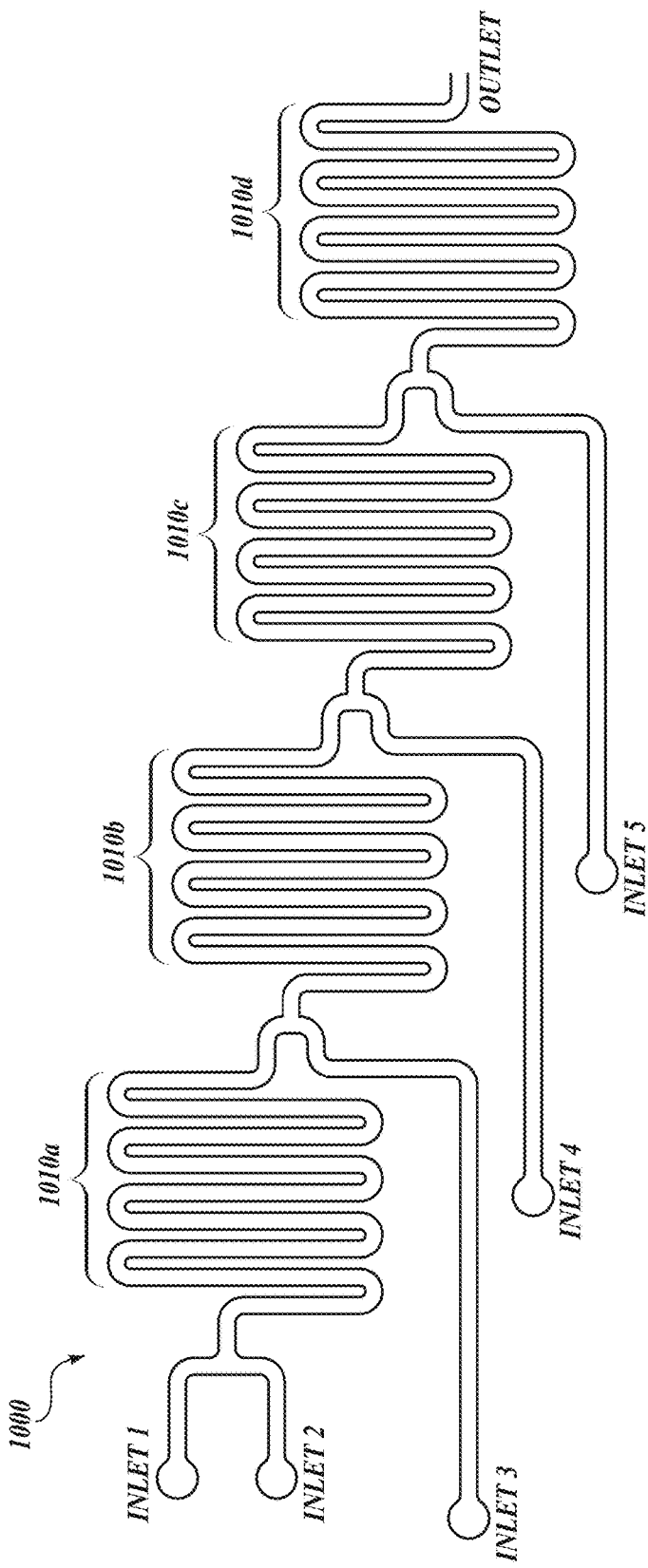
FIG. 10 is a schematic illustration of a representative fluidic device of the invention having a multiplicity (n) of serial inlets and a single outlet (device 1000 includes mixing channels 1010a, 1010b, 1010c, and 1010d).
Figure 11:
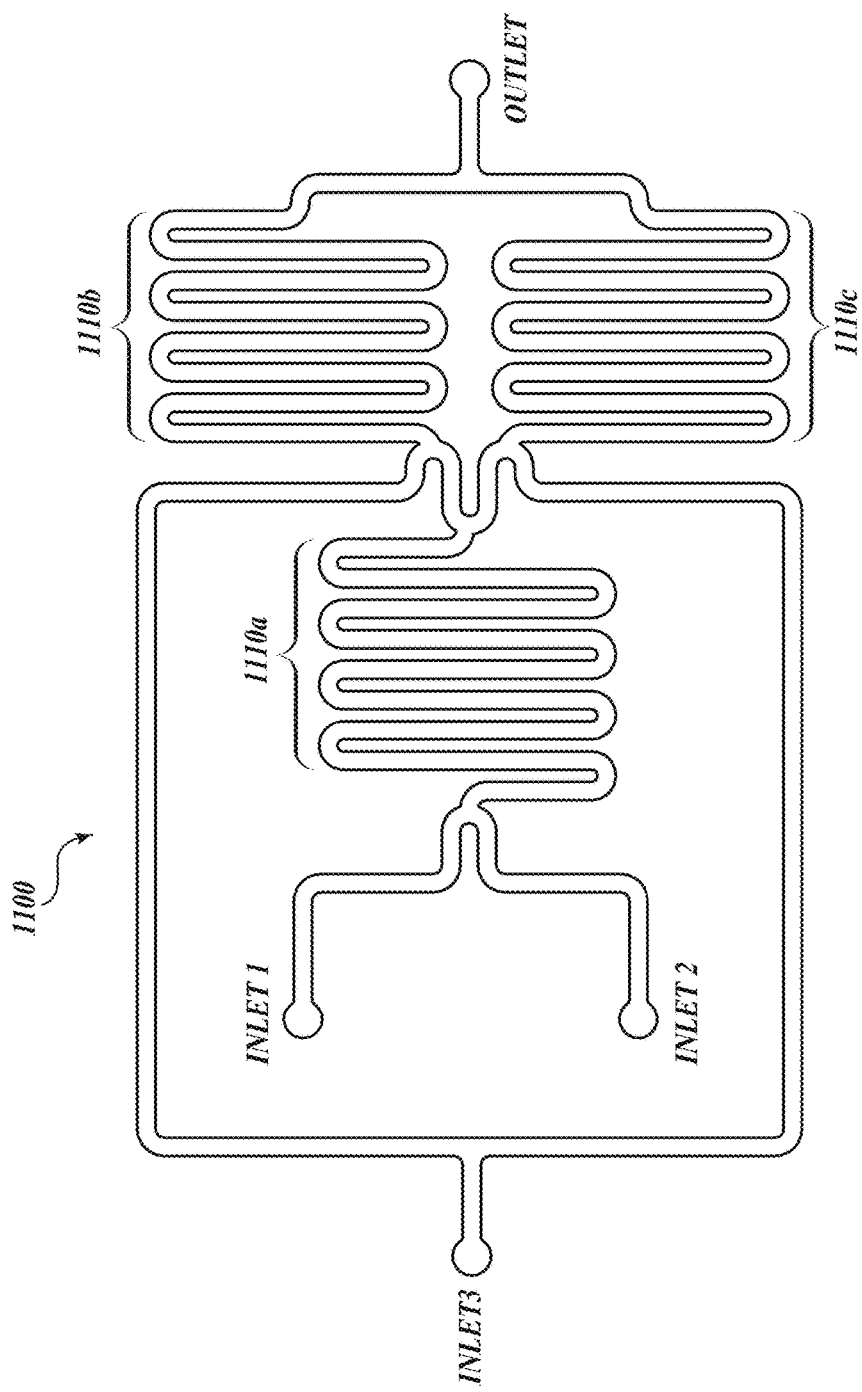
FIG. 11 is a schematic illustration of a representative fluidic device of the invention having three inlets and a single outlet (device 1100 includes mixing channels 1110a, 1110b, and 1110c).
Figure 12:
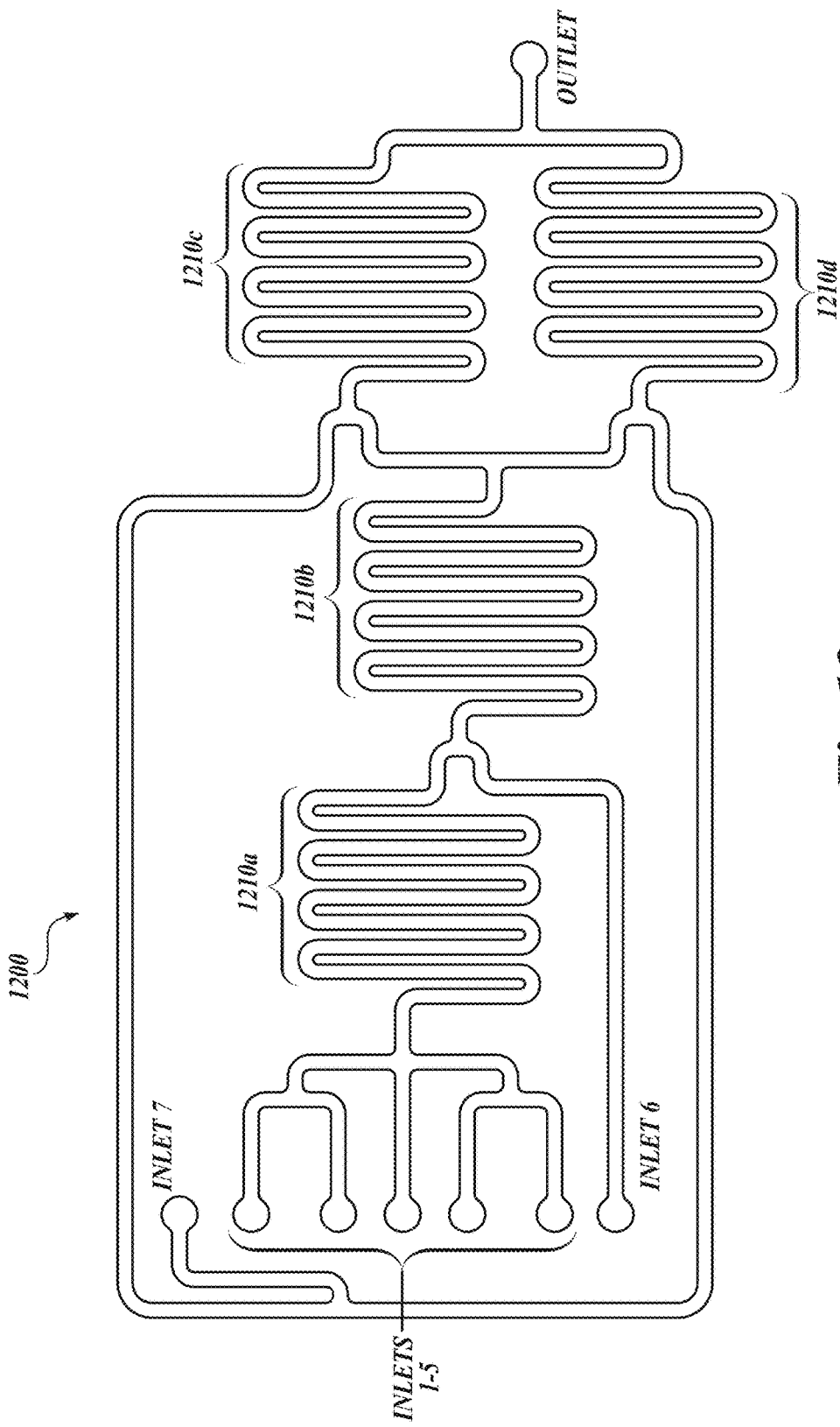
FIG. 12 is a schematic illustration of a representative fluidic device of the invention having seven inlets and a single outlet (device 1200 includes mixing channels 1210a, 1210b, 1210c, and 1210d).

Any combination of any number of parallel reagent inlets, sequential mixing chambers, and branching architectures can be used to optimize the nanoparticle formulation process. This has the advantage that different formulation process can be precisely controlled and multiple steps of the nanoparticle formulation process can be integrated. Examples include, but are not limited to, the following: (a) the introduction of two or more inlets consisting of combinations of distinct (FIG. 8) or the same (FIG. 9) reagents to allow for the independent input control (uses include independent control of the flow rates of the input reagents, varying the ratios between input reagents, and others; (b) two or more mixers in sequence to allow for the sequential addition of nanoparticle reagents or formulation processing steps (FIG. 10) (uses include the addition of input reagents in sequence for the controlled bottom up assembly of nanoparticles, the integration of formulation processes like dilution, pH adjustments, or other events required for nanoparticle synthesis, and others; or (c) any combination of inputs, mixing chambers, and branching architectures, FIG. 11 and FIG. 12 illustrate two step and three step mixers with a varying number of parallel reagent inputs and branching microfluidic structures (uses include the integration of multiple steps of the formulation process that includes on chip mixing of nanoparticle reagents, nanoparticle nucleation and growth, on-chip dilution, dialysis, pH adjustments or other events required for nanoparticle synthesis.

Figure 13:
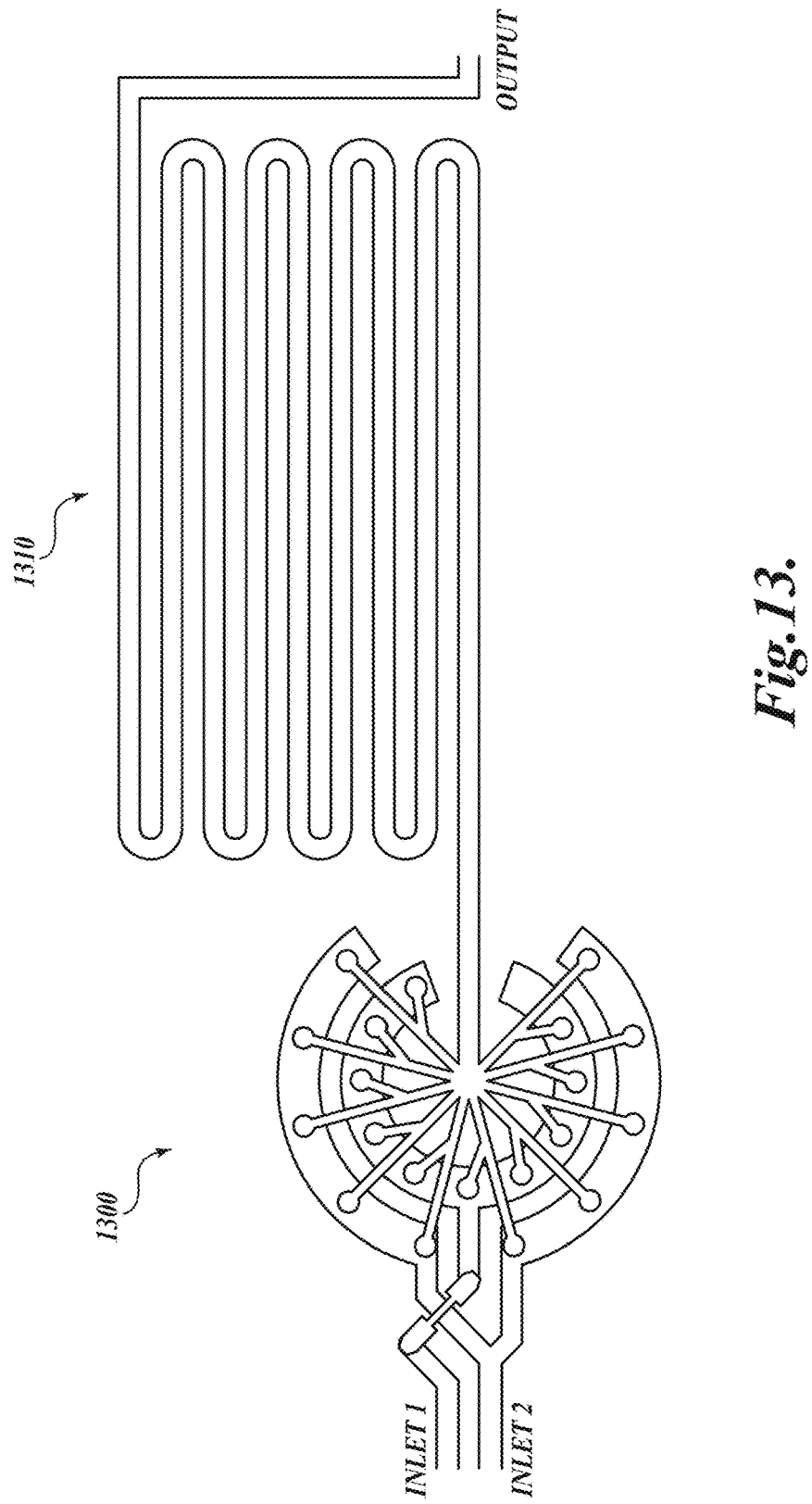
FIG. 13 is a schematic illustration of a representative fluidic device of the invention having a multilaminate mixer (device 1300 includes mixing channel 1310).
Figure 14:
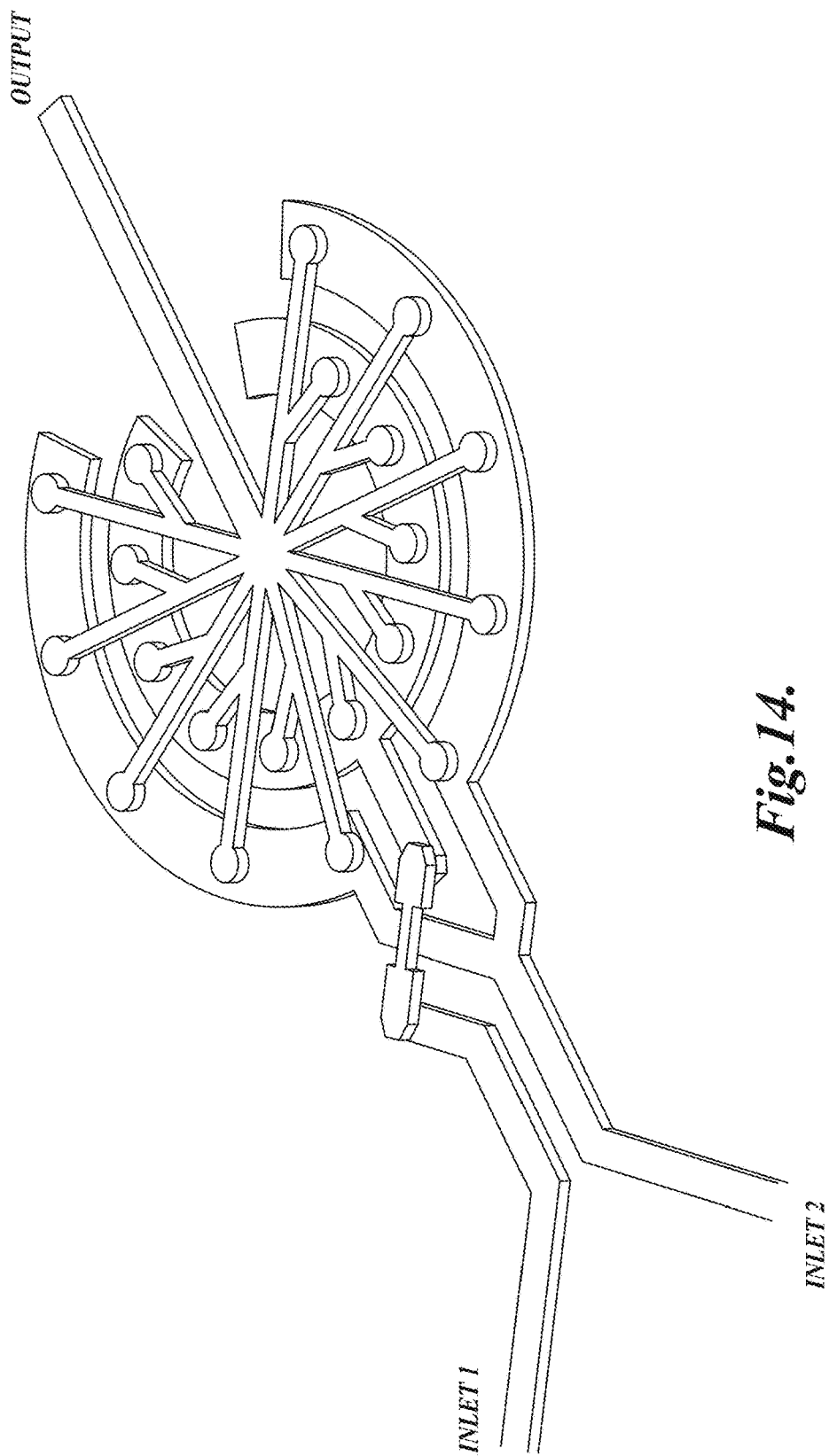
FIG. 14 is a close-up view of the multilaminate mixer illustrated in FIG. 14.

FIG. 13 is a schematic illustration of a representative fluidic device of the invention having a multilaminate mixer. Referring to FIG. 13, device 1300 includes mixing channels 1310. FIG. 14 is a close-up view of the multilaminate mixer illustrated in FIG. 14.

As described above, methods of making lipid micro/nanoparticles have been conventionally "top down" approaches where larger structures are formed by dispersion of lipids in water, followed by disruption of the multilamellar vesicles (micron size range) through polycarbonate filters with a pore size such as 100 nm or alternatively, using tip sonication.

One aspect lacking in such batch processes is the ability to precisely control the structure and assembly of each lipid mixture constituent. This is especially important if certain constituents are easily degraded if exposed to their external environment, or if certain ligands must reside on the exterior of the particle for targeting purposes. For example, with therapeutics it may be important to first produce a particle that has a net positive or negative surface charge to associate a certain therapeutic drug. Further processing may then be needed to complete the assembly, by encapsulating such a particle with other lipid material or to modify its surface characteristics. This may for example include addition of lipids to produce a net neutral particle, or addition of targeting molecules that must reside on the exterior of the particle for functional purposes.

In one embodiment, the method for making lipid nanoparticles includes sequential assembly and growth of lipid nanoparticles through charge association, and further, can provide encapsulation of therapeutic small interfering RNA (siRNA). This method can be used to completely alter the surface charge characteristics from net positive to net negative and vice versa.

Figure 28A:
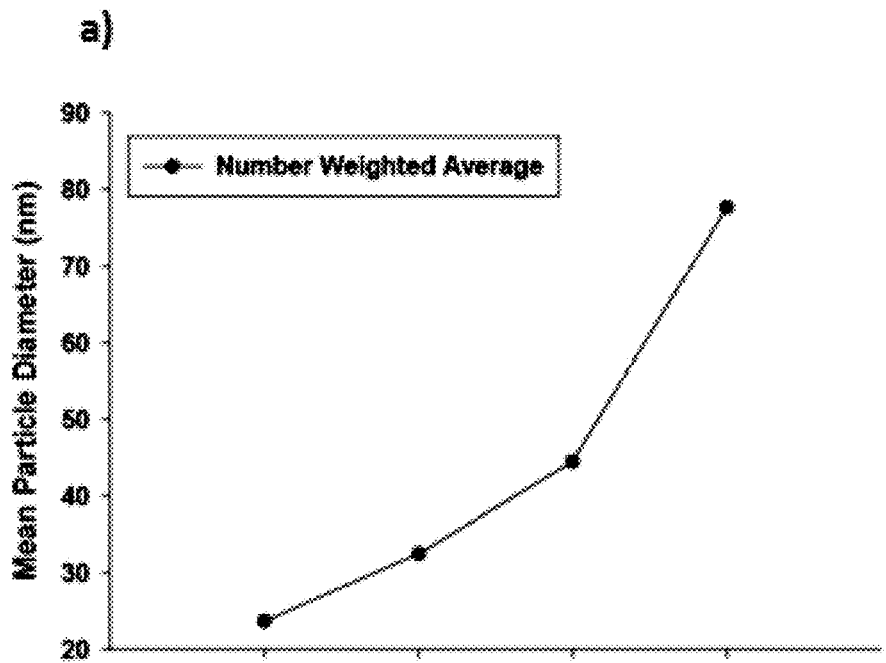
FIGS. 28A and 28B illustrate mean particle diameter (nm) and zeta potential (mV), respectively, as a function of sequential lipid nanoparticle composition prepared using the microfluidic mixer.
Figure 28B:
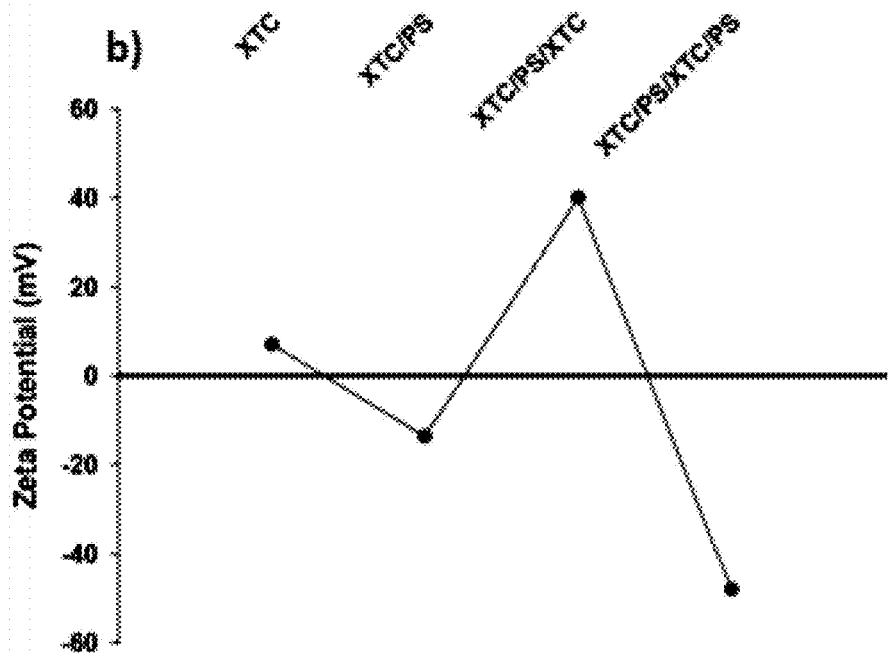

A lipid nanoparticle encapsulating siRNA (−ive) was prepared with a charge ratio of about 2 (+ive/−ive). The lipids included 90 mol % DLin-KC2-DMA (+ive) and 10 mol % PEG-c-DMA. The resulting particle was 23 nm in diameter (FIG. 28A) and had a positive zeta potential of about 7 mV (FIG. 28B). The anionic lipid was then incorporation in 4-fold excess to the cationic lipid via microfluidic mixing. This led to an increase in particle size to 33 nm and a shift to a negative zeta potential of −14 mV. Further incorporation of additional cationic lipid (in 4-fold excess to the previous DOPS) and then incorporation of DOPS led to a continued increase in particle size and alteration between net positive and net negative zeta potentials.

Figure 29:
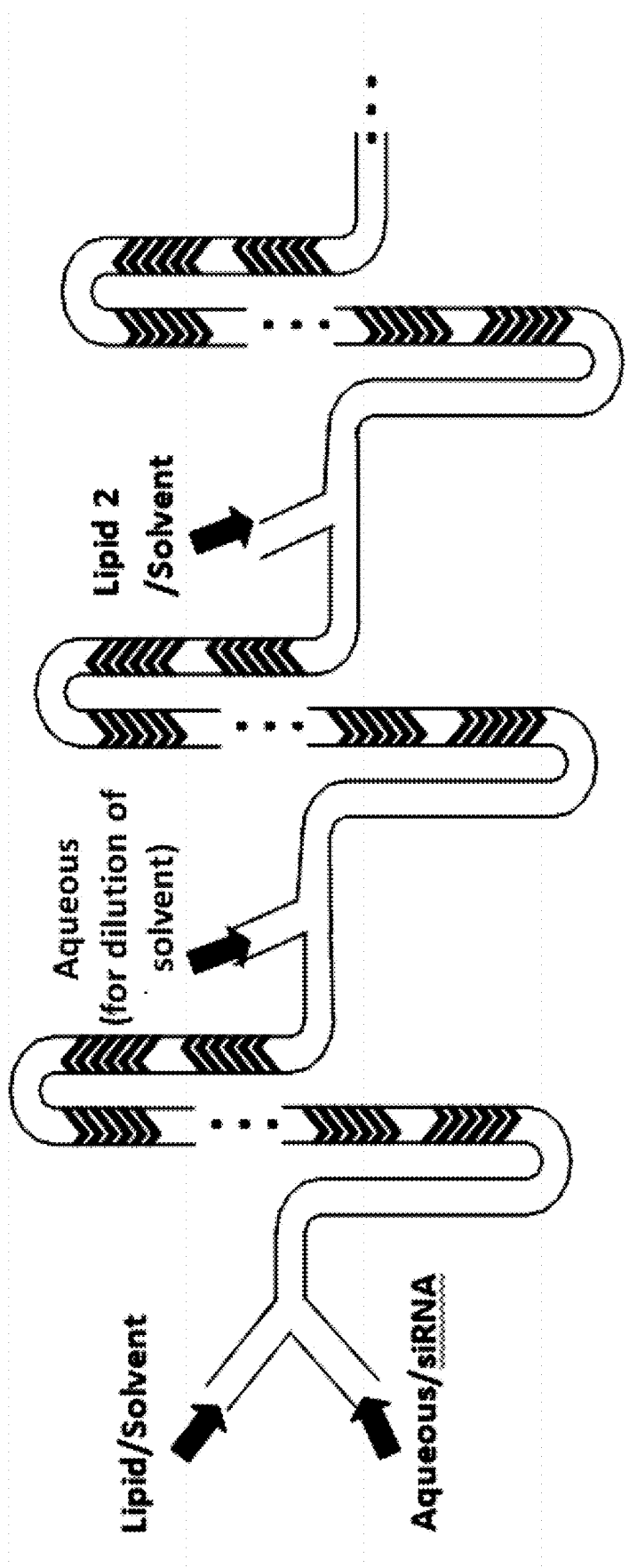
FIG. 29 is a schematic representation of a representative device and method of the invention for the sequential assembly of lipid nanoparticles.

The results were obtained by mixing in a single microfluidic mixer, recovered, and then re-injected into the micromixer to add the next lipid component. However, a single microfluidic device could be designed to produce such particles in a continuous manner (FIG. 29).

The following devices minimize the fluidic impedances and the interaction between the lipid and aqueous fluids prior to entering the micromixer.

Figure 30:
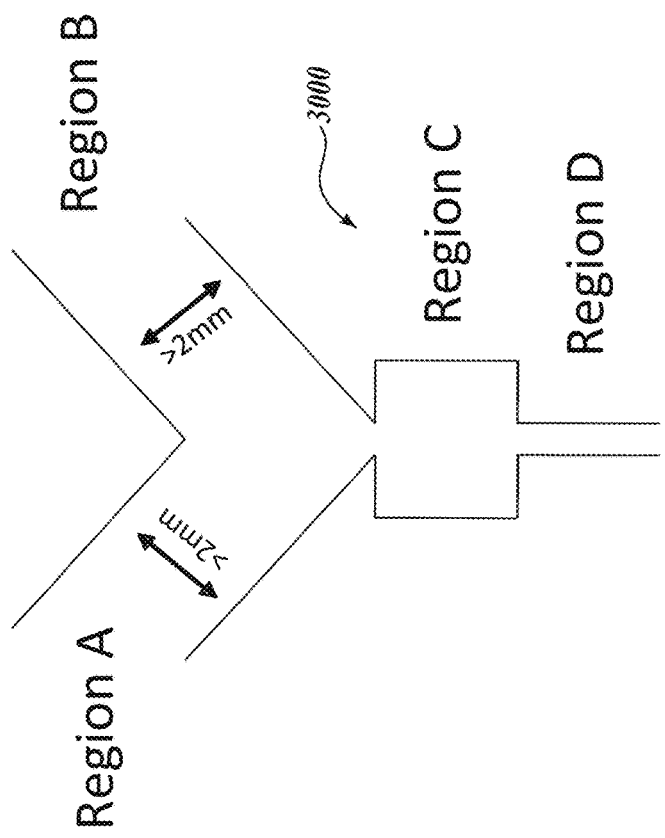
FIG. 30 is a schematic representation of a representative device and method of the invention.

FIG. 30 is a schematic representation of a representative device 3000 and method of the invention. Referring to FIG. 30, device 3000 includes Region A, where a first stream comprising a polynucleic acid in a first solvent into a channel of large width (>2 mm) and Region B, where a stream comprising lipid particle-forming materials in a second solvent into a channel of large width (>2 mm). The streams are introduced into Region C where rapid mixing occurs in a micromixer and then ultimately to Region D, the final product.

Figure 31:
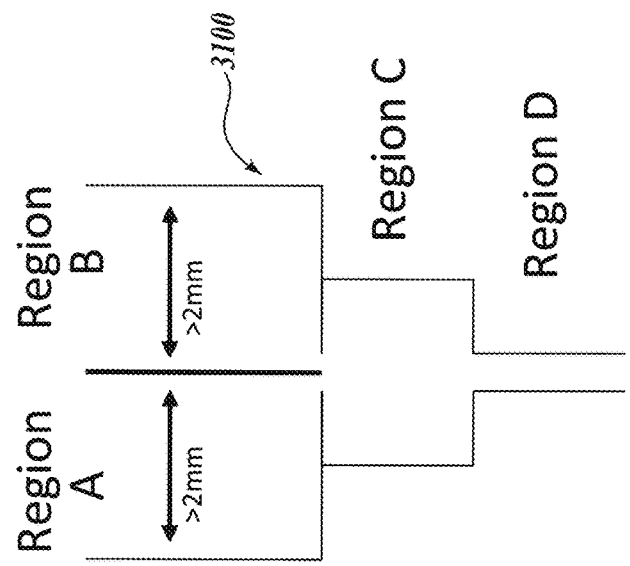
FIG. 31 is a schematic representation of a representative device and method of the invention.

FIG. 31 is a schematic representation of a representative device and method of the invention. Referring to FIG. 31, device 3100 includes Region A, where a first stream comprising a polynucleic acid in a first solvent into a channel of large width (>2 mm) and Region B, where a stream comprising lipid particle-forming materials in a second solvent into a channel of large width (>2 mm). The streams are introduced into Region C where rapid mixing occurs in a micromixer and then ultimately to Region D, the final product.

Figure 32:
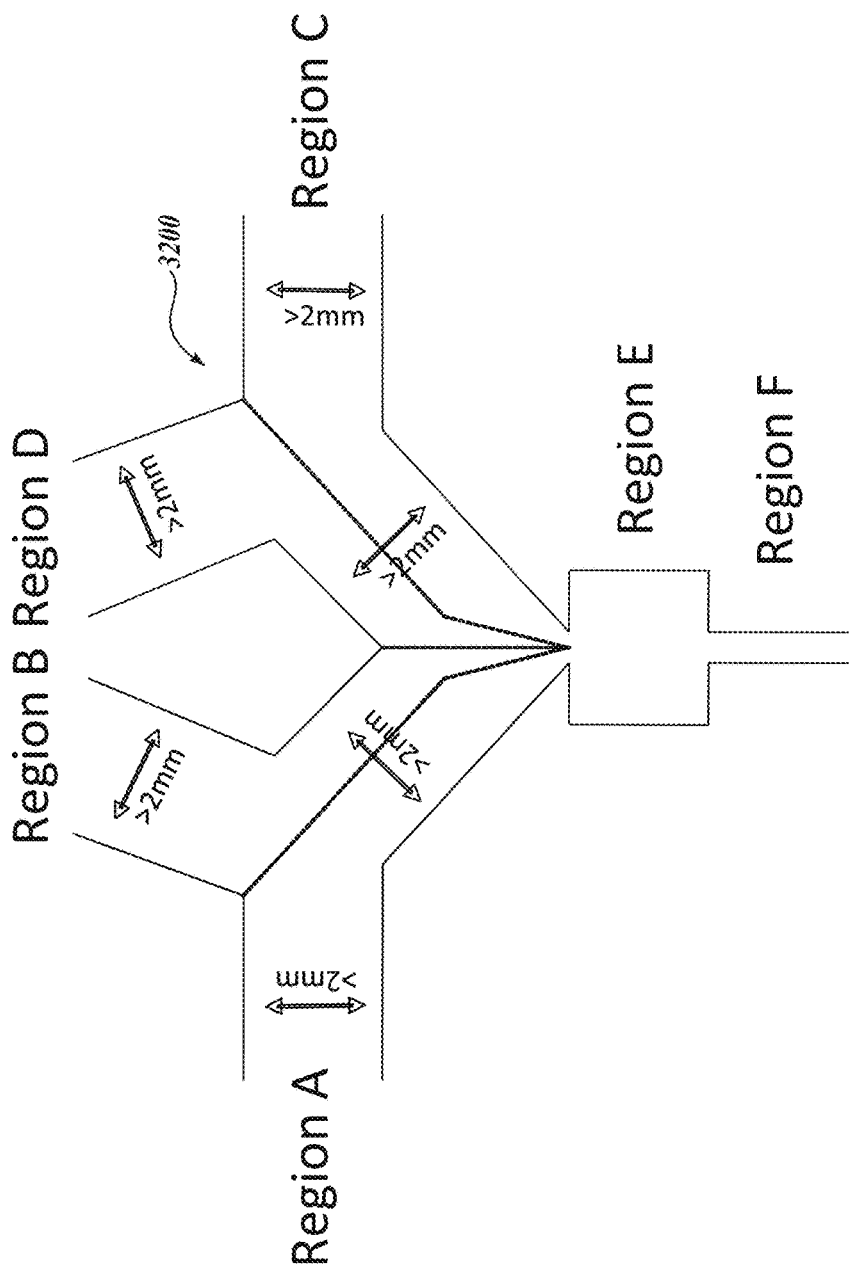
FIG. 32 is a schematic representation of a representative device and method of the invention.

FIG. 32 is a schematic representation of a representative device and method of the invention. Referring to FIG. 32, device 3200 includes Region A, where a first stream comprising a polynucleic acid in a first solvent into a channel of large width (>2 mm); Region B, where a second stream comprising the first solvent to act as sheath fluid for the flow of Region A; Region C, where a stream comprising lipid particle-forming materials in a second solvent into a channel of large width (>2 mm); and Region D, where a second stream comprising the second solvent to act as sheath fluid for the flow of Region C. The streams are introduced into Region E where rapid mixing occurs in a micromixer and then ultimately to Region F, the final product. The dotted lines represent fluidic interfaces.

Figure 33:
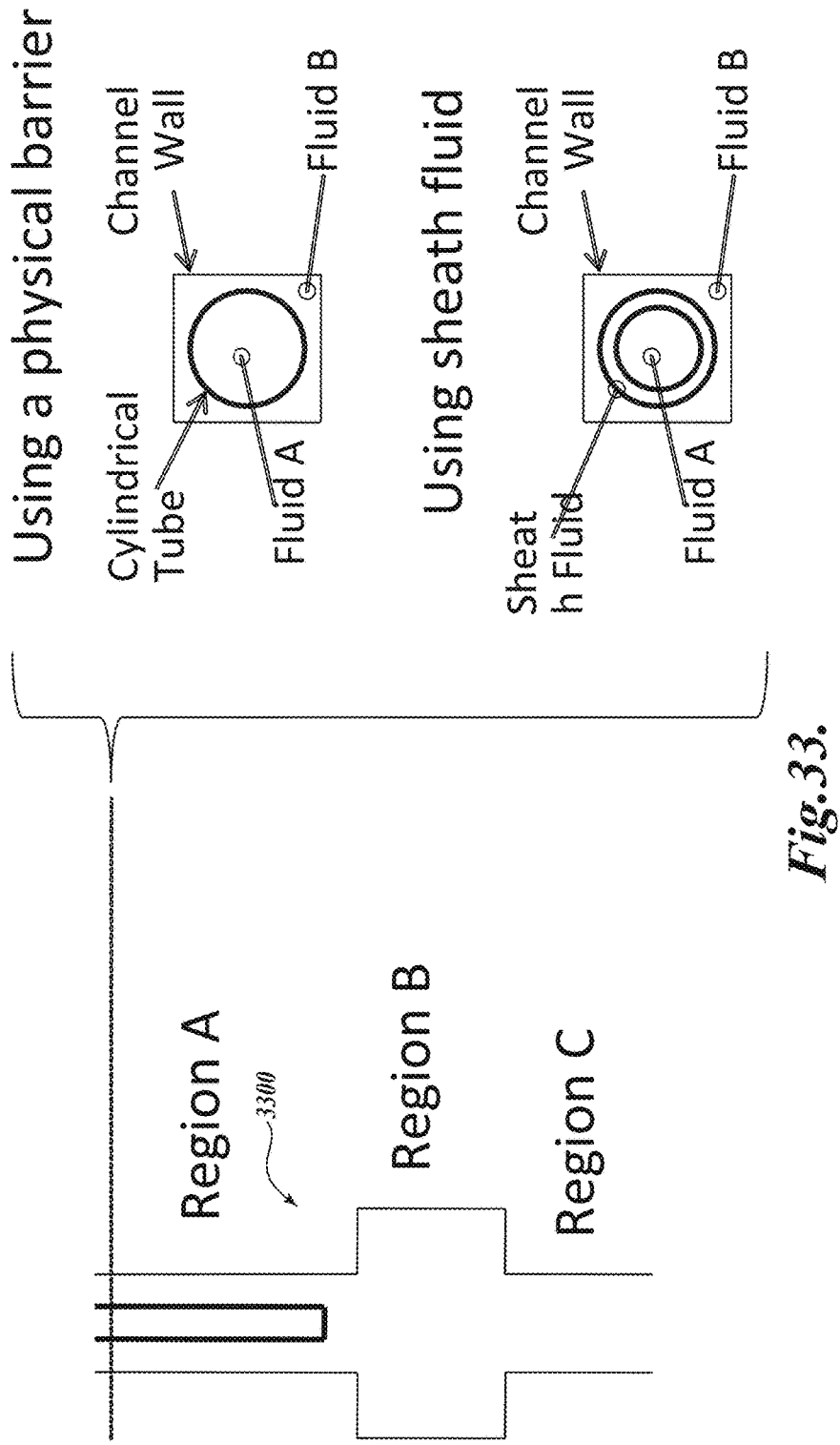
FIG. 33 is a schematic representation of a representative device and method of the invention.

FIG. 33 is a schematic representation of a representative device and method of the invention. Referring to FIG. 33, device 3300 includes Region A, where a first stream comprising an polynucleic acid in a first solvent and a second stream comprising lipid particle-forming materials in a second solvent are flown concentrically into a channel, are introduced into Region B where rapid mixing occurs in a micromixer and then ultimately to Region C where we have the final product. The two fluids in Region A may be separated by a physical barrier or by sheath fluid as demonstrated in the cross sectional view.

Method for Delivering Therapeutic Agents Using Lipid Particles

The lipid particles of the present invention may be used to deliver a therapeutic agent to a cell, in vitro or in vivo. In particular embodiments, the therapeutic agent is a nucleic acid, which is delivered to a cell using nucleic acid-lipid particles of the present invention. The methods and compositions may be readily adapted for the delivery of any suitable therapeutic agent for the treatment of any disease or disorder that would benefit from such treatment.

In certain embodiments, the present invention provides methods for introducing a nucleic acid into a cell. Preferred nucleic acids for introduction into cells are siRNA, miRNA, immune-stimulating oligonucleotides, plasmids, antisense and ribozymes. These methods may be carried out by contacting the particles or compositions of the present invention with the cells for a period of time sufficient for intracellular delivery to occur.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the compositions of the present invention can also be used for deliver of nucleic acids to cells in vivo, using methods which are known to those of skill in the art.

The delivery of siRNA by a lipid particle of the invention and its effectiveness in silencing gene expression is described below.

For in vivo administration, the pharmaceutical compositions are preferably administered parenterally (e.g., intraarticularly, intravenously, intraperitoneally, subcutaneously, or intramuscularly). In particular embodiments, the pharmaceutical compositions are administered intravenously or intraperitoneally by a bolus injection. Other routes of administration include topical (skin, eyes, mucus membranes), oral, pulmonary, intranasal, sublingual, rectal, and vaginal.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In a further aspect, the invention provides a pharmaceutical composition comprising a lipid particle of the invention and a pharmaceutically acceptable carrier or diluent. Representative pharmaceutically acceptable carriers or diluents include solutions for intravenous injection (e.g., saline or dextrose). The composition can take the form of a cream, ointment, gel, suspension, or emulsion.

The following is a description of a representative LNP system, device and method for making the LNP system, and method for using a LNP for delivering therapeutic agents.

Rapid Microfluidic Mixing Allows Production of Monodisperse Lipid Nanoparticles.

Formulation of lipid nanoparticles was performed by rapidly mixing a lipid-ethanol solution with an aqueous buffer inside a microfluidic mixer (FIG. 15B) designed to induce chaotic advection and provide a controlled mixing environment at intermediate Reynolds number (24<Re<240). The microfluidic channel contains herringbones that generate a chaotic flow by changing the orientation of herringbone structures between half cycles, causing a periodic change in the centers of local rotational and extensional flow.

To determine mixing performance inside the device, the pH sensitivity of fluorescein was used where two 10 μM fluorescein streams were mixed, one fluorescent at pH 8.88 and the other non-fluorescent at pH 5.15. The channel length required for mixing to occur (extent of mixing >95%) was found to be between 0.8 cm and 1.0 cm. This resulted in mixing times of approximately 45 ms, 10 ms, and 5 ms and 3 ms for flow rates of 0.1 ml/min, 0.4 ml/min, 0.7 ml/min and 1.0 ml/min, respectively. The small difference in mixing length is expected in a chaotic flow, which grows only logarithmically with Péclet number ($Pe=Ul/D$ where U is the fluid velocity, l is the cross sectional channel length, and D is the diffusivity of the molecule).

Figure 16A:
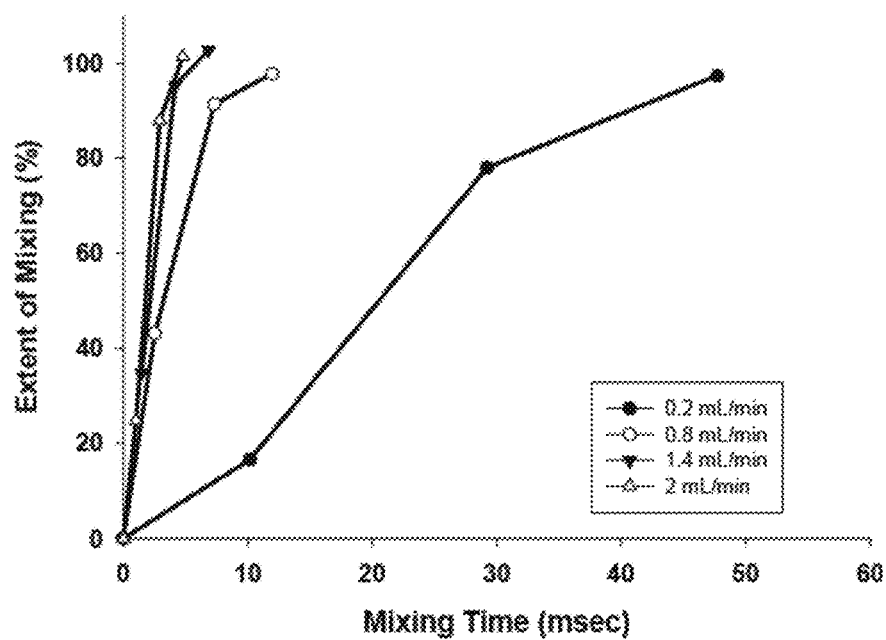
FIGS. 16A-16C illustrate the influence of flow rate in microfluidic device on mixing and LNP particle size. Two 10 μM fluorescein (fluorescent at pH 8.8, non-fluorescent at pH 5.15) solutions mix to produce completely fluorescent solution.
Figure 16B:
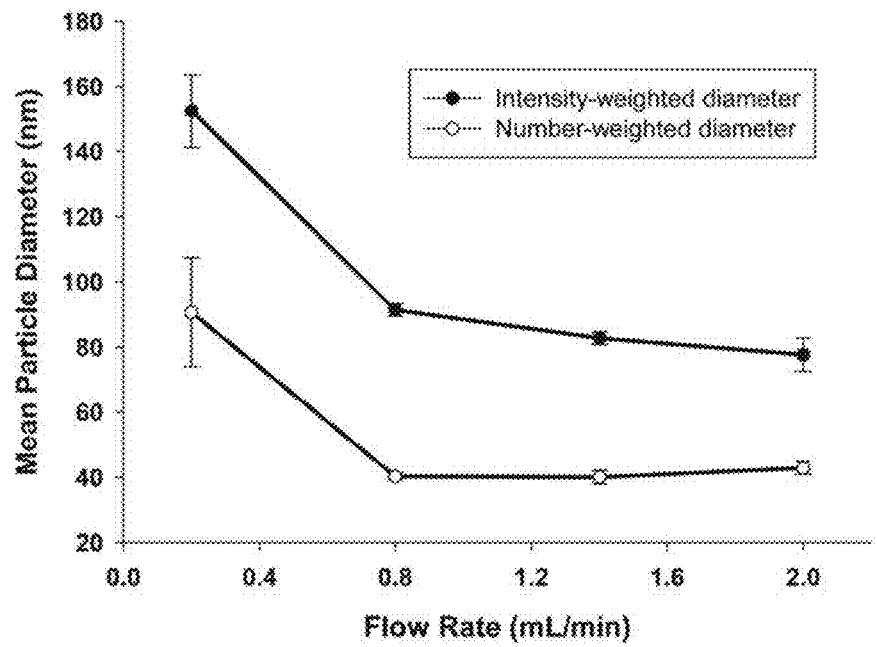
Figure 16C:
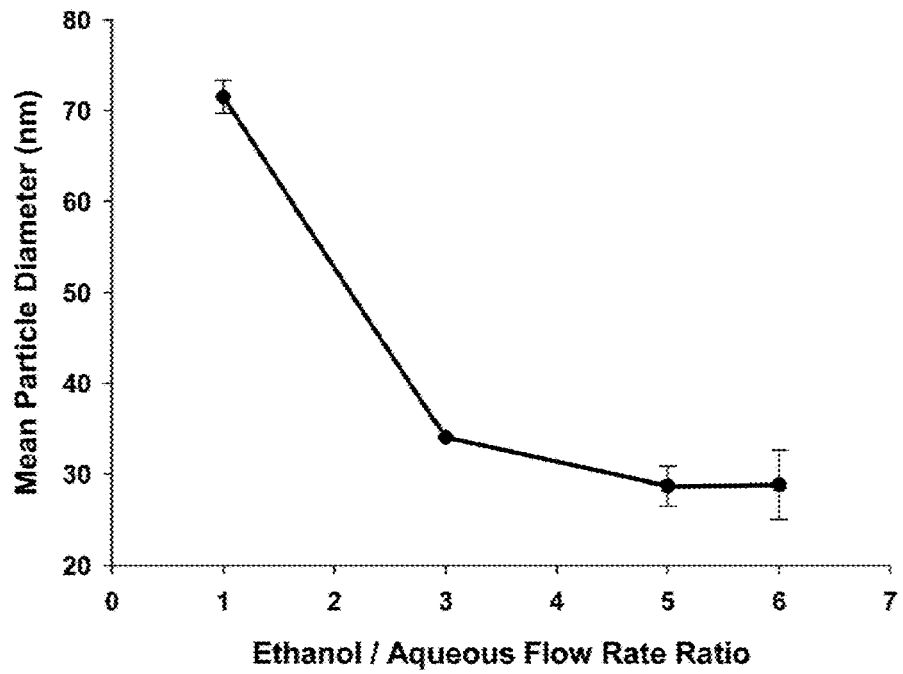

The following representative formulations include an ionizable cationic lipid, DLin-KC2-DMA, having an apparent pKa of 6.7 rendering the lipid suitable for encapsulation of siRNA at low pH and providing a near neutral cationic surface charge density at physiological pH. Using this LNP-siRNA scheme as a model system, the effect of flow rate on LNP formation was determined. As the mixing time dramatically decreases with increased flow rate, the speed at which lipids are introduced into the aqueous phase was expected to influence their final size and dispersity. Using identical flow rates, from 0.1 ml/min to 1 ml/min per channel, FIG. 16B shows the mean particle diameter of LNP-siRNA systems produced by the microfluidic mixer. The buffer contained siRNA to yield a siRNA/total lipid ratio of 0.06 (wt/wt) and the LNP mixture was diluted directly into buffer to reduce ethanol content to approximately 22 vol %. Particle size decreased significantly when increasing total flow rate from 0.2 ml/min to 2 ml/min. Particle size was largest under a flow rate of 0.2 ml/min and the LNP reached a limit size of approximately 40 nm as determined from the number-weighted particle diameter. Alternatively, the mixing time was also adjusted by changing the ratio of the ethanol and aqueous streams. Increasing the flow rate of the aqueous stream in effect provides a quicker dilution of the lipids with the aqueous stream. With the lipid-ethanol stream kept constant at 0.5 ml/min, an increase in the aqueous flow rate resulted in a decrease in particle size (FIG. 16C). The substantial drop in particle size, from about 70 nm to 35 nm, with a three-fold increase in the aqueous flow rate highlights the importance in rapidly reducing the ethanol content.

Figure 17:
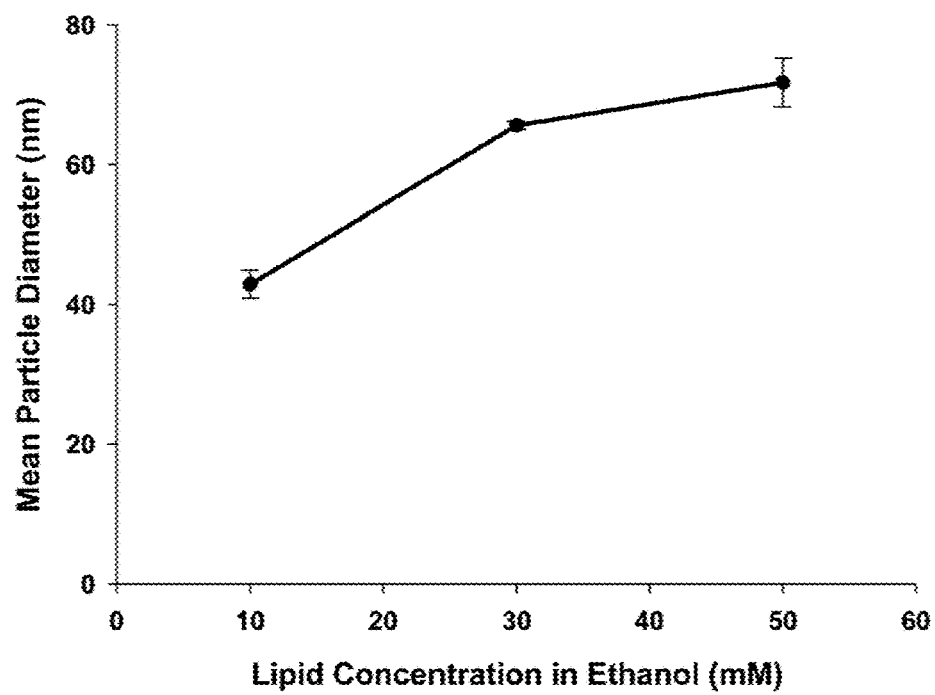
FIG. 17 illustrates the influence of lipid concentration on LNP particle size by comparing mean particle diameter (nm) as a function of lipid concentration in ethanol (mM). Increasing the lipid concentration results in an increase in mean particle diameter. The total lipid content in the ethanol phase being mixing in the microfluidic chip was varied from 10 mM to 50 mM. LNP composed of Dlin-KC2-DMA/DSPC/Cholesterol/PEG-c-DMA at mole ratios of 40:11.5:47.5:1, siRNA-total lipid ratio 0.06 wt/wt. Total flow rate inside microfluidic mixer was maintained at 2 ml/min. Error bars represent standard deviation of the mean particle diameter as measured by dynamic light scattering.

Because these LNP are expected to form spontaneously as the lipids encounter a more aqueous environment, it was also important to explore the effect of lipid concentration. As lipid concentration is increased, the amount of lipids available to incorporate into a LNP would be expected to increase or otherwise form additional particles. This was monitored as the lipid concentration was increased from 10 mM to 50 mM in the ethanol stream. An increase in mean particle diameter from about 40 nm to 70 nm was observed following this increase in lipid concentration (FIG. 17).

Rapid Microfluidic Mixing Provides a Broad Formulation Range of LNP-siRNA Systems.

While recent improvements of the cationic lipid have advanced LNP potency several fold, it has also become apparent that further improvements can be provided via optimization of the LNP composition. In particular, it can influence their bilayer-destabilizing capacity and endosomolytic potential or may influence their circulation behavior at physiological pH. For example, formulations with less PEG-lipid and increased cationic lipid have shown dramatic improvements in in vivo efficacy of LNP systems targeting liver hepatocytes. This was observed in a recent report for a mouse Factor VII model, which provided a further five-fold reduction in ED50 in the optimized LNP. Although the PEG-lipid is necessary for particulate stability, it can also diminish the membrane-destabilizing property of these LNP systems. With the preformed vesicle (PFV) method, difficulties have been encountered when attempting to produce LNP systems with less than 5 mol % PEG-lipid; this is presumably due to less PEG content on the exterior of the vesicles which increases fusion between LNPs. Further, the incubation step necessary for reorganization of preformed lipid particles and encapsulation of siRNA requires ethanol solutions in the range of 30% (v/v). This increased lipid fluidity can promote instability and lead to additional aggregation and fusion of the preformed lipid particles.

Figure 18A:
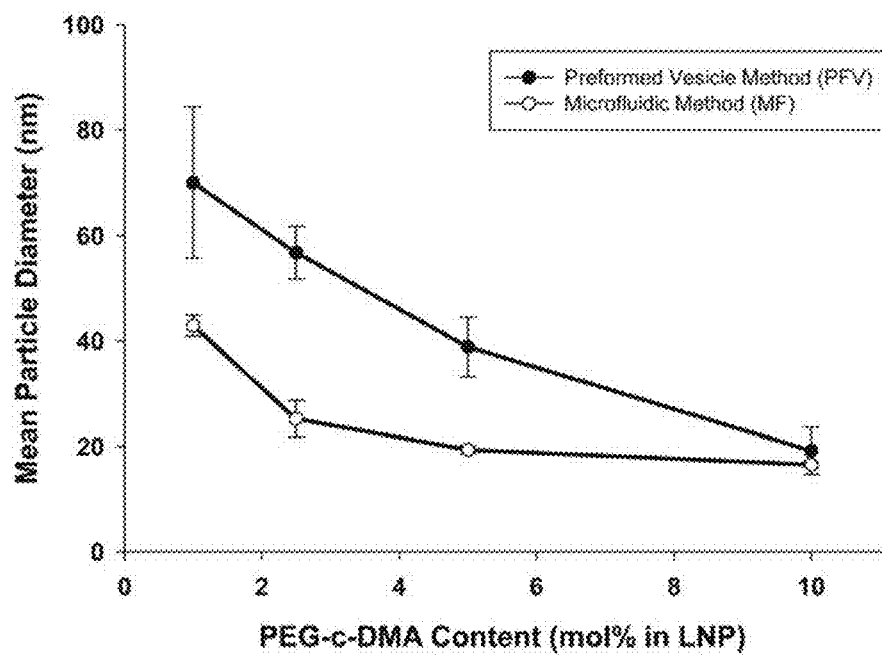
FIGS. 18A and 18B illustrate the influence of PEG-lipid and cationic lipid on LNP systems.
Figure 18B:
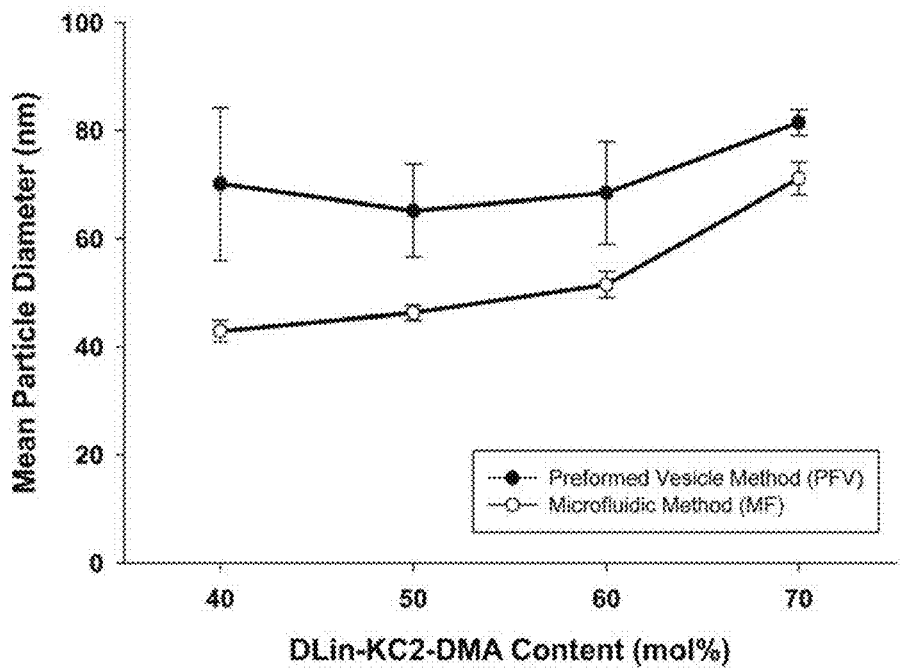

Using PEG-c-DMA, the ability of the microfluidic (MF) method (fast mixing times and short residence prior to dilution of the LNP below 25% ethanol (v/v)) to produce LNP-siRNA systems with varying PEG-lipid content was explored. An initial composition of DLin-KC2-DMA, DSPC, cholesterol, and PEG-c-DMA (40:11.5:38.5:10 mol/mol) was used with a siRNA/total lipid ratio of 0.06 (wt/wt). Additional cholesterol was used to compensate for the decreased amount of PEG-c-DMA. Titration of PEG-c-DMA to 2 mol % led to only a minor increase in particle size using the microfluidic approach. Further decrease to 1 mol % PEG led to an increase in diameter from about 20 nm to about 40 nm (FIG. 18A). In contrast, the mean particle diameter using the PFV method showed a constant increase in particle diameter, from 20 nm to 70 nm, as PEG-lipid content was decreased to 1 mol %. In addition to producing LNP with low amounts of PEG-lipid, it is of interest to be able to vary the amount of cationic lipid. As DLin-KC2-DMA was increased from 40 mol % to 70 mol %, a general increase in particle size was observed, from about 40 nm to 70 nm, for those produced by the microfluidic approach (FIG. 18B).

Self Assembly in a Microfluidic Device can Produce LNP with Near Complete Encapsulation.

Figure 19:
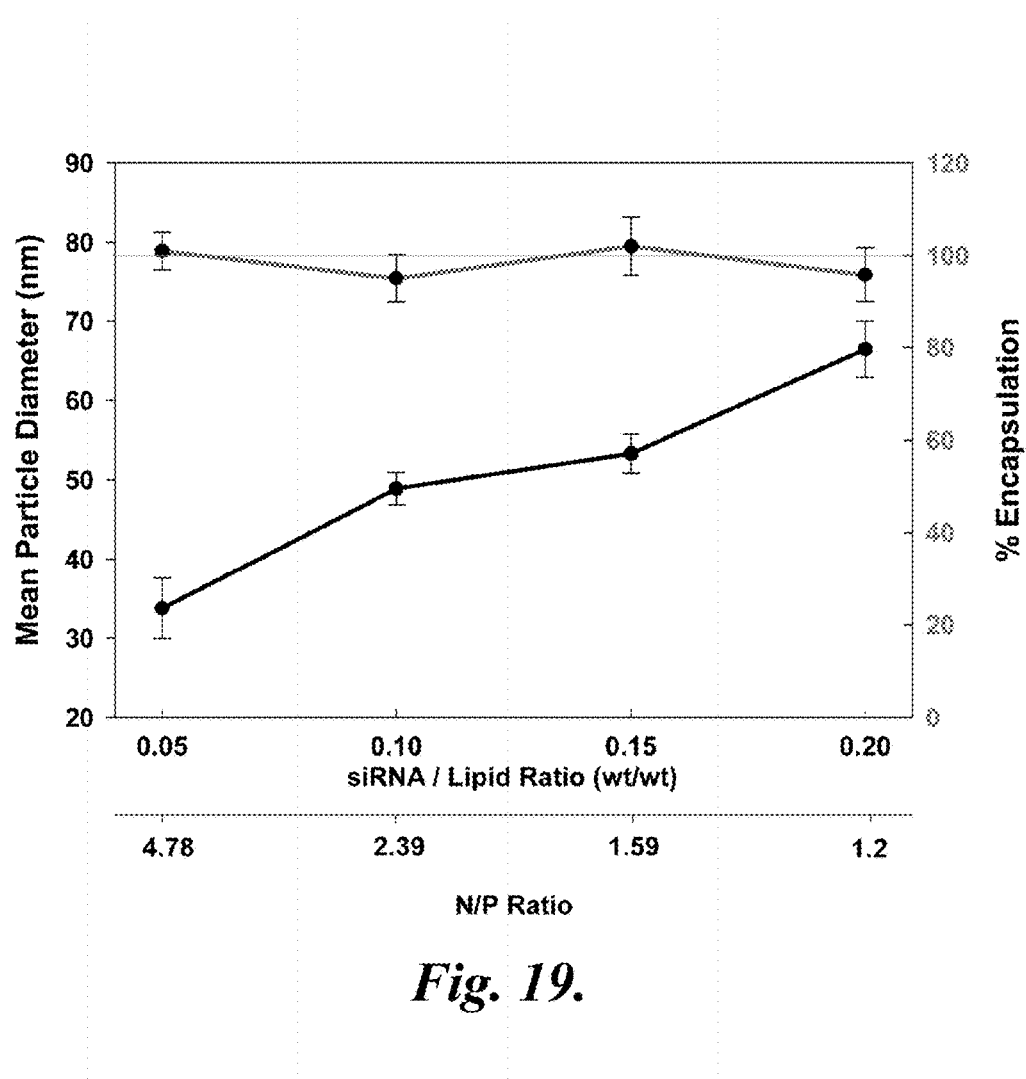
FIG. 19 illustrates the influence of siRNA/Lipid ratio on particle size and encapsulation by comparing mean particle diameter (nm) and encapsulation (%) as a function of siRNA/lipid ratio (wt/wt) (also expressed as nucleotide/phosphate (N/P). Encapsulation determined by separation of LNP suspension from free siRNA using an anionic exchange spin column. LNP were composed of Dlin-KC2-DMA/DSPC/Cholesterol/PEG-c-DMA at mole ratios of 40:11.5:47.5:1, siRNA-total lipid ratio 0.06 wt/wt. Total flow rate inside microfluidic mixer was maintained at 2 ml/min. 10 mM lipid-ethanol phase mixed with 25 mM acetate buffer, pH 4, containing siRNA. Error bars represent standard deviation of the mean particle diameter as measured by dynamic light scattering.

In producing LNP-siRNA systems, a robust process necessarily will provide high percent encapsulation of the OGN product. siRNA encapsulation was evaluated by varying the siRNA/total lipid ratio from 0.01 to 0.2 (wt/wt) using the LNP-siRNA formulation with 1 mol % PEG. LNP formulations achieved percent encapsulation approaching 100 percent over this range (FIG. 19). Upon reaching a siRNA/total lipid ratio of 0.21 (wt/wt), corresponding to a charge balance between the cationic lipid and anionic siRNA (N/P=1), encapsulation was observed to diminish (data not shown). This later trend was expected due to insufficient cationic charge required to complex the siRNA and encapsulate in the LNP.

Morphology.

Figure 20A:
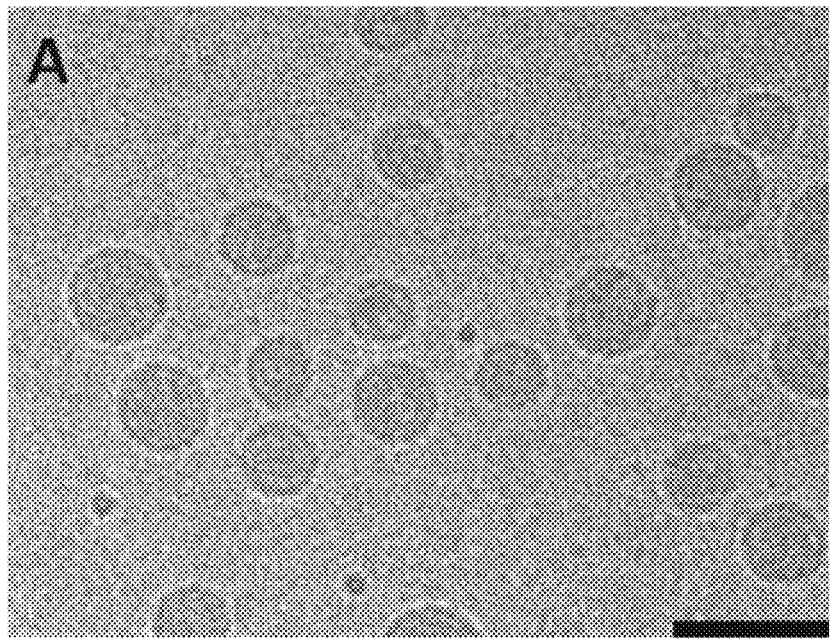
FIGS. 20A and 20B illustrate the morphology of PEG-lipid and cationic lipid LNP systems prepared by the microfluidic mixer using Cryo-Transmission Electron Microscopy (TEM). LNP were imaged at 29K magnification by Cryo-TEM.
Figure 20B:
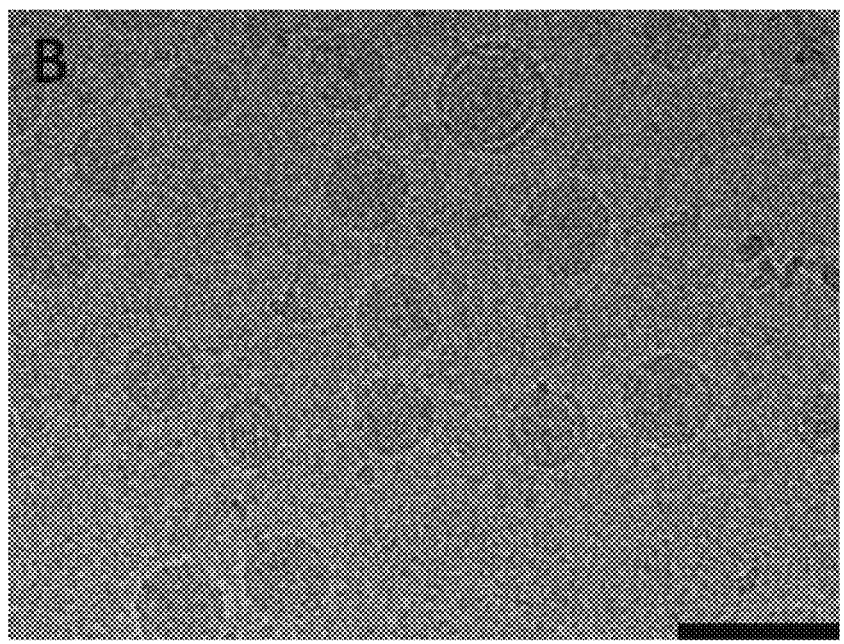

LNP produced by the microfluidic and preformed vesicle methods were visualized with cryo-TEM. Particle sizes of the LNP were similar to that measured by dynamic light scattering. LNP-siRNA systems containing DLin-KC2-DMA/DSPC/Cholesterol/PEG-c-DOMG at 40/11.5/47.5/1 mol % with siRNA-to-lipid ratio of 0.06 wt/wt are shown in FIG. 20A. In addition, empty LNP samples of the same composition are shown in FIG. 20B. The particles produced are predominately spherical and homogeneous in size. LNP formulated with the preformed approach and of identical composition was also imaged. These shared similar features with the microfluidic LNP, though other features such as coffee-bean structures were also observed. These LNP were also larger in size, as expected from the dynamic light scattering results.

LNP siRNA Systems Produced by Microfluidics can be Highly Potent Gene Silencing Agents In Vivo.

The ability of LNP siRNA systems to induce gene silencing in vivo following i.v. injection was investigated using the mouse Factor VII model.

Figure 21:
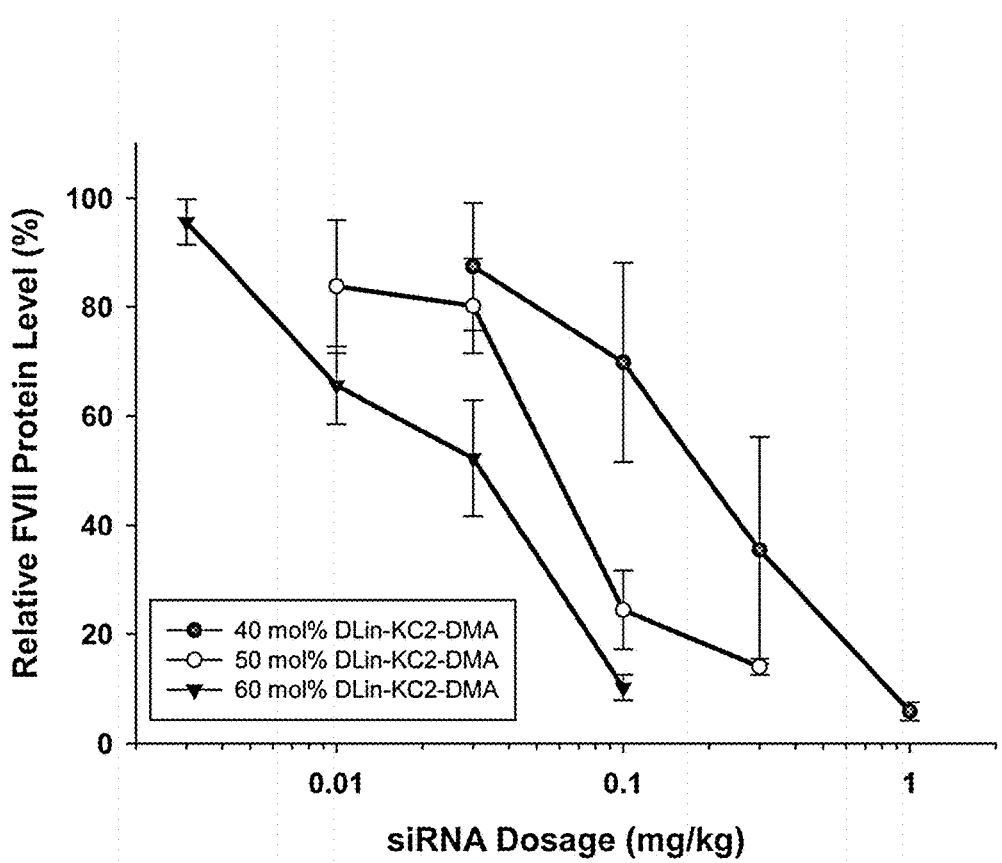
FIG. 21 illustrates in vivo silencing activity of microfluidic produced LNP in Factor VII Mouse Model by comparing relative FVII Protein Level (%) as a function of siRNA dosage (mg/kg) varying DLin-KC2-DMA content in the LNP from 40 mol % to 60 mol %. Formulation of LNP containing 1 mol % PEG-c-DOMG and 60 mol % DLin-KC2-DMA provide FVII silencing similar to that previously reported using alternative approaches. Gene silencing progressively improves for LNP containing DLin-KC2-DMA over the range from 40 mol % to 60 mol %. Systemic injection of LNP-siRNA to mice was performed by tail vein injection (n=3 per dose level). Blood collection was performed after 24 hrs post-injection and factor VII levels were determined by colorimetric assay. LNP DSPC-to-Cholesterol ratio was kept at 0.2 wt/wt and contained 1 mol % PEG-c-DOMG. LNP siRNA-to-lipid ratio was 0.06 wt/wt.

Formulations containing DLin-KC2-DMA/DSPC/Cholesterol/PEG-c-DOMG with a siRNA-to-lipid ratio of 0.06 (w/w) were created using the microfluidic approach. Administration of the LNP-siRNA was by tail vein injection. The cationic lipid, DLin-KC2-DMA, was varied from 30 mol % to 60 mol % while keeping the DSPC-to-Cholesterol ratio at 0.2 wt/wt. Increasing the cationic lipid content in the LNP resulted in a progressive improvement in FVII silencing. The best performing LNP contained 60 mol % DLin-KC2-DMA, resulting in an effective dose for 50% FVII silencing at about 0.03 mg/kg (FIG. 21). It is interesting to note that further increase to 70 mol % led to no observable improvement in efficacy over the 60 mol % Dlin-KC2-DMA LNP.

The results demonstrate that a microfluidic device containing a staggered herringbone mixer can be used to generate LNP with a variety of lipid compositions, can be used to efficiently encapsulate OGN such as siRNA and that the LNP siRNA systems produced exhibit excellent gene silencing capabilities both in vitro and in vivo.

The microfluidics device and system of the invention allow for the formation of LNP and LNP containing OGN of 100 nm size or smaller and provide OGN encapsulation 100%. With regard to formation of LNP, the rate and ratio of mixing are clearly the important parameters. Rapid mixing of the ethanol-lipid solution with aqueous buffer results in an increased polarity of the medium that reduces the solubility of dissolved lipids, causing them to precipitate out of solution and form nanoparticles. Rapid mixing causes the solution to quickly achieve a state of high supersaturation of lipid unimers throughout the entire mixing volume, resulting in the rapid and homogeneous nucleation of nanoparticles. Increased nucleation and growth of nanoparticles depletes the surrounding liquid of free lipid, thereby limiting subsequent growth by the aggregation of free lipid. This proposed mechanism is consistent with the observation that lower concentrations of the lipid in ethanol (reduced free lipid) result in smaller LNP (see FIG. 17), that higher flow rates, causing a faster and more homogeneous approach to supersaturation, lead to formation of smaller LNP, and that increasing the relative ratio of the aqueous to organic solvent components also results in smaller particles (FIG. 17).

LNP OGN systems of the invention formulated by the microfluidics method exhibit OGN encapsulation efficiencies approaching 100%. Previous cryo-TEM studies using the PFV technique for antisense OGN have revealed the presence of small multilamellar vesicles leading to the possibility that encapsulation involves OGN adsorption to a preformed vesicle which serves as a nucleation point for association with additional preformed vesicles that wrap around the original vesicle. In contrast, cryo-TEM studies of the LNP OGN produced by the microfluidics method show that the majority of the LNP systems are "solid core" structures and suggest that a different mechanism of OGN encapsulation is operative. In particular, these structures are consistent with the association of siRNA with cationic lipid monomers prior to or simultaneously with nanoparticle assembly. The ability of the microfluidics method to facilitate encapsulation efficiencies for antisense and siRNA OGN approaching 100% independent of nucleic acid composition is a major advantage over previously reported methods.

The microfluidics method provides advantages over three alternative LNP synthesis techniques including the classical extrusion procedure for producing LNP, the preformed vesicle method, and the spontaneous vesicle formation methods for OGN encapsulation. The microfluidics method provides LNP in the 100 nm size range or smaller and, when cationic lipid is present, allows LNP to be formed with low levels of stabilizing PEG-lipid. Disadvantages of the microfluidics method relate to the need to remove ethanol after preparation, the fact that certain lipids are relatively insoluble in ethanol, and potential scalability issues. The microfluidics method offers advantages in encapsulation efficiencies, the use of high cationic lipid contents and low PEG-lipid levels that are difficult to employ using the PFV process, removal of the need to generate preformed vesicles, and the ability to produce small scale batches using as little as 150 µg of oligonucleotide with little loss due to the small dead volume (1 µl) of the apparatus.

Advantages of the microfluidics method as compared to the SVF "T tube" procedure for generating LNP systems loaded with OGN are similar to those indicated for the PFV process, with the exception that preformed vesicles are not required. The aperture of the T tube is approximately 1.5 mm in diameter, requiring high flow rates (>1 ml/s) to achieve the velocities required for rapid mixing to occur. The micromixer allows LNP OGN formulation to occur under well defined, reproducible conditions at much lower flow rates and reduced losses due to dead volumes, allowing more straightforward preparation of small scale batches for LNP optimization and in vitro testing.

LNP OGN systems can be scaled up. Although a device that has a maximum flow rate of 1 ml/min may be insufficient, a single microfluidics chip may contain 10 or more micromixers in to achieve total flow rates of about 10 mL/min. Given the relatively inexpensive nature of this technology it is practical that a number of such chips to be used in parallel, potentially allowing flow rates of 100 ml/min or higher from a single bench-top instrument. Furthermore, upstream fluid handling could easily be incorporated into such a device to allow for precise programmable formulations from multiple components, a feature that would be highly advantageous in the screening and optimization of synthesis formulations and parameters.

Solid Core LNP

Certain models of LNP siRNA formulations suggest a bilayer vesicle structure of the LNP with siRNA on the inside in an aqueous interior. However a number of observations suggest that such models are incorrect, at least for LNP siRNA systems generated by the microfluidic mixing approach. For example, cryo-electron microscopy of LNP siRNA systems produced by microfluidic mixing indicates the presence of electron-dense cores rather than the aqueous cores consistent with vesicular structure. As noted above, formulation of LNP siRNA systems can routinely result in siRNA encapsulation efficiencies approaching 100%, an observation that is not consistent with bilayer structures where maximum encapsulation efficiencies of 50% might be expected.

The structure of LNP siRNA systems was evaluated employing a variety of physical and enzymatic assays. The results obtained indicate that these LNP siRNA systems have a solid core interior of consisting of siRNA monomers complexed with cationic lipid as well as lipid organized in inverted micellar or related structures.

Figure 22A:
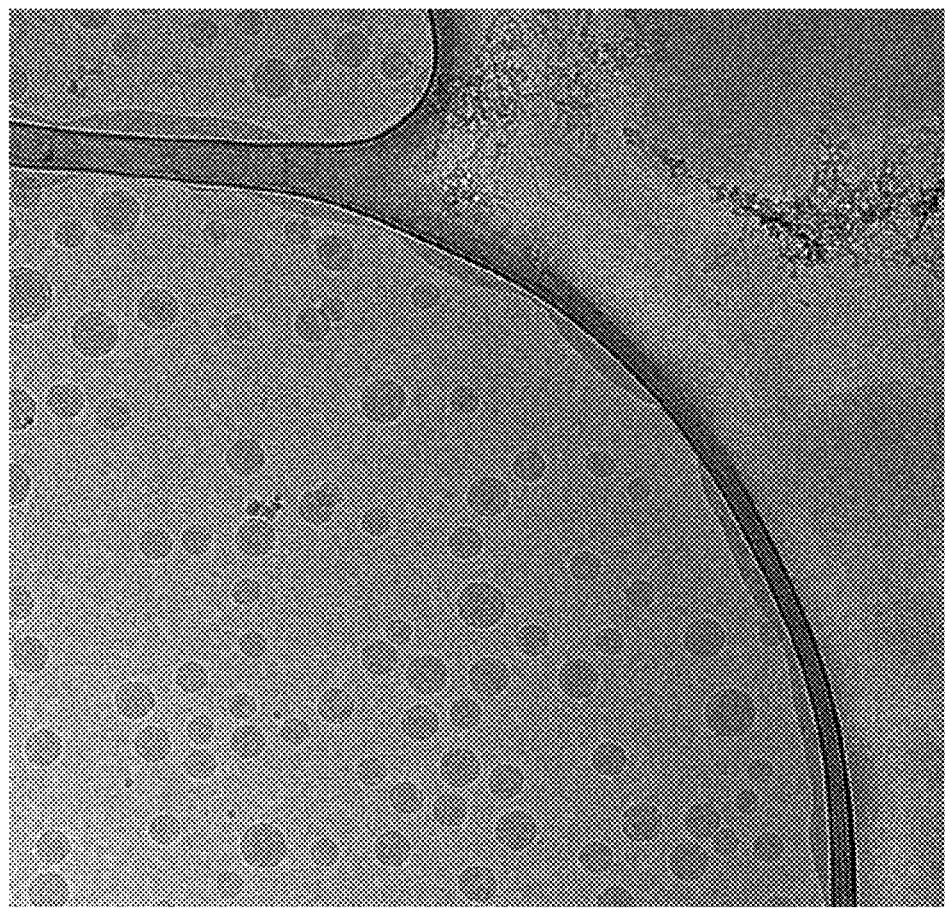
FIGS. 22A-22C illustrate cryo electron microscopy of lipid nanoparticles prepared by the microfluidics method. Empty lipid nanoparticles prepared by microfluidics (40% DLinKC2-DMA, 11.5% DSPC, 47.5% cholesterol, 1% PEG-c-DMA) showed an electron dense interior indicating solid core structure (FIG. 22A). Samples composed with POPC showed a less dense interior correlating with aqueous core vesicles (FIG. 22B). Systems containing POPC/triolein which have a hydrophobic core of triolein surrounded by a monolayer of POPC showed an electron dense interior similar to sample A (FIG. 22C).
Figure 22B:
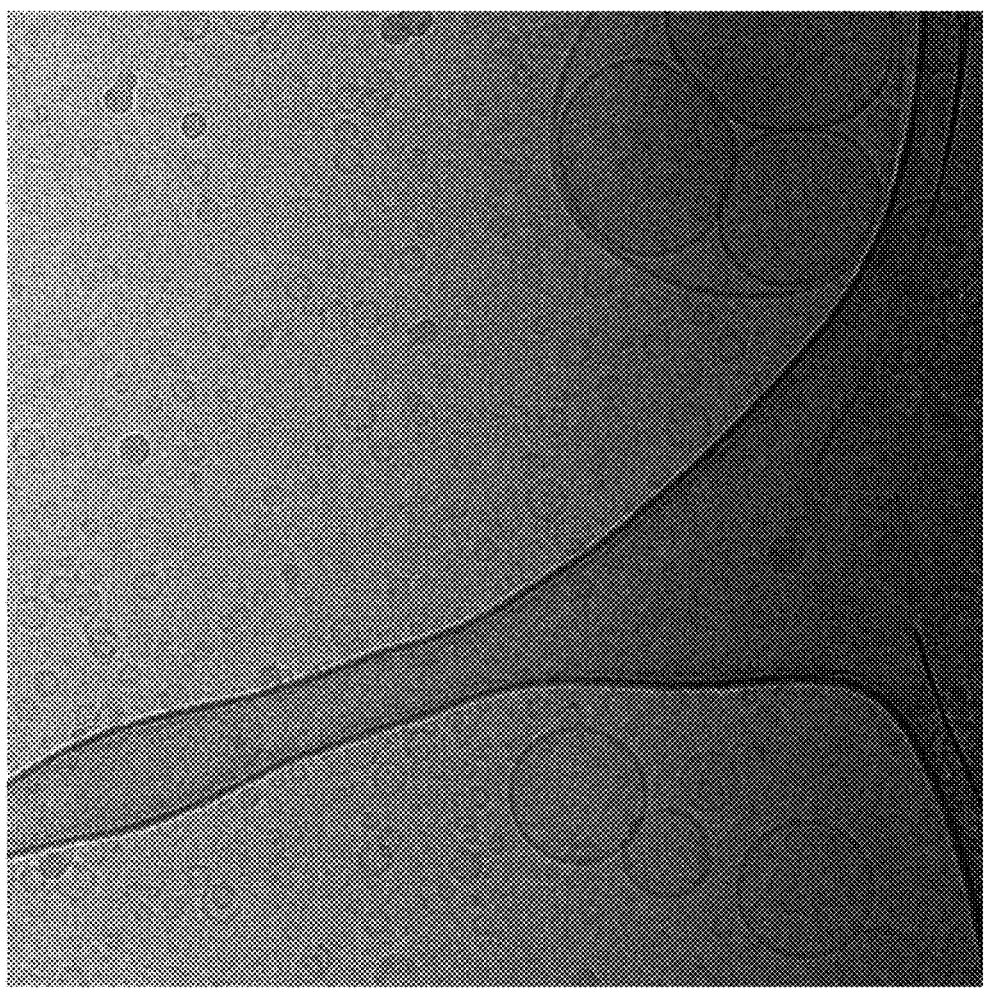
Figure 22C:
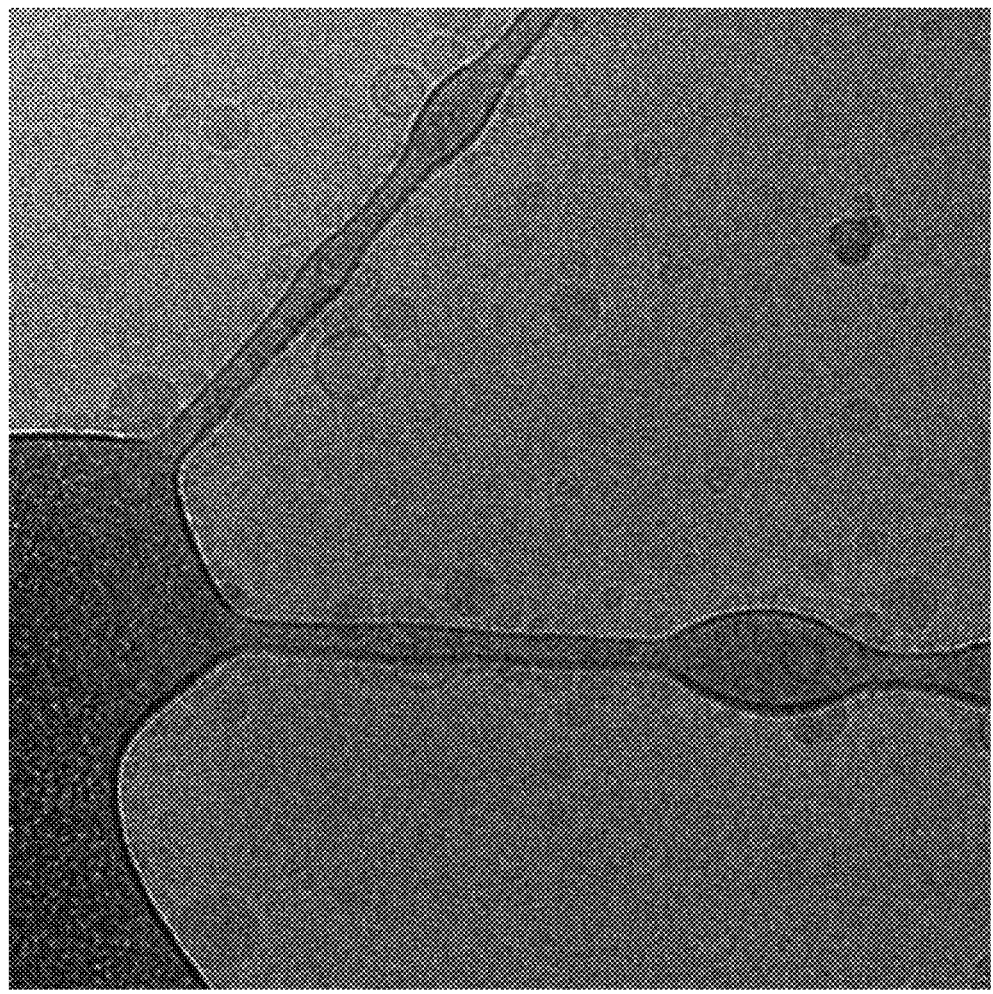

LNP systems exhibit electron dense solid core structure as indicated by cryo EM in the presence and absence of encapsulated siRNA. LNP systems produced by microfluidic mixing exhibit electron dense cores as visualized by cryo EM, consistent with a solid cores, in contrast to the aqueous core structures suggested for LNP siRNA systems created by alternative methods. This was confirmed as shown in FIG. 22A for an LNP siRNA formulation consisting of DLin-KC2-DMA/DSPC/Chol/PEG-lipid (40/11.5/47.5/1; mol/mol) containing siRNA at a 0.06 siRNA/lipid (wt/wt) content, which corresponds to a negative charge (on the siRNA) to positive charge (on the fully protonated cationic lipid) N/P ratio of 4. As a result approximately 75% of the cationic lipid is not complexed to siRNA in the LNP. The solid core electron dense structure contrasts with the less dense interior of a vesicle system composed of POPC (FIG. 22B) and is visually similar to the electron dense interior of a POPC/triolein (POPC/TO) LNP (FIG. 22C). POPC/TO LNP produced by microfluidic mixing consist of a hydrophobic core of TO surrounded by a monolayer of POPC.

An interesting feature of FIG. 22A is that 75% of the ionizable cationic lipid is not complexed to siRNA, but the LNP siRNA particle as a whole exhibits a solid core interior. This suggests that the cationic lipid may contribute to the solid core interior even when it is not complexed to siRNA. LNP systems with the same lipid composition but no siRNA were formulated employing the microfluidics process and characterized by cryo EM. As shown in FIG. 22B, the electron dense core was observed in the absence of siRNA, indicating that ionizable cationic lipids such as DLin-KC2-DMA, possibly in combination with DSPC and cholesterol, can adopt non-lamellar electron dense structures in the LNP interior.

Figure 23:
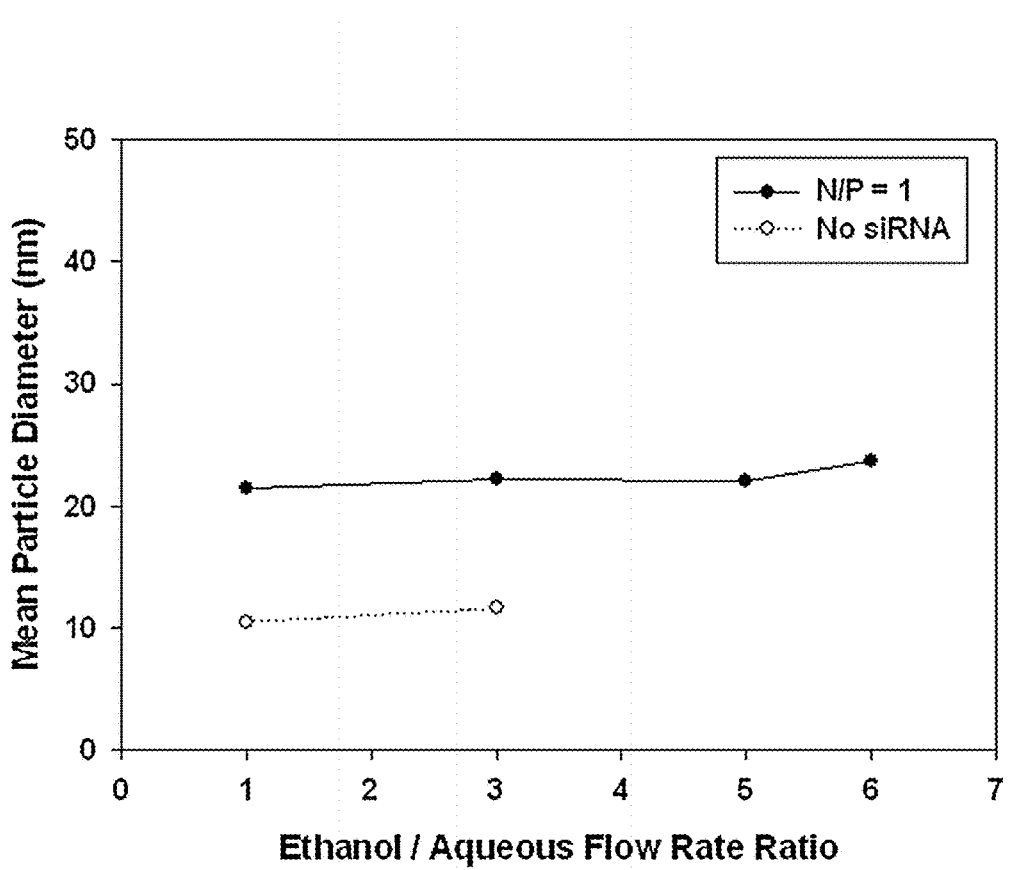
FIG. 23 illustrates limit size LNP prepared with DLinKC2-DMA/PEG-lipid system (90/10, mol/mol) using microfluidic mixing by comparing mean particle diameter (nm) as a function of ethanol/aqueous flow rate ratio for LNP were produced in the presence of siRNA (N/P=1) and without siRNA present (No siRNA). Formulation was performed using a 10 mM lipid-ethanol phase mixed with 25 mM acetate buffer, pH 4. The particle size was determined by dynamic light scattering and number-weighted mean diameters are reported.

LNP structures exhibit limit sizes indicating that ionizable cationic lipid forms inverted micellar structures in the LNP interior. The contribution of the cationic lipid to the electron dense LNP core raises the question of what the molecular structure of such LNP systems may be. It is logical to propose that the cationic lipid, in association with a counter-ion, adopts an inverted structure such as an inverted micelle, consistent with the propensity of these lipids for inverted structures such as the hexagonal $H_{II}$ phase in mixtures with anionic lipids. In turn, this would suggest that LNP systems composed of pure cationic lipid should exhibit limit sizes with diameters in the range of 10 nm, which is essentially the thickness of two bilayers surrounding an inverted micelle interior with diameter 2-3 nm. The diameter of the aqueous channels found for phosphatidylethanolamine in the $H_{II}$ phase is 2.6 nm. The microfluidics formulation process provides fast mixing kinetics that drive the generation of limit size systems for LNP systems. The limit size that could be achieved for a DLin-KC2-DMA/PEG-lipid system (90/10, mol/mol) was evaluated. As shown in FIG. 23, measurements by dynamic light scattering on these LNP formed by the microfluidic method confirm that the particle size is approximately 10 nm in diameter, a finding that is not consistent with a significant aqueous core or trapped volume.

A related question concerns the structure of the cationic lipid-siRNA complex. Again, it is logical to suppose that it consists of a distorted inverted micelle of cationic lipid surrounding the siRNA oligonucleotide. In turn, this would suggest a limit size in the range of 15-20 nm, assuming that the siRNA contained in this inverted micelle is surrounded by an interior monolayer of cationic lipid and then an outer monolayer of remaining lipid and that the dimensions of the siRNA are 2.6 nm in diameter and 4.8 nm in length. In order to determine whether this is consistent with experiment, the limit size of LNP siRNA systems consisting of DLin-KC2-DMA and PEG-lipid (90/10; mol/mol) at high levels of siRNA corresponding to an N/P ratio of one was determined. As shown in FIG. 23, the inclusion of siRNA resulted in a limit size systems of approximately 21 nm diameter, consistent with hypothesis.

Figure 24A:
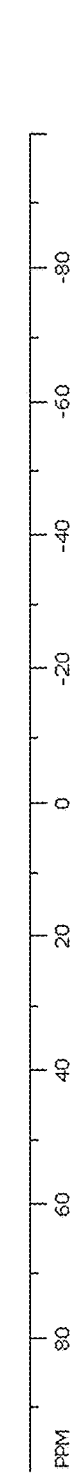
FIGS. 24A-24C illustrate $^{31}P$ NMR of siRNA encapsulated in 50% DLinKC2-DMA, 45% cholesterol, and 5% PEG-c-DMA using microfluidic mixing. DSPC was omitted to avoid conflicting phosphorus signal arising from the phospholipid. $^{31}P$ signal from the siRNA cannot be detected for intact LNP (FIG. 24A) or after the addition of 150 mM ammonium acetate (FIG. 24B). Signal can only be detected after the addition of 1% SDS to solubilize the particle (FIG. 24C).
Figure 24B:
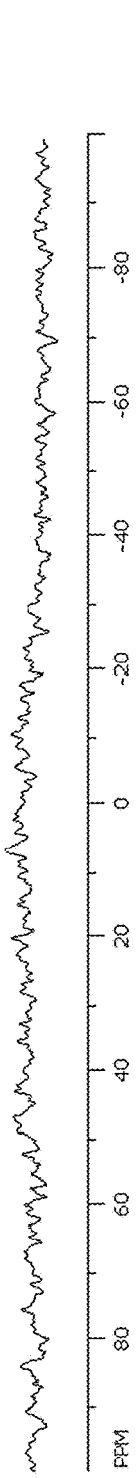
Figure 24C:
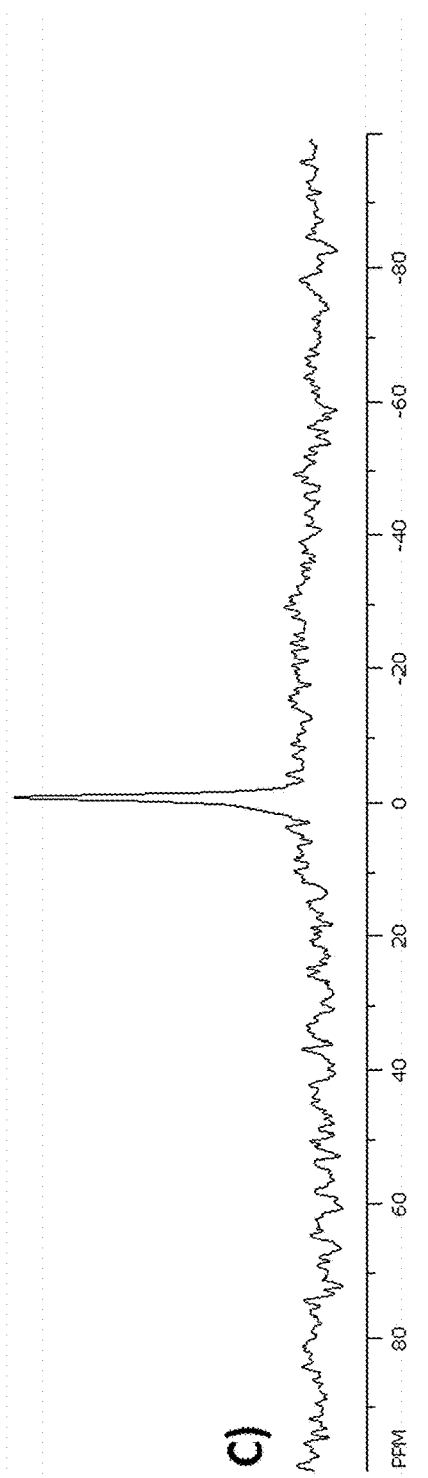

Encapsulated siRNA is immobilized in the LNP. If the siRNA is complexed to cationic lipid and localized in a solid core inside the LNP it would be expected to be less mobile than if freely tumbling in the aqueous interior of a bilayer vesicle system. The mobility of the siRNA can be probed using $^{31}$P NMR techniques. In particular, it would be expected that limited motional averaging would be possible for complexed siRNA, leading to very broad "solid state" $^{31}$P NMR resonances due to the large chemical shift anisotropy of the phosphate phosphorus. Under the conditions employed, such resonances would not be detectable. If, on the other hand, the siRNA is able to freely tumble in an aqueous environment, rapid motional averaging would be expected to lead to narrow, readily detectable, $^{31}$P NMR spectra. In order to eliminate complications arising from $^{31}$P NMR signals arising from the phospholipid phosphorus, DSPC was omitted from formulations of LNP to test this hypothesis. As shown in FIG. 24A, for LNP siRNA systems with lipid composition DLin-KC2-DMA/Chol/PEG-lipid (50/45/5 mol %) and containing siRNA (0.06 siRNA/lipid; wt/wt), no $^{31}$P NMR signal is observable for the encapsulated siRNA, consistent with immobilization within the LNP core. If the detergent sodium dodecyl sulphate is added (1%) to solubilize the LNP and release the encapsulated siRNA then a narrow $^{31}$P NMR signal is detected as shown in FIG. 24C.

Figure 25:
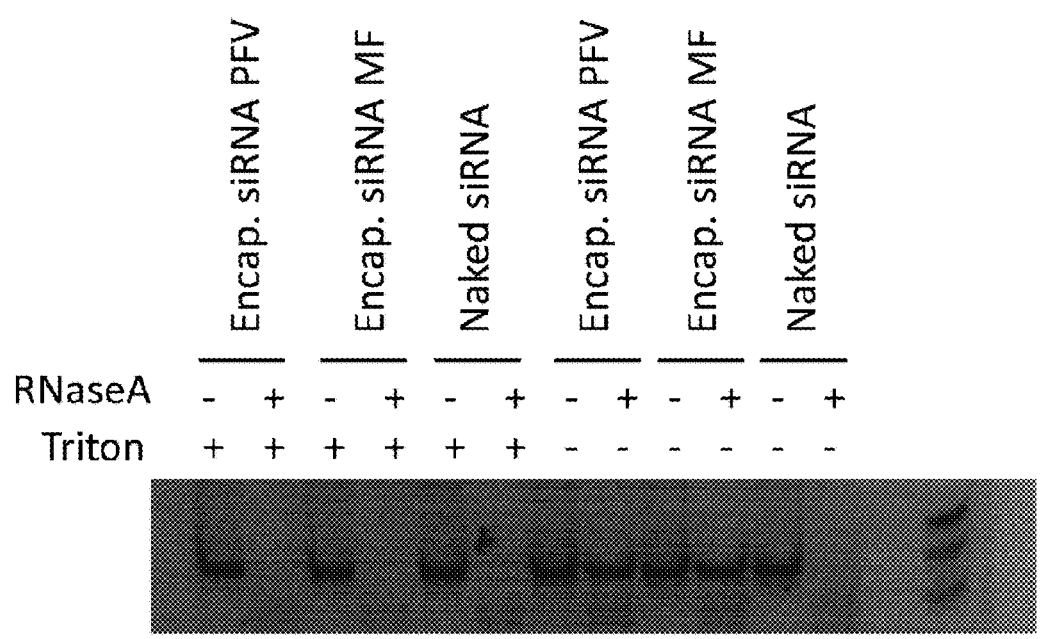
FIG. 25 is an electrophoretic gel illustrates the results of an RNase protection assay. siRNA was encapsulated using either the microfluidic method (MF) or the PFV approach, or left unencapsulated. Triton X-100 was added to completely solubilize and lyse the lipid particles. Gel electrophoresis was performed on 20% native polyacrylamide gel and siRNA visualized by staining with CYBR-Safe.

Encapsulated siRNA is fully protected from degradation by external RNase A. A test of the internalization of siRNA is that if siRNA are sequestered in the LNP core they should be fully protected from degradation by externally added RNase. LNP siRNA systems with the lipid composition DLin-KC2-DMA/DSPC/Chol/PEG-lipid (40/11/44/5 mol %) were incubated with RNase A to determine whether encapsulated siRNA could be digested. As shown in the gel presented in FIG. 25, the free siRNA is degraded, while the siRNA associated within the LNP particles made by the microfluidic method is completely protected (FIG. 25 arrow). As also shown in FIG. 25, addition of the detergent Triton X-100 to the LNP results in dissolution of the LNP, release of the siRNA, and degradation in the presence of RNase.

Encapsulated siRNA is complexed with internalized cationic lipid. The solid core of the LNP siRNA systems consists of encapsulated siRNA complexed to cationic lipid and the remaining lipid (cationic lipid, cholesterol and PEG-lipid) is either present in the core in inverted micellar or similar structures, or resident on the LNP exterior. For high siRNA contents, where essentially all of the cationic lipid is complexed with internalized siRNA, it would be expected that little cationic lipid would be localized on the LNP exterior. A fluorescence resonance energy transfer (FRET) assay was developed to determine external cationic lipid. The assay required the preparation of negatively charged vesicular LNP composed of dioleoylphosphatidylserine (DOPS) that contained the FRET pair, NBD-PE/Rh-PE at high (self-quenching) concentrations. The negatively charged DOPS LNP were then incubated with LNP siRNA systems consisting of DLin-KC2-DMA/DSPC/Chol/PEG-lipid (40/11.5/47.5/1 mol %) at pH 5.5. The pKa of DLin-KC2-DMA is 6.7 and thus nearly all the DLin-KC2-DMA on the outside of the LNP will be charged at pH 5.5, promoting an interaction and potentially fusion with the negatively charged DOPS LNP. Fusion is reported as an increase in the NBD-PE fluorescence at 535 nm as the NBD-PE and Rh-PE probes become diluted following lipid mixing.

Figure 26:
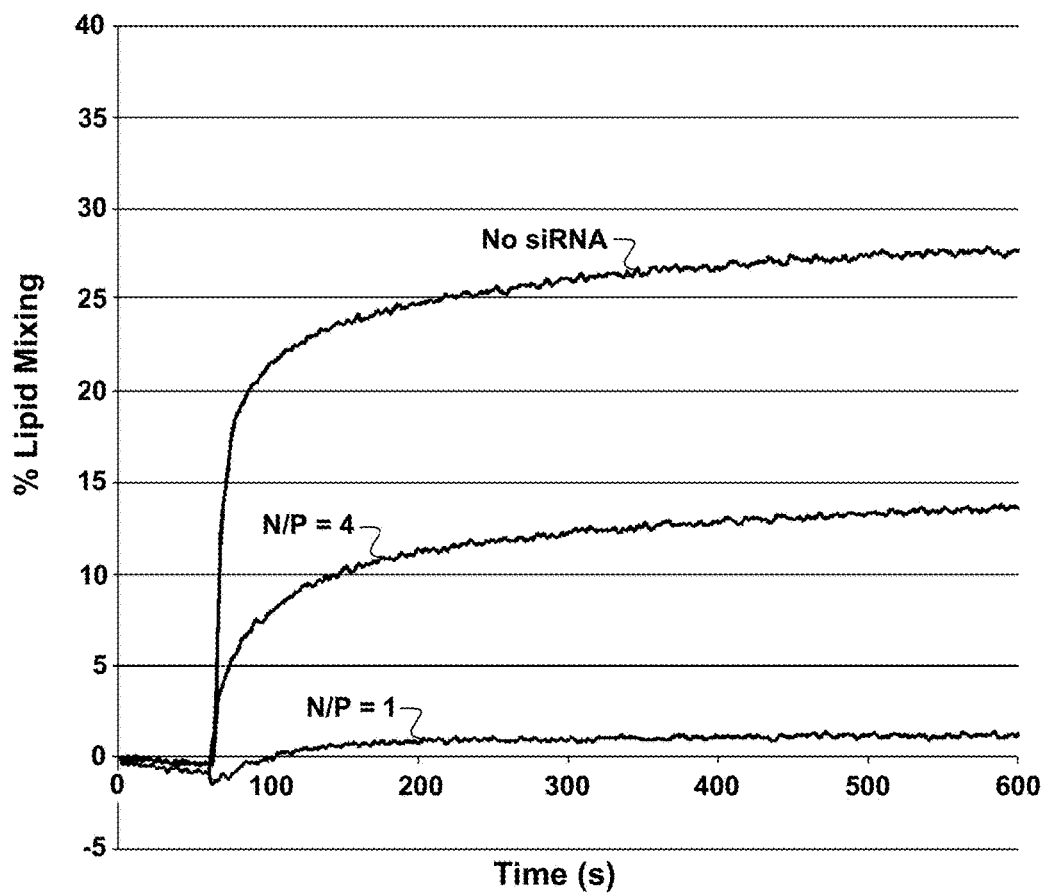
FIG. 26 illustrates the results of a lipid mixing fusion assay represented as percent lipid mixing as a function of time (seconds). To assess the amount of exposed cationic lipid present in the outermost layer of the LNP, three LNP systems were prepared: in the absence of siRNA (No siRNA), at N/P=4, and N/P=1. Lipid assay was performed at pH 5.5 to ensure nearly complete ionization of the cationic lipid, and the reaction was initiated by injecting the LNP into the cuvette containing highly anionic DOPS/NBD-PE/Rh-PE (98:1:1 molar ratio) vesicles.

As shown in FIG. 26, when the LNP systems contained no siRNA substantial fusion is observed consistent with a considerable proportion of the DLin-KC2-DMA residing on the outer monolayer of the LNP system. When the LNP systems contained siRNA at a siRNA to lipid ratio of 0.06 (wt/wt), which corresponds to a positive (cationic lipid) charge to negative (siRNA) N/P charge ratio of 4, however, fusion was considerably reduced (FIG. 26), whereas for LNP siRNA systems prepared with an N/P of 1, little or no fusion was observed, indicating that little of no DLin-KC2-DMA was present on the LNP siRNA exterior. This supports the hypothesis that high siRNA content essentially all of the cationic lipid is complexed with siRNA and sequestered in the LNP interior.

The results provide evidence that the interior of LNP siRNA systems consist of a solid core composed of siRNA monomers complexed to cationic lipids, as well as lipids arranged in inverted micelle or related structures. These results imply a model for LNP siRNA structure, provide a rationale for the high siRNA encapsulation efficiencies that can be achieved and suggest methods for manufacturing LNP siRNA systems with properties appropriate to particular applications.

Figure 27:
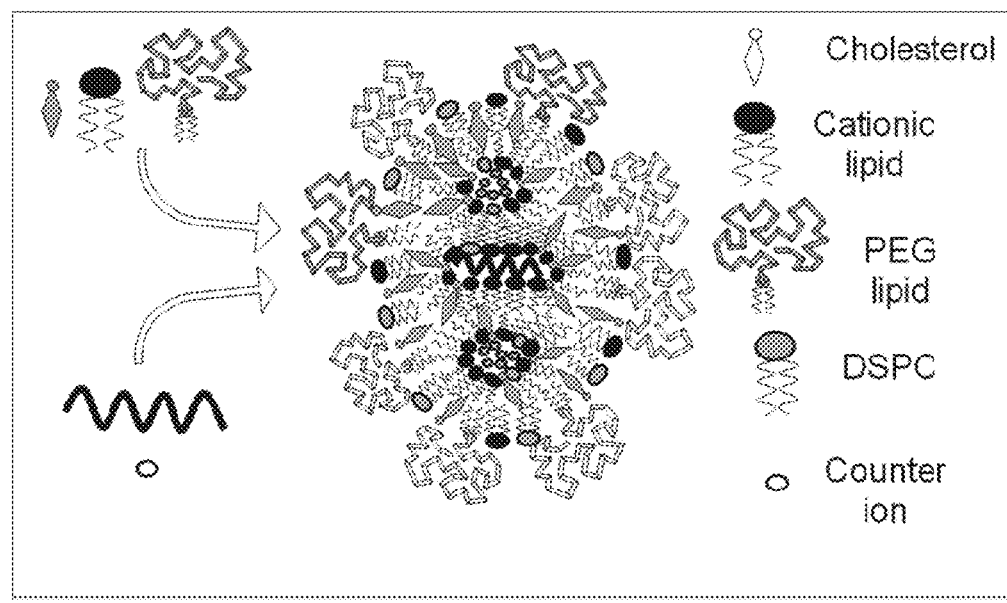
FIG. 27 is a schematic representation of the solid core LNP siRNA system formed by microfluidic mixing in accordance with the method of the invention.

The model for LNP siRNA structure based on the results is shown in FIG. 27. The model proposes that encapsulated siRNA resides in a distorted inverted micelle surrounded by cationic lipid, and that remaining lipid is organized in inverted micelles surrounding anionic counterions and also makes up the outermost monolayer.

The model provides an understanding of how siRNA encapsulation efficiencies approaching 100% can be achieved during the microfluidic mixing formulation process. This is a major problem for siRNA encapsulation in bilayer systems because, assuming the cationic lipid is equally distributed on both sides of the bilayer, a maximum of 50% siRNA internalization would be expected. The model points to ways in which LNP siRNA size, composition, and surface charge may be readily modulated. With regard to size, the limit size structure is clearly one that contains one siRNA monomer per particle, suggesting a limit size of approximately 15-20 nm. Such LNP siRNA particles are readily achieved using microfluidic method of the invention. The limit size LNP siRNA system consisting of a monomer of siRNA can be potentially used as a building block to achieve LNP siRNA systems of varying composition and surface charge using microfluidic mixing technology. Rapid mixing of preformed limit size LNP siRNA with an ethanol solution containing negatively charged lipids, for example, may be expected to result in an interaction with excess cationic lipids to produce internal inverted micellar core structures and a negatively charged surface.

The lipid particles of the invention described herein include (i.e., comprise) the components recited. In certain embodiments, the particles of the invention include the recited components and other additional components that do not affect the characteristics of the particles (i.e., the particles consist essentially of the recited components). Additional components that affect the particles' characteristics include components such as additional therapeutic agents that disadvantageously alter or affect therapeutic profile and efficacy of the particles, additional components that disadvantageously alter or affect the ability of the particles to solubilize the recited therapeutic agent components, and additional components that disadvantageously alter or affect the ability of the particles to increase the bioavailability of the recited therapeutic agent components. In other embodiments, the particles of the invention include only (i.e., consist of) the recited components.

The following examples are provided for the purpose of illustrating, not limiting, the claimed invention.

EXAMPLES

Materials
1,2-dioleoyl-sn-glycero-3-phosphocholine (DOPC), 1,2-distearoyl-sn-glycero-3-phosphocholine (DSPC), 1,2-dioleoyl-sn-glycero-3-phosphoserine (DOPS), 1,2-dioleoyl-sn-glycero-3-phosphoethanolamine-N-(7-nitro-2-1,3-benzoxadiazol-4-yl) (NBD-PE), 1,2-dioleoyl-sn-glycero-3-phosphoethanolamine-N-(lissamine rhodamine B sulfonyl) (Rh-PE) were obtained from Avanti Polar Lipids (Alabaster, Ala.). 4-(2-Hydroxyethyl) piperazine-1-ethanesulfonic acid (HEPES) and cholesterol was obtained from Sigma (St Louis, Mo.). N-[(Methoxy poly(ethylene glycol)$_{2000}$)carbamyl]-1,2-dimyristyloxlpropyl-3-amine (PEG-C-DMA) was synthesized by AlCana Technologies. 2-(N-Morpholino)ethanesulfonic acid (MES) was obtained from BDH. Ammonium acetate, sodium acetate and sodium chloride were obtained from Fisher Scientific (Fair Lawn, N.J.). RNase A was obtained from Applied Biosystems/Ambion (Austin, Tex.). Factor VII (FVII) targeting, and low GC negative control siRNA were purchased from Invitrogen (Carlsbad, Calif.). Factor VII siRNA: (SEQ ID NO: 1) 5'-GGAUCAUCUCAAGUCUUACTT-3' (FVII sense), and (SEQ ID NO: 2) 5'-GUAAGACUUGAGAUGAUCCTT-3' (FVII antisense). DLin-KC2-DMA was obtained from AlCana Technologies Inc. (Vancouver, BC).

Example 1

Preparation of LNP Systems: Preformed Vesicle Method
In the example, the preparation of an LNP-siRNA system using the preformed vesicle method is described.

Figures 15A, 15B:
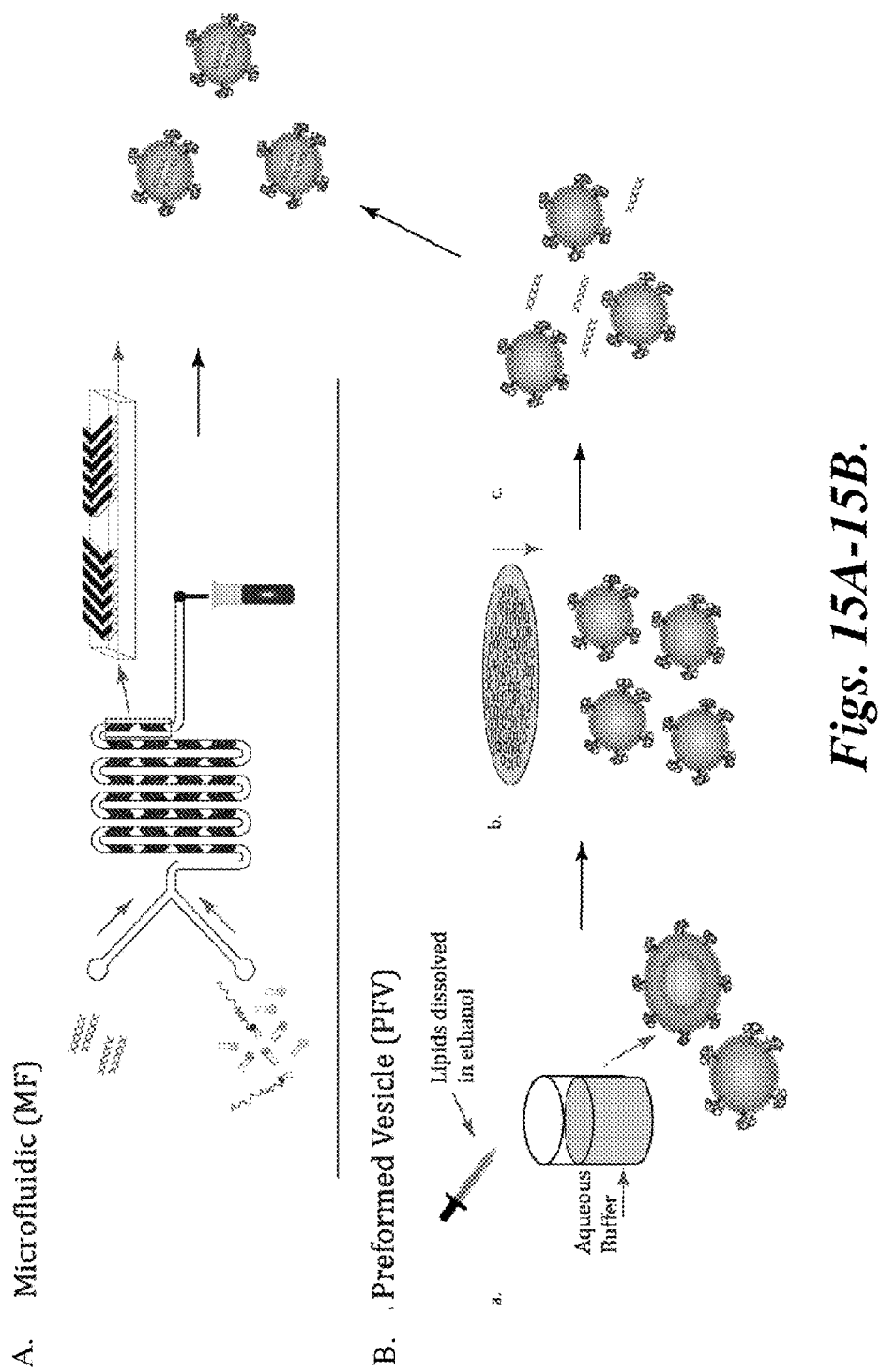
FIG. 15A is a schematic illustration of a representative microfluidic (MF) method of the invention for making lipid nanoparticles (LNP): Lipid-ethanol and siRNA-aqueous solutions are pumped into inlets of a microfluidic mixing device; herringbone features in the device induce chaotic advection of the laminar stream and cause the lipid species to rapidly mix with the aqueous stream and form lipid nanoparticles. The mixing channel is 200 μm wide and 79 μm high. The herringbone structures are 31 μm high and 50 μm thick.
FIG. 15B is a schematic illustration of a preformed vesicle (PFV) method for making lipid nanoparticles (LNP): (a) a lipid-ethanol solution is added to an aqueous solution, pH 4.0, resulting in the formation of vesicle type particles; (b) extrusion through 80 nm polycarbonate membrane (Nuclepore) at room temperature using a Lipex Extruder provides a more uniform particle distribution; and (c) addition of siRNA solution while vortexing and incubation at 35° C. for 30 minutes promotes encapsulation of siRNA.

LNP-siRNA systems were made using the preformed vesicle method as depicted in FIG. 15A and as described in N. Maurer, K. F. Wong, H. Stark, L. Louie, D. McIntosh, T. Wong, P. Scherrer, S. Semple and P. R. Cullis, "Spontaneous Entrapment of Polynucleotides Upon Electrostatic Interaction With Ethanol Destabilized Cationic Liposomes: Formation of Small Multilamellar Liposomes," *Biophys. J.*, 80:2310-2326 (2001). Cationic lipid, DSPC, cholesterol and PEG-lipid were first solubilized in ethanol at the appropriate molar ratio. The lipid mixture was then added dropwise to an aqueous buffer (citrate or acetate buffer, pH 4) while vortexing to a final ethanol and lipid concentration of 30% (v/v). The hydrated lipids were then extruded five times through two stacked 80 nm pore-sized filters (Nuclepore) at room temperature using a Lipex Extruder (Northern Lipids, Vancouver, Canada). The siRNA (solubilized in an identical aqueous solution containing 30% ethanol) was added to the vesicle suspension while mixing. A target siRNA/lipid ratio of 0.06 (wt/wt) was generally used. This mixture was incubated for 30 minutes at 35° C. to allow vesicle reorganization and encapsulation of the siRNA. The ethanol was then removed and the external buffer replaced with phosphate-buffered saline (PBS) by dialysis (12-14 k MW cut-off, Spectrum medical instruments) to 50 mM citrate buffer, pH 4.0 and then dialysis to PBS, pH 7.4.

Example 2

Preparation of LNP Systems: Microfluidic Staggered Herringbone Mixer

In the example, a representative LNP-siRNA system of the invention using a microfluidic staggered herringbone mixer is described.

LNP-siRNA Preparation.

Oligonucleotide (siRNA) solution was prepared in 25 mM acetate buffer at pH 4.0. Depending on the desired oligonucleotide-to-lipid ratio and formulation concentration, solutions were prepared at a target concentration of 0.3 mg/ml to 1.9 mg/ml total lipid. A lipid solution containing DLin-KC2-DMA, DSPC, cholesterol, and a PEG-lipid at the appropriate molar ratio was prepared in ethanol and diluted with 25 mM acetate buffer to achieve an ethanol concentration of 90% (v/v). FIG. 15B is a schematic illustration of the microfluidic apparatus used in this example. The device has two inlets, one for each of the solutions prepared above, and one outlet. The microfluidic device was produced by soft lithography, the replica molding of microfabricated masters in elastomer. The device features a 200 μm wide and 79 μm high mixing channel with herringbone structures formed by 31 μm high and 50 μm thick features on the roof of the channel. Fluidic connections were made with 1/32" I.D., 3/32" O.D. tubing that was attached to 21G1 needles for connection with syringes. 1 ml syringes were generally used for both inlet streams. A dual syringe pump (KD200, KD Scientific) was used to control the flow rate through the device. The flow rate of each stream was varied from 0.1 ml/min to 1 ml/min. The syringe pump introduces the two solutions into the microfluidic device (inlet a and inlet b in FIG. 15B), where they come into contact at a Y-junction. Insignificant mixing occurs under laminar flow by diffusion at this point, whereas the two solutions become mixed as they pass along the herringbone structures.

Mixing occurs in these structures by chaotic advection, causing the characteristic separation of laminate streams to become increasingly small, thereby promoting rapid diffusion. This mixing occurs on a millisecond time scale and results in the lipids being transferred to a progressively more aqueous environment, reducing their solubility and resulting in the spontaneous formation of LNP. By including cationic lipids in the lipid composition, entrapment of oligonucleotide species is obtained through association of the positively charged lipid head group and negatively charged oligonucleotide. Following mixing in the microfluidic device, the LNP mixture was generally diluted into a glass vial containing two volumes of stirred buffer. Ethanol is finally removed through dialysis to 50 mM citrate buffer, pH 4.0 and then dialysis to PBS, pH 7.4. Empty vesicles were similarly produced, with the oligonucleotide absent from the buffer solution.

LNP Image Analysis.

Mixing times were measured by fluorescent imaging of the mixing of fluorescein solutions with different pH values. Images were collected using an Olympus inverted confocal microscope using a 10× objective and Kalman filter mode with 2 scans per line. Twenty-five equally spaced slices were taken along the height of the channel and combined to determine total intensity profiles. For each position imaged, ten adjacent rows of pixels along the flow direction were averaged to obtain an intensity profile along the width of the channel and used to determine the extent of mixing. Mixing experiments were performed with two 10 μM fluorescein solutions supplemented with 0.5 M NaCl to suppress the formation of a liquid junction potential due to a large difference in sodium and phosphate ion concentrations. One solution contained 14 mM phosphate buffer at pH 8.88, while the other contained 1 mM phosphate buffer at pH 5.15. The increase in fluorescence of the solution initially at pH 5.15 will overwhelm the small drop in fluorescence in the basic solution, resulting in an increase in total fluorescence intensity by a factor of two. The extent of mixing was determined at approximately 2.1 mm, 6.2 mm, and 10.1 mm along the channel length using flow rates of the individual streams at 0.1 ml/min, 0.4 ml/min, 0.7 ml/min and 1.0 ml/min.

LNP Characterization.

Particle size was determined by dynamic light scattering using a Nicomp model 370 Submicron Particle Sizer (Particle Sizing Systems, Santa Barbara, Calif.). Number-weighted and intensity-weighted distribution data was used. Lipid concentrations were verified by measuring total cholesterol using the Cholesterol E enzymatic assay from Wako Chemicals USA (Richmond, Va.). Removal of free siRNA was performed with VivaPureD MiniH columns (Sartorius Stedim Biotech GmbH, Goettingen, Germany). The eluents were then lysed in 75% ethanol and siRNA was quantified by measuring absorbance at 260 nm. Encapsulation efficiency was determined from the ratio of oligonucleotide before and after removal of free oligonucleotide content, normalized to lipid content.

LNP Cyro-Transmission Electron Microscopy.

Samples were prepared by applying 3 μL of PBS containing LNP at 20-40 mg/ml total lipid to a standard electron microscopy grid with a perforated carbon film. Excess liquid was removed by blotting with a Vitrobot system (FEI, Hillsboro, Oreg.) and then plunge-freezing the LNP suspension in liquid ethane to rapidly freeze the vesicles in a thin film of amorphous ice. Images were taken under cryogenic conditions at a magnification of 29K with an AMT HR CCD side mount camera. Samples were loaded with a Gatan 70 degree cryo-transfer holder in an FEI G20 Lab6 200 kV TEM under low dose conditions with an underfocus of 5-8 μm to enhance image contrast.

In Vivo Activity of LNP-siRNA for FVII Activity.

Six to eight week old, female C57Bl/6 mice were obtained from Charles River Laboratories. LNP-siRNA containing Factor VII siRNA were filtered through a 0.2 μm filter and diluted to the required concentrations in sterile phosphate buffered saline prior to use. The formulations were administered intravenously via the lateral tail vein at a volume of 10 ml/kg. After 24 h, animals were anaesthetized with Ketamine/Xylazine and blood was collected by cardiac puncture. Samples were processed to serum (Microtainer Serum Separator Tubes; Becton Dickinson, N.J.) and tested immediately or stored at −70° C. for later analysis of serum Factor VII levels. All procedures were performed in accordance with local, state, and federal regulations as applicable and approved by the Institutional Animal Care and Use Committee (IACUC).

Serum Factor VII levels were determined using the colorimetric Biophen VII assay kit (Anaira). Control serum was pooled and serially diluted (200%-3.125%) to produce a calibration curve for calculation of FVII levels in treated animals. Appropriately diluted plasma samples from treated animals (n=3 per dosage) and a saline control group (n=4) were analyzed using the Biophen VII kit according to manufacturer's instructions. Analysis was performed in 96-well, flat bottom, non-binding polystyrene assay plates (Corning, Corning, N.Y.) and absorbance was measured at 405 nm. Factor VII levels in treated animals were determined from a calibration curve produced with the serially diluted control serum.

Example 3

LNP Systems: Solid Core

In the example, a structure of a representative LNP-siRNA system of the invention having a solid core is described.

Preparation of Lipid Nanoparticles.

LNP were prepared by mixing desired volumes of lipid stock solutions in ethanol with an aqueous phase employing the micro-mixer described above. For the encapsulation of siRNA, the desired amount of siRNA was mixed with 25 mM sodium acetate buffer at pH 4. Equal volumes of the lipid/ethanol phase and the siRNA/aqueous phase were combined in a micro-mixer containing a herring-bone structure to promote mixing. The ethanol content was quickly diluted to 25% with sodium acetate buffer upon leaving the micro-mixer. The flow rate through the micro-mixing was regulated using a dual-syringe pump (Kd Scientific). The lipid mixture then underwent a 4 hour dialysis in 50 mM MES/sodium citrate buffer (pH 6.7) followed by an overnight dialysis in phosphate buffered saline (pH 7.4).

Cryo-EM.

Samples were prepared by applying 3 μL of PBS containing LNP at 20-40 mg/ml total lipid to a standard electron microscopy grid with a perforated carbon film. Excess liquid was removed by blotting with a Vitrobot system (FEI, Hillsboro, Oreg.) and then plunge-freezing the LNP suspension in liquid ethane to rapidly freeze the vesicles in a thin film of amorphous, vitreous ice. Images were taken under cryogenic conditions at a magnification of 29K with an AMT HR CCD side mount camera. Samples were loaded with a Gatan 70 degree cryo-transfer holder in an FEI G20 Lab6 200 kV TEM under low dose conditions with an underfocus of 5-8 um to enhance image contrast.

RNase Protection Assay.

Factor VII siRNA was encapsulated with 40% DLinKC2-DMA, 11% DSPC, 44% cholesterol and 5% PEG-c-DMA using the microfluidics mixing method. 1 ug of siRNA was incubated with 0.05 ug RNase A (Ambion, Austin, Tex.) in 50 uL of 20 mM HEPES (pH 7.0) at 37° C. for 1 hour. At the end of the incubation, a 10 uL aliquot of the reaction mix was added to 30 uL FA dye (deionized formamide, TBE, PBS, xylene cyanol, bromophenol blue, yeast tRNA) to halt the RNase reaction. Gel electrophoresis was performed using 20% native polyacrylamide gel and nucleic acids were visualized by staining with CYBR-Safe (Invitrogen, Carlsbad, Calif.).

$^{31}$P-NMR Studies.

Proton decoupled $^{31}$P NMR spectra were obtained using a Bruker AVII 400 spectrometer operating at 162 MHz. Free induction decays (FID) corresponding to about $10^4$ scans were obtained with a 15 μs, 55-degree pulse with a 1 s interpulse delay and a spectral width of 64 kHz. An exponential multiplication corresponding to 50 Hz of line broadening was applied to the FID prior to Fourier transformation. The sample temperature was regulated using a Bruker BVT 3200 temperature unit. Measurements were performed at 25° C.

FRET Membrane Fusion Studies.

Fusion between LNP siRNA nanoparticles and anionic DOPS vesicles was assayed by a lipid mixing assay employing fluorescence resonance energy transfer. Labeled DOPS vesicles containing NBD-PE and Rh-PE (1 mol % each) were prepared by direct re-hydration of lipid film with the appropriate buffer followed by 10 extrusions through a 100 nm pore size polycarbonate membrane using the Lipex Extruder. LNP comprised of 40% DLinKC2-DMA, 11.5% DSPC, 47.5% cholesterol, 1% PEG-c-DMA were prepared with siRNA-to-lipid ratio (D/L ratio, wt/wt) of 0, 0.06 and 0.24. A D/L=0.24 represents an equimolar ratio of positive (cationic lipid) to negative (siRNA) charges (N/P=1). Lipid mixing experiments were conducted. Labeled DOPS vesicles and unlabeled LNP were mixed at a 1:2 mol ratio into a stirring cuvette containing 2 mL of 10 mM acetate, 10 mM MES, 10 mM HEPES, 130 mM NaCl equilibrated to pH 5.5. Fluorescence of NBD-PE was monitored using 465 nm excitation, and 535 nm emission using an LS-55 Perkin Elmer fluorometer using a 1×1 cm cuvette under continuous low speed stirring. Lipid mixing was monitored for approximately 10 min, after which 20 μL of 10% Triton X-100 was added to disrupt all lipid vesicles, representing infinite probe dilution. Lipid mixing as a percentage of infinite probe dilution was determined using the equation: % lipid mixing= $(F-F_o)/(F_{max}-F_o) \times 100$, where F is the fluorescence intensity at 535 nm during assay, $F_o$ is the initial fluorescence intensity, and $F_{max}$ is the maximum fluorescence intensity at infinite probe dilution after the addition of Triton X-100.

Example 4

Sequential Assembly of Lipid Nanoparticles

In this example, a representative method of the invention, sequential assembly, for making lipid nanoparticles is described.

The oligonucleotide (siRNA) solution was prepared at 1.31 mg/ml in 25 mM acetate buffer at pH 4.0. The lipid mixture was prepared to contain 90 mol % cationic lipid (DLin-KC2-DMA) and 10 mol % PEG-c-DMA (10 mM total lipid dissolved in ethanol). The two solutions were mixed using the microfluidic mixer at a total flow rate 2 ml/min and diluted 2-fold with 25 mM acetate buffer, pH 4.0, to bring ethanol down to about 23 vol %, forming the initial or core nanoparticle. Sequential assembly was performed by taking this initial lipid particle suspension and mixing it with another lipid solution containing an anionic lipid dioleoylphosphatidylserine (DOPS) dissolved in methanol and further diluting to approximately 25 vol % solvent (methanol and ethanol). The second lipid, DOPS, was added at about 4× molar excess to the cationic lipid. The sequential assembly process was repeated by alternating between the cationic lipid and anionic lipid.

Particle size was determined by dynamic light scattering using a Malvern Zetasizer Nano-ZS (Malvern Instruments Ltd, Malvern, Worcestershire, UK). Number-weighted distribution data was used. Zeta potential which provides a measure of the surface charge of the LNP systems was measured with the Malvern Zetasizer using disposable capillary cells (DTS1060, Malvern Instruments Ltd.). The LNP systems were diluted to approximately 0.3 mg/ml total lipid in 25 mM acetate buffer, pH 4.0.

Example 5

Preparation and Characteristics of a Representative Lipid Particle

In this example, a representative lipid particle the invention consisting only of a cationic lipid and a nucleic acid (DLin-KC2-DMA-siRNA), are described.

The siRNA solution was prepared at 0.38 mg/ml in 25 mM acetate buffer, pH 4.0. The lipid solution was prepared to contain DLin-KC2-DMA at a concentration of 10 mM in ethanol. The siRNA-to-lipid ratio was 0.06 (wt/wt). Each solution was input into the microfluidic mixer at equal flow rates and a total flow rate of 2 ml/min. The sample was further diluted with 25 mM acetate buffer, pH 4.0, to bring ethanol content to 25 vol %.

Particle size was determined by dynamic light scattering using a Nicomp model 370 Submicron Particle Sizer (Particle Sizing Systems, Santa Barbara, Calif., USA). Sample measurement was performed in 25 mM acetate and number-weighted distribution data was used. The particles had a mean particle diameter of 14.2 nm, a coefficient of variance of 0.487, and $\chi^2$ of 1.93.

While illustrative embodiments have been illustrated and described, it will be appreciated that various changes can be made therein without departing from the spirit and scope of the invention.

region for mixing the contents of the one or more streams with a microfluidic mixer;

(b) introducing a second stream comprising lipid particle-forming materials in a second solvent into the device to provide first and second streams flowing under laminar flow conditions, wherein the lipid particle-forming materials comprise a cationic lipid, and wherein the first and second solvents are not the same;

(c) flowing the one or more first streams and the one or more second streams from the first region of the device into the second region of the device; and (d) mixing the one or more first streams and the one or more second streams in the second region of the device to provide a third stream comprising lipid particles with encapsulated nucleic acid, wherein the lipid particles with encapsulated nucleic acid comprise:

(i) a substantially solid core consisting of nucleic acid, cationic lipid, and optionally second lipids; and (ii) PEG-lipid surrounding the core, wherein the lipid particle has a core and a periphery, the core has an area-averaged electron density that is not less than 20% of the maximum density of the periphery as measured by cryo transmission electron microscopy, and

---

---

The embodiments of the invention in which an exclusive property or privilege is claimed are defined as follows:

1. A method for making lipid particles with encapsulated nucleic acid, comprising:

(a) introducing a first stream comprising a nucleic acid in a first solvent into a microfluidic device; wherein the device has a first region adapted for flowing one or more streams introduced into the device and a second wherein the $^{31}$P nuclear magnetic resonance spectrum of the lipid particle measured in solution after treatment with 150 mM ammonium acetate does not exhibit a resonance due to the nucleic acid.

2. The method of claim 1, wherein the nucleic acid is encapsulated in the lipid particle with an efficiency of from 90 to 100%.

3. The method of claim 1, wherein the first solvent is an aqueous buffer and the second solvent is an aqueous alcohol.

4. The method of claim 1, wherein the first solvent is an aqueous solvent and the second solvent is an organic solvent, and wherein the volume ratio between the first and second solvent exceeds 1.0 (aqueous:organic).

5. The method of claim 1, wherein the one or more first streams and the one or more second streams are flowed at a flow rate from about 1 mL/min to about 40 mL/min.

6. The method of claim 1, wherein the particle has a diameter from about 15 nm to about 300 nm.

7. The method of claim 1, wherein the particle comprises from 30 to 95 mole percent cationic lipid.

8. The method of claim 1, wherein the cationic lipid is an amino lipid.

9. The method of claim 1, wherein the cationic lipid is selected from the group consisting of DODAC, DOTMA, DDAB, DOTAP, DOTAP•Cl, DC-Chol, DOSPA, DOGS, DOPE, DODAP, DODMA, and DMRIE.

10. The method of claim 1, wherein the cationic lipid has the formula:

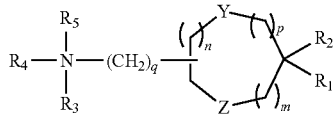

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

11. The method of claim 1, comprising from about 1 to about 5 mole percent PEG-lipid.

12. The method of claim 1, wherein the PEG-lipid is selected from the group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols.

13. The method of claim 1, wherein the PEG-lipid is selected from the group consisting of PEG-c-DOMG, PEG-c-DMA, and PEG-c-DMG.

14. The method of claim 1, wherein the second lipids are selected from the group consisting of zwitterionic lipids, sterols, and mixtures thereof.

15. The method of claim 1, wherein the second lipids are selected from the group consisting of diacylphosphatidylcholines, diacylphosphatidylethanolamines, ceramides, sphingomyelins, dihydrosphingomyelins, cephalins, and cerebrosides.

16. The method of claim 1, wherein the second lipid is cholesterol.

17. The method of claim 1, wherein the nucleic acid is a DNA, an RNA, a locked nucleic acid, a nucleic acid analog, or a plasmid capable of expressing a DNA or an RNA.

18. The method of claim 1, wherein the nucleic acid is ssDNA or dsDNA.

19. The method of claim 1, wherein the nucleic acid is mRNA, siRNA, or microRNA.

20. The method of claim 1, wherein the nucleic acid is an antisense oligonucleotide.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(21)
<223> OTHER INFORMATION: Sequence is DNA/RNA hybrid

<400> SEQUENCE: 1
ggaucaucuc aagucuuact t                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(21)
<223> OTHER INFORMATION: Sequence is DNA/RNA hybrid

<400> SEQUENCE: 2
guaagacuug agaugaucct t                                              21
```